(12) United States Patent
Gaspar et al.

(10) Patent No.: US 12,247,241 B2
(45) Date of Patent: *Mar. 11, 2025

(54) PROCESSES FOR REDUCING LACTIC ACID IN A BIOFUEL FERMENTATION SYSTEM AND PROCESSES FOR PRODUCING A FERMENTATION PRODUCT

(71) Applicant: Novozymes A/S, Bagsvaerd (DK)

(72) Inventors: Armindo Ribeiro Gaspar, Rolesville, NC (US); Victor Gabriel Guadalupe Medina, Araucaria Parana (BR); Xin Li, Raleigh, NC (US); Kelly Cristina Leite Mulder, Araucaria Parana (BR); Angela Shows, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/465,305

(22) Filed: Sep. 12, 2023

(65) Prior Publication Data
US 2024/0035051 A1 Feb. 1, 2024

Related U.S. Application Data

(62) Division of application No. 17/713,797, filed on Apr. 5, 2022, now Pat. No. 11,795,481, which is a division of application No. 16/757,459, filed as application No. PCT/US2018/056656 on Oct. 19, 2018, now Pat. No. 11,326,187.

(60) Provisional application No. 62/575,852, filed on Oct. 23, 2017.

(51) Int. Cl.
| *C12P 7/06* | (2006.01) |
| *C12N 9/02* | (2006.01) |
| *C12P 1/02* | (2006.01) |
| *C12P 19/14* | (2006.01) |

(52) U.S. Cl.
CPC .............. *C12P 7/06* (2013.01); *C12N 9/0083* (2013.01); *C12P 1/02* (2013.01); *C12P 19/14* (2013.01); *C12Y 114/99* (2013.01); *C12Y 302/01001* (2013.01)

(58) Field of Classification Search
None
See application file for complete search history.

(56) References Cited

U.S. PATENT DOCUMENTS

| 11,326,187 | B2 * | 5/2022 | Gaspar | C12P 7/06 |
| 11,795,481 | B2 * | 10/2023 | Gaspar | C12P 19/14 |
| 2009/0233340 | A1 | 9/2009 | Dailey | |
| 2011/0143410 | A1 * | 6/2011 | Soong | C12P 7/06 |
| | | | | 435/171 |
| 2017/0145443 | A1 | 5/2017 | Shihadeh | |
| 2017/0369917 | A1 | 12/2017 | Noordam | |

FOREIGN PATENT DOCUMENTS

| CN | 107109346 A | 9/2015 |
| CN | 107002107 A | 8/2017 |
| WO | 2016/045569 A1 | 3/2016 |
| WO | 2018/096019 A1 | 5/2018 |

OTHER PUBLICATIONS

Thomas et al, 2001, J Appl Microbiol 90, 819-828.
Chica et al, 2005, Curr Op Biotechnol 16, 378-384.
Singh et al, 2017, Curr Protein and Peptide Science 18, 1-11.
Allesen-Holm et al., WO 2011-080267 A2—Accession No. AZJ19467.
Muller et al., Biotechnol. Bioeng., 2016, 1-8, 9999.
US-16-757-459-1, pep_align, GenCore version 6.4.1.

* cited by examiner

*Primary Examiner* — Christian L Fronda

(57) ABSTRACT

The present invention relates to a process for reducing and/or preventing an increase in lactic acid levels in a fermentation product production process, such as especially ethanol production, wherein a lytic polysaccharide monooxygenase (LPMO) or an enzyme composition comprising an LPMO is added before or during saccharification and/or fermentation, or before or during propagation, to reduce and/or prevent an increase in lactic acid levels.

17 Claims, 3 Drawing Sheets
Specification includes a Sequence Listing.

SEQUENCE LISTING

```
Sequence total quantity: 151
SEQ ID NO: 1                moltype = AA   length = 249
FEATURE                     Location/Qualifiers
source                      1..249
                            mol_type = protein
                            organism = Thermoascus aurantiacus
SEQUENCE: 1
MSFSKIIATA GVLASASLVA GHGFVQNIVI DGKNYGGYLV NQYPYMSNPP EVIAWSTTAT    60
DLGFVDGTGY QTPDIICHRG AKPGALTAPV SPGGTVELQW TPWPDSHHGP VINYLAPCNG   120
DCSTVDKTQL EFFKIAESGL INDDNPPGIW ASDNLIAANN SWTVTIPTTI APGNYVLRHE   180
IIALHSAQNQ DGAQNYPQCI NLQVTGGGSD NPAGTLGTAL YHDTDPGILI NIYQKLSSYI   240
IPGPPLYTG                                                           249

SEQ ID NO: 2                moltype = AA   length = 236
FEATURE                     Location/Qualifiers
source                      1..236
                            mol_type = protein
                            organism = Penicillium emersonii
SEQUENCE: 2
HGFVQGIVIG DQFYSGYIVN SFPYESNPPP VIGWATTATD LGFVDGTGYQ GPDIICHRNA    60
TPAPLTAPVA AGGTVELQWT PWPDSHHGPV ITYLAPCNGN CSTVDKTTLE FFKIDQQGLI   120
DDTSPPGTWA SDNLIANNNS WTVTIPNSVA PGNYVLRHEI IALHSANNKD GAQNYPQCIN   180
IEVTGGGSDA PEGTLGEDLY HDTDPGILVD IYEPIATYTI PGPPEPTFHH HHHHHH       236

SEQ ID NO: 3                moltype = AA   length = 208
FEATURE                     Location/Qualifiers
source                      1..208
                            mol_type = protein
                            organism = Thielavia terrestris
SEQUENCE: 3
HYTWPRVNDG ADWQQVRKAD NWQDNGYVGD VTSPQIRCFQ ATPSPAPSVL NTTAGSTVTY    60
WANPDVYHPG PVQFYMARVP DGEDINSWNG DGAVWFKVYE DHPTFGAQLT WPSTGKSSFA   120
VPIPPCIKSG YYLLRAEQIG LHVAQSVGGA QFYISCAQLS VTGGGSTEPP NKVAFPGAYS   180
ATDPGILINI YYPVPTSYQN PGPAVFSC                                      208

SEQ ID NO: 4                moltype = AA   length = 250
FEATURE                     Location/Qualifiers
source                      1..250
                            mol_type = protein
                            organism = Aspergillus fumigatus
SEQUENCE: 4
MTLSKITSIA GLLASASLVA GHGFVSGIVA DGKYYGGYLV NQYPYMSNPP DTIAWSTTAT    60
DLGFVDGTGY QSPDIICHRD AKNGKLTATV AAGSQIEFQW TPWPDSHHGP VITYLAPCNG   120
DCATVDKTTL KFVKIAAQGL IDGSNPPGVW ASDELIANNN TWTVTIPASY APGNYVLRHE   180
IIALHSAGNL NGAQNYPQCF NIQITGGGSA QGSGTAGTSL YKNTDPGIKF DIYSDLSGGY   240
PIPGPALFNA                                                          250

SEQ ID NO: 5                moltype = AA   length = 229
FEATURE                     Location/Qualifiers
source                      1..229
                            mol_type = protein
                            organism = Thermoascus crustaceus
SEQUENCE: 5
HGFVQNIVID GKSYGGYIVN QYPYMSDPPE VVGWSTTATD LGFVDGTGYQ GPDIICHRGA    60
KPAALTAQVA AGGTVKLEWT PWPDSHHGPV INYLAPCNGD CSTVDKTQLK FFKIAQAGLI   120
DDNSPPGIWA SDNLIAANNS WTVTIPTTTA PGNYVLRHEI IALHSAGNKD GAQNYPQCIN   180
LKVTGNGSGN PPAGALGTAL YKDTDPGILI NIYQKLSSYV IPGPALYTG               229

SEQ ID NO: 6                moltype = AA   length = 228
FEATURE                     Location/Qualifiers
source                      1..228
                            mol_type = protein
                            organism = Penicillium emersonii
SEQUENCE: 6
HGFVQGIVIG DQFYSGYIVN SFPYESNPPP VIGWATTATD LGFVDGTGYQ GPDIICHRNA    60
TPAPLTAPVA AGGTVELQWT PWPDSHHGPV ITYLAPCNGN CSTVDKTTLE FFKIDQQGLI   120
DDTSPPGTWA SDNLIANNNS WTVTIPNSVA PGNYVLRHEI IALHSANNKD GAQNYPQCIN   180
IEVTGGGSDA PEGTLGEDLY HDTDPGILVD IYEPIATYTI PGPPEPTF                228

SEQ ID NO: 7                moltype = AA   length = 326
FEATURE                     Location/Qualifiers
source                      1..326
                            mol_type = protein
                            organism = Thielavia terrestris
SEQUENCE: 7
MKSFTIAALA ALWAQEAAAH ATFQDLWIDG VDYGSQCVRL PASNSPVTNV ASDDIRCNVG    60
TSRPTVKCPV KAGSTVTIEM HQQPGDRSCA NEAIGGDHYG PVMVYMSKVD DAVTADGSSG   120
WFKVFQDSWA KNPSGSTGDD DYWGTKDLNS CCGKMNVKIP EDIEPGDYLL RAEVIALHVA   180
```

```
ASSGGAQFYM SCYQLTVTGS GSATPSTVNF PGAYSASDPG ILINIHAPMS TYVVPGPTVY    240
AGGSTKSAGS SCSGCEATCT VGSGPSATLT QPTSTATATS APGGGGSGCT AAKYQQCGGT    300
GYTGCTTCAS GSTCSAVSPP YYSQCL                                        326

SEQ ID NO: 8               moltype = AA   length = 239
FEATURE                    Location/Qualifiers
source                     1..239
                           mol_type = protein
                           organism = Thielavia terrestris
SEQUENCE: 8
MRFDALSALA LAPLVAGHGA VTSYIIGGKT YPGYEGFSPA SSPPTIQYQW PDYNPTLSVT     60
DPKMRCNGGT SAELSAPVQA GENVTAVWKQ WTHQQGPVMV WMFKCPGDFS SSHGDGKGWF    120
KIDQLGLWGN NLNSNNWGTA IVYKTLQWSN PIPKNLAPGN YLIRHELLAL HQANTPQFYA    180
ECAQLVVSGS GSALPPSDYL YSIPVYAPQN DPGITVDIYN GGLTSYTPPG GPVWSGFEF     239

SEQ ID NO: 9               moltype = AA   length = 258
FEATURE                    Location/Qualifiers
source                     1..258
                           mol_type = protein
                           organism = Thielavia terrestris
SEQUENCE: 9
MLLTSVLGSA ALLASGAAAH GAVTSYIIAG KNYPGYQGFS PANSPNVIQW QWHDYNPVLS     60
CSDSKLRCNG GTSATLNATA APGDTITAIW AQWTHSQGPI LVVMYKCPGS FSSCDGSGAG    120
WPFKIDEAGFH GDGVKVFLDT ENPSGWDIAK LVGGNKQWSS KVPEGLAPGN YLVRHELIAL   180
HQANNPQFYP ECAQVVITGS GTAQPDASYK AAIPGYCNQN DPNIKVPIND HSIPQTYKIP    240
GPPVFKGTAS KKARDFTA                                                 258

SEQ ID NO: 10              moltype = AA   length = 226
FEATURE                    Location/Qualifiers
source                     1..226
                           mol_type = protein
                           organism = Thielavia terrestris
SEQUENCE: 10
MLANGAIVFL AAALGVSGHY TWPRVNDGAD WQQVRKADNW QDNGYVGDVT SPQIRCFQAT     60
PSPAPSVLNT TAGSTVTYWA NPDVYHPGPV QFYMARVPDG EDINSWNGDG AVWFKVYEDH    120
PTFGAQLTWP STGKSSFAVP IPPCIKSGYY LLRAEQIGLH VAQSVGGAQF YISCAQLSVT    180
GGGSTEPPNK VAFPGAYSAT DPGILINIYY PVPTSYQNPG PAVFSC                   226

SEQ ID NO: 11              moltype = AA   length = 304
FEATURE                    Location/Qualifiers
source                     1..304
                           mol_type = protein
                           organism = Thielavia terrestris
SEQUENCE: 11
MKGLFSAAAL SLAVGQASAH YIFQQLSING NQFPVYQYIR KNTNYNSPVT DLTSDDLRCN     60
VGAQGAGTDT VTVKAGDQFT FTLDTPVYHQ GPISIYMSKA PGAASDYDGS GGWFKIKDWG    120
PTFNADGTAT WDMAGSYTYN IPTCIPDGDY LLRIQSLAIH NPWPAGIPQF YISCAQITVT    180
GGGNGNPGPT ALIPGAFKDT DPGYTVNIYT NFHNYTVPGP EVFSCNGGGS NPPPPVSSST    240
PATTTLVTST RTTSSTSSAS TPASTGGCTV AKWGQCGGNG YTGCTTCAAG STCSKQNDYY    300
SQCL                                                                304

SEQ ID NO: 12              moltype = AA   length = 317
FEATURE                    Location/Qualifiers
source                     1..317
                           mol_type = protein
                           organism = Thielavia terrestris
SEQUENCE: 12
MKGLSLLAAA SAATAHTIFV QLESGGTTYP VSYGIRDPSY DGPITDVTSD SLACNGPPNP     60
TTPSPYIINV TAGTTVAAIW RHTLTSGPDD VMDASHKGPT LAYLKKVDDA LTDTGIGGGW    120
FKIQEAGYDN GNWATSTVIT NGGFQYIDIP ACIPNGQYLL RAEMIALHAA STQGGAQLYM    180
ECAQINVVGG SGSASPQTYS IPGIYQATDP GLLINIYSMT PSSQYTIPGP PLFTCSGSGN    240
NGGGSNPSGG QTTTAKPTTT TAATTTSSAA PTSSQGGSSG CTVPQWQQCG GISFTGCTTC    300
AAGYTCKYLN DYYSQCQ                                                  317

SEQ ID NO: 13              moltype = AA   length = 249
FEATURE                    Location/Qualifiers
source                     1..249
                           mol_type = protein
                           organism = Thermoascus aurantiacus
SEQUENCE: 13
MSFSKIIATA GVLASASLVA GHGFVQNIVI DGKYYGGYLV NQYPYMSNPP EVIAWSTTAT     60
DLGFVDGTGY QTPDIICHRG AKPGALTAPV SPGGTVELQW TPWPDSHHGP VINYLAPCNG    120
DCSTVDKTQL EFFKIAESGL INDDNPPGIW ASDNLIAANN SWTVTIPTTI APGNYVLRHE    180
IIALHSAQNQ DGAQNYPQCI NLQVTGGGSD NPAGTLGTAL YHDTDPGILI NIYQKLSSYI    240
IPGPPLYTG                                                           249

SEQ ID NO: 14              moltype = AA   length = 249
FEATURE                    Location/Qualifiers
source                     1..249
```

```
                        mol_type = protein
                        organism = Trichoderma reesei
SEQUENCE: 14
MKSCAILAAL GCLAGSVLGH GQVQNFTING QYNQGFILDY YYQKQNTGHF PNVAGWYAED    60
LDLGFISPDQ YTTPDIVCHK NAAPGAISAT AAAGSNIVPQ WGPGVWPHPY GPIVTYVVEC   120
SGSCTTVNKN NLRWVKIQEA GINYNTQVWA QQDLINQGNK WTVKIPSSLR PGNYVFRHEL   180
LAAHGASSAN GMQNYPQCVN IAVTGSGTKA LPAGTPATQL YKPTDPGILF NPYTTITSYT   240
IPGPALWQG                                                          249

SEQ ID NO: 15           moltype = AA   length = 232
FEATURE                 Location/Qualifiers
source                  1..232
                        mol_type = protein
                        organism = Myceliophthora thermophila
SEQUENCE: 15
MKFTSSLAVL AAAGAQAHYT FPRAGTGGSL SGEWEVVRMT ENHYSHGPVT DVTSPEMTCY    60
QSGVQGAPQT VQVKAGSQFT FSVDPSIGHP GPLQFYMAKV PSGQTAATFD GTGAVWFKIY   120
QDGPNGLGTD SITWPSAGKT EVSVTIPSCI DDGEYLLRVE HIALHSASSV GGAQFYIACA   180
QLSVTGGSGT LNTGSLVSLP GAYKATDPGI LFQLYWPIPT EYINPGPAPV SC           232

SEQ ID NO: 16           moltype = AA   length = 235
FEATURE                 Location/Qualifiers
source                  1..235
                        mol_type = protein
                        organism = Myceliophthora thermophila
SEQUENCE: 16
MKALSLLAAA SAVSAHTIFV QLEADGTRYP VSYGIRDPSY DGPITDVTSN DVACNGGPNP    60
TTPSSDVITV TAGTTVKAIW RHTLQSGPDD VMDASHKGPT LAYLKKVGDA TKDSGVGGGW   120
FKIQEDGYNN GQWGTSTVIS NGGEHYIDIP ACIPEGQYLL RAEMIALHAA GSPGGAQLYM   180
ECAQINIVGG SGSVPSSTVS FPGAYSPNDP GLLINIYSMS PSSSYTIPGP PVFKC         235

SEQ ID NO: 17           moltype = AA   length = 323
FEATURE                 Location/Qualifiers
source                  1..323
                        mol_type = protein
                        organism = Myceliophthora thermophila
SEQUENCE: 17
MKSFALTTLA ALAGNAAAHA TFQALWVDGV DYGAQCARLP ASNSPVTDVT SNAIRCNANP    60
SPARGKCPVK AGSTVTVEMH QQPGDRSCSS EAIGGAHYGP VMVYMSKVSD AASADGSSGW   120
FKVFEDGWAK NPSGGSGDDD YWGTKDLNSC CGKMNVKIPA DLPSGDYLLR AEALALHTAG   180
SAGGAQFYMT CYQLTVTGSG SASPPTVSFP GAYKATDPGI LVNIHAPLSG YTVPGPAVYS   240
GGSTKKAGSA CTGCESTCAV GSGPTATVSQ SPGSTATSAP GGGGGCTVQK YQQCGGEGYT   300
GCTNCASGST CSAVSPPYYS QCV                                          323

SEQ ID NO: 18           moltype = AA   length = 310
FEATURE                 Location/Qualifiers
source                  1..310
                        mol_type = protein
                        organism = Myceliophthora thermophila
SEQUENCE: 18
MKPFSLVALA TAVSGHAIFQ RVSVNGQDQG QLKGVRAPSS NSPIQNVNDA NMACNANIVY    60
HDSTIIKVPA GARVGAWWQH VIGGPQGAND PDNPIAASHK GPIQVYLAKV DNAATASPSG   120
LRWFKVAERG LNNGVWAVDE LIANNGWHYF DLPSCVAPGQ YLMRVELLAL HSASSPGGAQ   180
FYMGCAQIEV TGSGTNSGSD FVSFPGAYSA NDPGILLSIY DSSGKPTNGG RSYPIPGPRP   240
ISCSGSGDGG NNGGGGDDNN NNNGGGNNGG GGGGSVPLYG QCGGIGYTGP TTCAQGTCKV   300
SNEYYSQCLP                                                         310

SEQ ID NO: 19           moltype = AA   length = 246
FEATURE                 Location/Qualifiers
source                  1..246
                        mol_type = protein
                        organism = Myceliophthora thermophila
SEQUENCE: 19
MKLSLFSVLA TALTVEGHAI FQKVSVNGAD QGSLTGLRAP NNNPVQDVN SQDMICGQSG     60
STSNTIIEVK AGDRIGAWYQ HVIGGAQFPN DPDNPIAKSH KGPVMAYLAK VDNAATASKT   120
GLKWFKIWED TFNPSTKTWG VDNLINNNGW VYFNLPQCIA DGNYLLRVEV LALHSAYSQG   180
QAQFYQSCAQ INVSGGGSFT PPSTVSFPGA YSASDPGILI NIYGATGQPD NNGQPYTAPG   240
PAPISC                                                             246

SEQ ID NO: 20           moltype = AA   length = 354
FEATURE                 Location/Qualifiers
source                  1..354
                        mol_type = protein
                        organism = Thermoascus aurantiacus
SEQUENCE: 20
MSFSKIAAIT GAITYASLAA AHGYVTGIVA DGTYYGGYIV TQYPYMSTPP DVIAWSTKAT    60
DLGFVDPSSY ASSDIICHKG AEPGALSAKV AAGGTVELQW TDWPESHKGP VIDYLAACNG   120
DCSTVDKTKL EFFKIDESGL IDGSSAPGTW ASDNLIANNN SWTVTIPSTI APGNYVLRHE   180
IIALHSAGNT NGAQNYPQCI NLEVTGSGTD TPAGTLGTEL YKATDPGILV NIYQTLTSYD   240
```

```
IPGPALYTGG  SSGSSGSSNT  AKATTSTASS  SIVTPTPVNN  PTVTQTAVVD  VTQTVSQNAA   300
VATTTPASTA  VATAVPTGTT  FSFDSMTSDE  FVSLMRATVN  WLLSNKKHAR  DLSY         354

SEQ ID NO: 21           moltype = AA  length = 322
FEATURE                 Location/Qualifiers
source                  1..322
                        mol_type = protein
                        organism = Penicillium pinophilum
SEQUENCE: 21
MPSTKVAALS  AVLALASTVA  GHGFVQNIVI  DGKSYSGYLV  NQFPYESNPP  AVIGWATTAT    60
DLGFVAPSEY  TNADIICHKN  ATPGALSAPV  AAGGTVELQW  TTWPDSHHGP  VISYLANCNG   120
NCSTVDKTKL  DFVKIDQGGL  IDDTTPPGTW  ASDKLIAANN  SWTVTIPSTI  APGNYVLRHE   180
IIALHSAGNA  DGAQNYPQCI  NLEITGSGTA  APSGTAGEKL  YTSTDPGILV  NIYQSLSTYV   240
IPGPTLWSGA  ANGAVATGSA  TAVATTATAS  ATATPTTLVT  SVAPASSTFA  TAVVTTVAPA   300
VTDVVTVTDV  VTVTTVITTT  VL                                              322

SEQ ID NO: 22           moltype = AA  length = 444
FEATURE                 Location/Qualifiers
source                  1..444
                        mol_type = protein
                        organism = Thermoascus sp.
SEQUENCE: 22
MLSFASAKSA  VLTTLLLLGS  AQAHTLMTTL  FVDGVNQGDG  VCIRMNNNGS  TANTYIQPVT    60
SKDIACGIQG  EIGAARVCPA  KASSTLTFQF  REQPSNPNSA  PLDPSHKGPA  AVYLKKVDSA   120
IASNNAAGDG  WPKIWESVYD  ESTGKWGTTK  MIENNGHISV  KVPDDIEGGY  YLARTELLAL   180
HAANEGDPQF  YVGCAQLFID  SAGTAKPPTV  SIGEGTYDLS  MPAMTYNIYQ  TPLALPYPMY   240
GPPVYTPGSG  SGSGSGSGSA  SATRSSAIPT  ATAVTDCSSE  EDREDSVMAT  GVPVARSTLR   300
TWVDRLSWHG  KARENVKPAA  RRSALVQTEG  LKPEGCIFVN  GNWCGFEVPD  YNDAESCWAA   360
SDNCWKQSDS  CWNQTQPTGY  NNCQIWDQDK  CKPIQDSCSQ  SNPTGPPNKG  KDITPTWPPL   420
EGSMKTFTKR  TVSYRDWIMK  RKGA                                            444

SEQ ID NO: 23           moltype = AA  length = 253
FEATURE                 Location/Qualifiers
source                  1..253
                        mol_type = protein
                        organism = Penicillium sp.
SEQUENCE: 23
MLSSTTRTLA  FTGLAGLLSA  PLVKAHGFVQ  GIVIGDQFYS  GYIVNSFPYE  SNPPPVIGWA    60
TTATDLGFVD  GTGYQGPDII  CHRNATPAPL  TAPVAAGGTV  ELQWTPWPDS  HHGPVITYLA   120
PCNGNCSTVD  KTTLEFFKID  QQGLIDDTSP  PGTWASDNLI  ANNNSWTVTI  PNSVAPGNYV   180
LRHEIIALHS  ANNKDGAQNY  PQCINIEVTG  GGSDAPEGTL  GEDLYHDTDP  GILVDIYEPI   240
ATYTIPGPPE  PTF                                                         253

SEQ ID NO: 24           moltype = AA  length = 246
FEATURE                 Location/Qualifiers
source                  1..246
                        mol_type = protein
                        organism = Thielavia terrestris
SEQUENCE: 24
MKFSLVSLLA  YGLSVEAHSI  FQRVSNGQD   QGLLTGLRAP  SNNNPVQDVN  SQNMICGQSG    60
SKSQTVINVK  AGDRIGSLWQ  HVIGGAQFSG  DPDNPIAHSH  KGPVMAYLAK  VDNAASASQT   120
GLKWFKIWQD  GFDTSSKTWG  VDNLIKNNGW  VYFHLPQCLA  PGQYLLRVEV  LALHSAYQQG   180
QAQFYQSCAQ  INVSGSGSFS  PSQTVSIPGV  YSATDPSILI  NIYGSTGQPD  NGGKAYNPPG   240
PAPISC                                                                  246

SEQ ID NO: 25           moltype = AA  length = 334
FEATURE                 Location/Qualifiers
source                  1..334
                        mol_type = protein
                        organism = Thielavia terrestris
SEQUENCE: 25
MRTTFAAALA  AFAAQEVAGH  AIFQQLWHGS  SCVRMPLSNS  PVTNVGSRDM  ICNAGTRPVS    60
GKCPVKAGGT  VTVEMHQQPG  DRSCNNEAIG  GAHWGPVQVY  LSKVEDASTA  DGSTGWFKIF   120
ADTWSKKAGS  SVGDDDNWGT  RDLNACCGKM  QVKIPADIPS  GDYLLRAEAL  ALHTAGQVGG   180
AQFYMSCYQI  TVSGGGSASP  ATVKFPGAYS  ANDPGIHINI  HAAVSNYVAP  GPAVYSGGTT   240
KVAGSGCQGC  ENTCKVGSSP  TATAPSGKSG  AGSDGGAGTD  GGSSSSSPDT  GSACSVQAYG   300
QCGGNGYSGC  TQCAPGYTCK  AVSPPYYSQC  APSS                                334

SEQ ID NO: 26           moltype = AA  length = 227
FEATURE                 Location/Qualifiers
source                  1..227
                        mol_type = protein
                        organism = Thielavia terrestris
SEQUENCE: 26
MKLSVAIAVL  ASALAEAHYT  FPSIGNTADW  QYVRITTNYQ  SNGPVTDVTS  DQIRCYERNP    60
GTGAQGIYNV  TAGQTINYNA  KASISHPGPM  SFYIAKVPAG  QTAATWDKGG  AVWTKIYQDM   120
PKFGSSLTWP  TMGAKSVPVT  IPRCLQNGDY  LLRAEHIALH  SASSVGGAQF  YLSCAQLTVS   180
GGSGTWNPKN  RVSFPGAYKA  TDPGILINIY  YPVPTSYSPP  GPPAETC                  227
```

```
SEQ ID NO: 27            moltype = AA  length = 223
FEATURE                  Location/Qualifiers
source                   1..223
                         mol_type = protein
                         organism = Thielavia terrestris
SEQUENCE: 27
MKLSSQLAAL TLAAASVSGH YIFEQIAHGG TKFPPYEYIR RNTNYNSPVT SLSSNDLRCN    60
VGGETAGNTT VLDVKAGDSF TFYSDVAVYH QGPISLYMSK APGSVVDYDG SGDWFKIHDW   120
GPTFSNGQAS WPLRDNYQYN IPTCIPNGEY LLRIQSLAIH NPGATPQFYI SCAQVRVSGG   180
GSASPSPTAK IPGAFKATDP GYTANIYNNF HSYTVPGPAV FQC                     223

SEQ ID NO: 28            moltype = AA  length = 368
FEATURE                  Location/Qualifiers
source                   1..368
                         mol_type = protein
                         organism = Thielavia terrestris
SEQUENCE: 28
MPSFASKTLL STLAGAASVA AHGHVSNIVI NGVSYQGYDP TSFPYMQNPP IVVGWTAADT    60
DNGFVAPDAF ASGDIICHKN ATNAKGHAVV AAGDKIFIQW NTWPESHHGP VIDYLASCGS   120
ASCETVDKTK LEFFKIDEVG LVDGSSAPGV WGSDQLIANN NSWLVEIPPT IAPGNYVLRH   180
EIIIALHSAEN ADGAQNYPQC FNLQITGTGT ATPSGVPGTS LYTPTDPGIL VNIYSAPITY  240
TVPGPALISG AVSIAQSSSA ITASGTALTG SATAPAAAAA TTTSSTTNAA AATSAAAAAG   300
TSTTTTSAAA VVQTSSSSSS APSSAAAAAT TTAAAASRPT GCSSGRSRKQ PRRHARDMVV   360
ARGAEEAN                                                            368

SEQ ID NO: 29            moltype = AA  length = 330
FEATURE                  Location/Qualifiers
source                   1..330
                         mol_type = protein
                         organism = Thielavia terrestris
SEQUENCE: 29
MPPALPQLLT TVLTALTLGS TALAHSHLAY IIVNGKLYQG FDPRPHQANY PSRVGWSTGA    60
VDDGFVTPAN YSTPDIICHI AGTSPAGHAP VRPGDRIHVQ WNGWPVGHIG PVLSYLARCE   120
SDTGCTGQNK TALRWTKIDD SSPTMQNVAG AGTQGEGTPG KRWATDVLIA ANNSWQVAVP   180
AGLPTGAYVL RNEIIALHYA ARKNGAQNYP LCMNLWVDAS GDNSSVAATT AAVTAGGLQM   240
DAYDARGFYK ENDPGVLVNV TAALSSYVVP GPTVAAGATP VPYAQQSPSV STAAGTPVVV   300
TRTSETAPYT GAMTPTVAAR MKGRGYDRRG                                    330

SEQ ID NO: 30            moltype = AA  length = 236
FEATURE                  Location/Qualifiers
source                   1..236
                         mol_type = protein
                         organism = Thielavia terrestris
SEQUENCE: 30
MKTFTALLAA AGLVAGHGYV DNATIGGQFY QNPAVLTFFQ PDRVSRSIPG NGPVTDVTLI    60
DLQCNANSTP AKLHATAAAG SDVILRWTLW PESHVGPVIT YMARCPDTGC QDWMPGTSAV   120
WFKIKEGGRD GTSNTWADTP LMTAPTSYTY TIPSCLKKGY YLVRHEIIAL HAAYTYPGAQ   180
FYPGCHQLNV TGGGSTVPSS GLVAFPGAYK GSDPGITYDA YKAQTYQIPG PAVFTC       236

SEQ ID NO: 31            moltype = AA  length = 250
FEATURE                  Location/Qualifiers
source                   1..250
                         mol_type = protein
                         organism = Thielavia terrestris
SEQUENCE: 31
MALLLLAGLA ILAGPAHAHG GLANYTVGNT WYRGYDPFTP AADQIGQPWM IQRAWDSIDP    60
IFSVNDKALA CNTPATAPTS YIPIRAGENI TAVYWYWLHP VGPMTAWLAR CDGDCRDADV   120
NEARWFKIWE AGLLSGPNLA EGMWYQKAFQ NWDGSPDLWP VTIPAGLKSG LYMIRHEILS   180
IHVEDKPQFY PECAHLNVTG GGDLLPPDEF LVKFPGAYKE DNPSIKINIY SDQYANTTNY   240
TIPGGPIWDG                                                          250

SEQ ID NO: 32            moltype = AA  length = 478
FEATURE                  Location/Qualifiers
source                   1..478
                         mol_type = protein
                         organism = Thielavia terrestris
SEQUENCE: 32
MMPSLVRFSM GLATAFASLS TAHTVFTTLF INGVDQGDGT CIRMAKKGSV CTHPIAGGLD    60
SPDMACGRDG QQAVAFTCPA PAGSKLSFEF RMWADASQPG SIDPSHLGST AIYLKQVSNI   120
SSDSAAGPGW FKIYAEGYDT AAKKWATEKL IDNGGLLSIE LPPTLPAGYY LARSEIVTIQ   180
NVTNDHVDPQ FYVGCAQLFV QGPPTTPTVP PDRLVSIPGH VHASDPGLTF NIWRDDPSKT   240
AYTVVGPAPF SPTAAPTPTS TNTNGQQQQQ QQQAIKQTDG VIPADCQLKN ANWCGAEVPA   300
YADEAGCWAS SADCFAQLDA CYTSAPPTGS RGCRLWEDWC TGIQQGCRAG RWRGPPPFHG   360
EGAAAETASA GRGGARIAAV AGCGGGTGDM VEEVFLFYWD ACSGWRRSRG GGSILARLIL   420
HVLLPLLRPR RAPRVHLLLF HLYLNFCYPG TSGFYNRLSI KLGIWPSKMS PDVAHYVK     478

SEQ ID NO: 33            moltype = AA  length = 230
FEATURE                  Location/Qualifiers
source                   1..230
```

```
                         mol_type = protein
                         organism = Thielavia terrestris
SEQUENCE: 33
MQLLVGLLLA  AVAARAHYTF  PRLVVNGQPE  DKDWSVTRMT  KNAQSKQGVQ  DPTSPDIRCY   60
TSQTAPNVAT  VPAGATVHYI  STQQINHPGP  TQYYLAKVPA  GSSAKTWDGS  GAVVFKISTT  120
MPYLDNNKQL  VWPNQNTYTT  VNTTIPADTP  SGEYLLRVEQ  IALHLASQPN  GAQFYLACSQ  180
IQITGGGNGT  PGPLVALPGA  YKSNDPGILV  NIYSMQPGDY  KPPGPPVWSG              230

SEQ ID NO: 34            moltype = AA   length = 257
FEATURE                  Location/Qualifiers
source                   1..257
                         mol_type = protein
                         organism = Thielavia terrestris
SEQUENCE: 34
MKLYLAAFLG  AVATPGAFAH  QIHGILLVNG  TETPEWKYVR  DVAWEGAYEP  EKYPNTEFFK   60
TPPQTDINNP  NITCGRNAFD  SASKTETADI  LAGSEVGFRV  SWDGNGKYGV  FWHPGPGQIY  120
LSRAPNDDLE  DYRGDGDWFK  IATGAAVSNT  EWLLWNKHDF  NFTIPKTTPP  GKYLMRIEQF  180
MPSTVEYSQW  YVNCAHVNII  GPGGGTPTGF  ARFPGTYTVD  DPGIKVPLNQ  IVNSGELPQD  240
QLRLLEYKPP  GPALWTG                                                    257

SEQ ID NO: 35            moltype = AA   length = 251
FEATURE                  Location/Qualifiers
source                   1..251
                         mol_type = protein
                         organism = Thermoascus crustaceus
SEQUENCE: 35
MAFSQIMAIT  GVFLASASLV  AGHGFVQNIV  IDGKSYGGYI  VNQYPYMSDP  PEVVGWSTTA   60
TDLGFVDGTG  YQGPDIICHR  GAKPAALTAQ  VAAGGTVKLE  WTPWPDSHHG  PVINYLAPCN  120
GDCSTVDKTQ  LKFFKIAQAG  LIDDNSPPGI  WASDNLIAAN  NSWTVTIPTT  TAPGNYVLRH  180
EIIIALHSAGN  KDGAQNYPQC  INLKVTGNGS  GNPPAGALGT  ALYKDTDPGI  LINIYQKLSS  240
YVIPGPALYT  G                                                          251

SEQ ID NO: 36            moltype = AA   length = 349
FEATURE                  Location/Qualifiers
source                   1..349
                         mol_type = protein
                         organism = Thermoascus crustaceus
SEQUENCE: 36
MSFSKILAIA  GAITYASSAA  AHGYVQGIVV  DGSYYGGYMV  TQYPYTAQPP  ELIAWSTKAT   60
DLGFVDGSGY  TSPDIICHKG  AEPGAQSAKV  AAGGTVELQW  TAWPESHKGP  VIDYLAACDG  120
DCSSVDKTAL  KFFKIDESGL  IDGNGAGTWA  SDTLIKNNNS  WTVTIPSTIA  SGNYVLRHEI  180
IALHSAGNKD  GAQNYPQCIN  LEVTGSGTEN  PAGTLGTALY  TDTDPGLLVN  IYQGLSNYSI  240
PGPALYSGNS  DNAGSLNPTT  TPSIQNAAAA  PSTSTASVVT  DSSSATQTAS  VAATTPASTS  300
AVTASPAPDT  GSDVTKYLDS  MSSDEVLTLV  RGTLSWLVSN  KKHARDLSH              349

SEQ ID NO: 37            moltype = AA   length = 436
FEATURE                  Location/Qualifiers
source                   1..436
                         mol_type = protein
                         organism = Thermoascus crustaceus
SEQUENCE: 37
MLSFIPTKSA  ALTTLLLLGT  AHAHTLMTTM  FVDGVNQGDG  VCIRMNNDGG  TANTYIQPIT   60
SKDIACGIQG  EIGASRVCPV  KASSTLTFQF  REQPNNPNSS  PLDPSHKGPA  AVYLKKVDSA  120
IASNNAAGDS  WFKIWESVYD  ESTGKWGTTK  MIENNGHISV  KVPDDIEGGY  YLARTELLAL  180
HSADQGDPQF  YVGCAQLFID  SDGTAKPPTV  SIGEGTYDLS  MPAMTYNIWE  TPLALPYPMY  240
GPPVYTPGSG  SGSVRATSSS  AVPTATESSF  VEERANPVTA  NSVYSARGKF  KTWIDKLSWR  300
GKVRENVRQA  AGRRSTLVQT  VGLKPKGCIF  VNGNWCGFEV  PDYNDAESCW  AASDNCWKQS  360
DACWNKTQPT  GYNNCQIWQD  KKCKVIQDSC  SGPNPHGPPN  KGKDLTPEWP  PLKGSMDTFS  420
KRTIGYRDWI  VRRRGA                                                     436

SEQ ID NO: 38            moltype = AA   length = 344
FEATURE                  Location/Qualifiers
source                   1..344
                         mol_type = protein
                         organism = Aspergillus aculeatus
SEQUENCE: 38
MKYIPLVIAV  AAGLARPATA  HYIFSKLVLN  GEASADWQYI  RETTRSIVYE  PTKYTSTFDN   60
LTPSDSDFRC  NLGSFSNAAK  TEVAEVAAGD  TIAMKLFYDT  SIAHPGPGQV  YMSKAPTGNV  120
QEYQGDGDWF  KIWEKTLCNT  DGDLTTEAWC  TWGMSQFEFQ  IPAATPAGEY  LVRAEHIGLH  180
GAQANEAEFF  YSCAQIKVTG  SGTGSPSLTY  QIPGLYNDTM  TLFNGLNLWT  DSAEKVQLDF  240
LETPIGDDVW  SGAGSGSPSA  ATSSTSGATL  AAQGTTTSAA  HAQAQTTITT  STSTITSLES  300
ASSTDLVAQY  GQCGGLNWSG  PTECETPYTC  VQQNPYYHQC  VNSC                   344

SEQ ID NO: 39            moltype = AA   length = 400
FEATURE                  Location/Qualifiers
source                   1..400
                         mol_type = protein
                         organism = Aspergillus aculeatus
SEQUENCE: 39
```

```
MSVAKFAGVI LGSAALVAGH GYVSGAVVDG TYYGGYIVTS YPYSSDPPET IGWSTEATDL    60
GFVDGSEYAD ADIICHKSAK PGAISAEVKA GGTVELQWTT WPDSHHGPVL TYLANCNGDC   120
SSVTKTDLEF FKIDESGLIN DDDVPGTWAS DNLIANNNSW TVTIPSDIAA GNYVLRHEII   180
ALHSAGNKDG AQNYPQCLNL KVTGGGDLAP SGTAGESLYK DTDAGILVNI YQSLSSYDIP   240
GPAMYNATSS SSSSSSSSSS SSSSSSSGSS SSAAASSSSS SSSTTAAAAA ATSAASSVTS   300
AAGSVVTQTA TAVETDTATA YQTSTEVAQV TVTGSAPQQT YVATPSSSSS ASSSSSASVS   360
TSTSLTSYFE SLSADQFLSV LKQTFTWLVS EKKHARDLSA                         400

SEQ ID NO: 40          moltype = AA  length = 389
FEATURE                Location/Qualifiers
source                 1..389
                       mol_type = protein
                       organism = Aspergillus aculeatus
SEQUENCE: 40
MKSSTFGMLA LAAAAKMVDA HTTVFAVWIN GEDQGLGNSA SGYIRSPPSN SPVKDVTSTD    60
ITCNVNGDQA AAKTLSVKGG DVVTFEWHHD SRDASDDIIA SSHKGPVMVY MAPTTAGSSG   120
KNWVKIAEDG YSDGTWAVDT LIANSGKHNI TVPDVPAGDY LFRPEIIALH EAENEGGAQF   180
YMECVQFKVT SDGANTLPDG VSLPGAYSAT DPGILFNMYG SFDSYPIPGP SVWDGTSSGS   240
SSSSSSSSSS SSAAAAVVAT SSSSSSASIE AVTTKGAVAA VSTAAAVAPT TTTAAPTTFA   300
TAVASTKKAT ACRNKTKSSS AATTAAAVAE TTSSTAAAATA AASSASSASG TAGKYERCGG   360
QGWTGATTCV DGWTCKQWNP YYYQCVESA                                     389

SEQ ID NO: 41          moltype = AA  length = 406
FEATURE                Location/Qualifiers
source                 1..406
                       mol_type = protein
                       organism = Aspergillus aculeatus
SEQUENCE: 41
MRQAQSLSLL TALLSATRVA GHGHVTNVVV NGVYYEGFDI NSFPYESDPP KVAAWTTPNT    60
GNGFISPSDY GTDDIICHQN ATNAQAHIVV AAGDKINIQW TAWPDSHHGP VLDYLARCDG   120
ECETVDKTTL EFFKIDGVGL ISDTEVPGTW GDDQLIANNN SWLVEIPPTI APGNYVLRHE   180
LIALHSAGTE DGAQNYPQCF NLQVTGSGTD EPAGTLGTKL YTEDEAGIVV NIYTSLSSYA   240
VPGPTQYSGA VSVSQSTSAI TSTGTAVVGS GSAVATSAAA ATTSAAASSA AAATTAAAVT   300
SANANTQIAQ PSSSSSYSQI AVQVPSSWTT LVTVTPPAAA ATTPAAVPEP QTPSASSGAT   360
TTSSSSGAAQ SLYGQCGGIN WTGATSCVEG ATCYQYNPYY YQCISA                  406

SEQ ID NO: 42          moltype = AA  length = 427
FEATURE                Location/Qualifiers
source                 1..427
                       mol_type = protein
                       organism = Aspergillus aculeatus
SEQUENCE: 42
MSLSKIATLL LGSVSLVAGH GYVSSIEVDG TTYGGYLVDT YYYESDPPEL IAWSTNATDD    60
GYVSPSDYES VNIICHKGSA PGALSAPVAP GGWVQMTWNT WPDHHGPVI TYMANCHGSC    120
ADVDKTTLEF FKIDAGGLID DTDVPGTWAT DELIEDSYSR NITIPSDIAP GYYVLRHEII   180
ALHSAENLDG AQNYPQCINL EVTGSETATP SGTLGTALYK ETDPGIYVDI WNTLSTYTIP   240
GPALYTAGST ATAAAAADTT TTSAGTTAEA TTAAAAVSTT ADAVPTESSA PSETSATTAN   300
PARPTAGSDI RFQPGQVKAG ASVNNSATET SSGESATTTT TSVATAASSA DSSTTSGVLS   360
GACSQEGYWY CNGGTAFQRC VNGEWDASQS VAAGTVCTAG ISETITISAA ATRRDAMRRH   420
LARPKRH                                                             427

SEQ ID NO: 43          moltype = AA  length = 267
FEATURE                Location/Qualifiers
source                 1..267
                       mol_type = protein
                       organism = Aspergillus aculeatus
SEQUENCE: 43
MLVKLISFLS AATSVAAHGH VSNIVINGVS YRGWDINSDP YNSNPPVVVA WQTPNTANGF    60
ISPDAYDTDD VICHLSATNA RGHAVVAAGD KISLQWTTWP DSHHGPVISY LANCGSSCET   120
VDKTTLEFFK IDGVGLVDES NPPGIWGDDE LIANNNSWLV EIPASIAPGY YVLRHELIAL   180
HGAGSENGAQ NYMQCFNLQV TGTGTVQPSG VLGTELYKPT DAGILVNIYQ SLSTYVVPGP   240
TLIPQAVSLV QSSSTITASG TAVTTTA                                       267

SEQ ID NO: 44          moltype = AA  length = 273
FEATURE                Location/Qualifiers
source                 1..273
                       mol_type = protein
                       organism = Aspergillus aculeatus
SEQUENCE: 44
MKYLAIFAAA AAGLARPTAA HYIFSKLILD GEVSEDWQYI RKTTRETCYL PTKFTDTFDN    60
LTPNDQDFRC NLGSFSNAAK TEVAEVEAGS TIGMQLFAGS HMRHPGPAQV FMSKAPSGNV   120
QSYEGDGSWF KIWERTLCDK SGDLTGDAWC TYGQTEIEFQ IPEATPTGEY LVRAEHIGLH   180
RAQSNQAEFY YSCAQVKVTG NGTGVPSQTY QIPGMYNDRS ELFNGLNLWS YSVENVEAAM   240
KNSIVGDEIW NGSSVPSESH VPKYKKSHAC RVY                                273

SEQ ID NO: 45          moltype = AA  length = 322
FEATURE                Location/Qualifiers
source                 1..322
                       mol_type = protein
```

```
                    organism = Aurantiporus alborubescens
SEQUENCE: 45
MRTIATFVTL VASVLPAVLA HGGVLSYSNG GNWYWGWKPY NSPDGQTTIQ RPWATYNPIT    60
DATDPTIACN NDGTSGALQL TATVAAGSAI TAYWNQVWPH DKGPMTTYLA QCPGSTCTGV   120
NAKTLKWFKI DHAGLLSGTV YSGSWASGKM IAQNSTWTTT IPATVPSGNY LIRFETIALH   180
SLPAQFYPEC AQIQITGGGS RAPTAAELVS FPGAYSNNDP GVNIDIYSNA AQSATTYVIP   240
GPPLYGGASG SGPSSAPPSS TPGSSSTSHG PTSVSTSSSA APSTTGTVTQ YGQCGGIGWA   300
GATGCISPFK CTVINDYYYQ CL                                            322

SEQ ID NO: 46           moltype = AA  length = 234
FEATURE                 Location/Qualifiers
source                  1..234
                        mol_type = protein
                        organism = Aurantiporus alborubescens
SEQUENCE: 46
MKAILAIFSA LAPLAAAHYT FPDFIVNGTT TADWVYIRET ANHYSNGPVT NVNDPEFRCY    60
ELDLQNTAAS TLTATVSAGS SVGFKANSAL YHPGYLDVYM SKATPAANSP SAGTDQSWFK   120
VYESAPVFAN GALSFPSENI QSFTFTIPKS LPSGQYLIRV EHIALHSASS YGGAQFYISC   180
AQVNVVNGGN GNPGPLVKIP GVYTGNEPGI LINIYSFPPG FSGYQSPGPA VWRG         234

SEQ ID NO: 47           moltype = AA  length = 233
FEATURE                 Location/Qualifiers
source                  1..233
                        mol_type = protein
                        organism = Trichophaea saccata
SEQUENCE: 47
MTPLKLRPLL LLVLSTTLSL VHAHYRFYEL IANGATHASF EYIRQWVPIY SNSPVTDVTS    60
VNLRCNVNAT PAAEVITVAA GSTVGFVADT TVTHPGAFTA YMAKAPEDIT EWDGNGDWFK   120
IWEKGPTSIT SSGITWDVTD TQWTFTIPSA TPNGQYLLRF EHIALHAAST VGGAQFYMSC   180
AQIQVTNGGN GSPGPTIKFP GGYSATDPGI LINIYYPIPT SYTIPGPPVW TGK          233

SEQ ID NO: 48           moltype = AA  length = 237
FEATURE                 Location/Qualifiers
source                  1..237
                        mol_type = protein
                        organism = Trichophaea saccata
SEQUENCE: 48
MKCLLSLLLA ATAVSAHTIF QEIGINGVMQ ARYDYMRLPS YDGPITDVTS TYMACNGGPN    60
PLVQISNDVA FVKAGDSITL QWAQTLTTDF NTGLIIDPSH LGPVMVYMAK VPSATGPIPN   120
SGWFKIYEDG YDPTTKTWAV TKLINNKGKV TVTIPSCLPA GDYLLRGEII ALHAASTYPG   180
AQFYMECAQL RLTSGGTKMP TTYNIPIGYS PTDPGVTFNL YNGFTSYTIP GPRPFTC      237

SEQ ID NO: 49           moltype = AA  length = 484
FEATURE                 Location/Qualifiers
source                  1..484
                        mol_type = protein
                        organism = Penicillium thomii
SEQUENCE: 49
MSLSKISGLI LGSAALVAGH GYVSGIVVDD TYYGGYLVTQ YPYESDAPEL IAWSEQETDL    60
GYIDGSEYAN SNIICHKEAK PGALEAPVKA GGSVELQWTT WPTSHHGPVI TYMANCNGDC   120
DDVFKIDQGL IS DTTEPGTWAT DNLIANNNSR TVTVPSDIAD GNYVLRHEII            180
ALHSAGETNG AQNYPQCINL KVTGGGSATP SGTLGTALYK NTDPGILINI YTSLSTYDIP   240
GPTLYTAGAA AATAASTAAS STAAAVTTAD AVTTAAAVTS SSASVEVVPT TTPSSSIVSA   300
FPTWSPSSTP PFSNSSNGWR PSFSRGPGGP RFTSAPAPQF SAPSGAQQKQ SATATPIVAT   360
PVVITMTETS TSWVTEMVTL TDKSVVQTTS AVPVVVAATT TLTEGSEPAQ TASPSVVSGS   420
SSSGSSSSST TTTSKTSTGS DYVSSDWMSY LSSLSAAEVL QMLRQTFRWM VSNDKVHARD   480
ITIN                                                                484

SEQ ID NO: 50           moltype = AA  length = 320
FEATURE                 Location/Qualifiers
source                  1..320
                        mol_type = protein
                        organism = Talaromyces stipitatus
SEQUENCE: 50
MPSTKVAALS AVLALASTVA GHGFVQNIVI DGKSYTGYLV NQYPYQSNPP AVIGWSTTAT    60
DLGFVDGSGY TNPDIICHKN AKPGQLSAPV AAGGKVELEW TTWPESHHGP VISYLANCNG   120
DCTTVDKTKL EFVKIDQRGL IDDSNPPGTW AADQLIAANN SWTVTIPESI APGNYVLRHE   180
IIALHSANNA TGAQNYPQCI NLQITGSGTA NPSGTPGEKL YTPTDPGILV NIYQSLSSYV   240
IPGPTLWSGA AAHVVATAAG SATGVASATA TPTTLVTAVS SPTGAPSVVT PEAPSVTSFA   300
PVVTVTDVVT VTTVITTTIS                                               320

SEQ ID NO: 51           moltype = AA  length = 272
FEATURE                 Location/Qualifiers
source                  1..272
                        mol_type = protein
                        organism = Thermomyces lanuginosus
SEQUENCE: 51
MKGSSAASVL LTFLAGISRT SAHGYVSNLV INGVYYRGWL PGEDPYNPDP PIGVGWETPN    60
LGNGFVTPSE ASTDAVICHK EATPARGHVS VKAGDKIYIQ WQPNPWPDSH HGPVLDYLAP   120
```

```
CNGPCESVDK TSLRFFKIDG VGLIDGSSPP GYWADDELIA NGNGWLVQIP EDIKPGNYVL    180
RHEIIALHSA GNPDGAQLYP QCFNLEITGS GTVEPEGVPA TEFYSPDDPG ILVNIYEPLS    240
TYEVPGPSLI PQAVQIEQSS SAITATGTPT PA                                 272

SEQ ID NO: 52           moltype = AA   length = 327
FEATURE                 Location/Qualifiers
source                  1..327
                        mol_type = protein
                        organism = Thermomyces lanuginosus
SEQUENCE: 52
MAFSTVTVFV TFLAFISIAS AHGFVTKITV LGDNNKDYPG FDPSTPKEVP PGLDVAWSTS     60
ASDQGYMSSS NASYHSKDFI CHRNAKPAPD AAQVHAGDKV QLHWTQWPGP EDHQGPILDY    120
LASCNGPCSN VEKASLKWTK IDEAGRFPNG TWATDLLRNG GNTWNVTIPS DLAPGEYVLR    180
NEIIALHSAR NMGGAQHYMQ CVNLNVTGTG HRELQGVSAA EFYNPTDPGI LINVWQTQSL    240
SSYHIPGPTL LAADTGNDGG HSASSTLATV TSRRLSTPSD AMPGNGSYGA ISPPLKPAKG    300
FHPVCNARFR HGSTFTLTTL VAPPART                                       327

SEQ ID NO: 53           moltype = AA   length = 274
FEATURE                 Location/Qualifiers
source                  1..274
                        mol_type = protein
                        organism = Thermomyces lanuginosus
SEQUENCE: 53
MKGSTTASLL LPLLASVTRT SAHGFVSNLV INGVFYRGWL PTEDPYKADP PIGVGWETPN     60
LGNGFVLPEE ASTDAIVCHK EAEPARGYAS VAAGDKIYIQ WQPNPWPESH HGPVIDYLAP    120
CNGDCSTVNK TSLEFFKIDG VGLIDGSSPP GKWADDELIA NGNGWLVQIP EDIKPGNYPL    180
RHEIIALHEA FNQNGAQIYP QCFNLQITGS GTVEPEGTFA TELYSPTDPG ILVDIYNPLS    240
TYVVPGPTLI PQAVEIEQSS SAVTATGTPT PAAA                               274

SEQ ID NO: 54           moltype = AA   length = 227
FEATURE                 Location/Qualifiers
source                  1..227
                        mol_type = protein
                        organism = Humicola insolens
SEQUENCE: 54
MKLSVVLTGL AAALAEAHYT FPSVGNTADW QVVRQTTNFQ SNGPVTDVNS DQIRCYERFP     60
GQGAPGIYNV TAGQTISYNA KASISHPGPM AFYIAKVPAG YTAANWDGRG AVWSKIYQDM    120
PRIAGSLTWP TNGARSVSVT IPRCLQDGHY LLRAEHIGLH SASGVGGAQF YISCAQLYVS    180
GGTGTWNPRN KVAFPGAYSP THPGIMINIY WPVPTSYTPP GPPVETC                 227

SEQ ID NO: 55           moltype = AA   length = 257
FEATURE                 Location/Qualifiers
source                  1..257
                        mol_type = protein
                        organism = Humicola insolens
SEQUENCE: 55
MRPFLAALAA ATTVHAGWV DNATIDGVFY QLYHPYMDPY MGEFAPPRIS RKLVWNGYVN      60
DVTSIDLQCG GHTAEGQIGT EPAPLHAPAT AGSTVNLRWT LWPDSHMGPI MTYMARCPDE    120
GCDKWLPVWF KIHEAGRYTT DKSYPDDIWE VTRLMYPANE GYNYTIPACL ASGHYLVRHE    180
IIALHSAWAK GEAQFYPSCH QLTVTSIGGN VREAPAEYRV SFPGAYKDDD PGIFINVWNP    240
GPYTIPGPPV WTCPESE                                                  257

SEQ ID NO: 56           moltype = AA   length = 246
FEATURE                 Location/Qualifiers
source                  1..246
                        mol_type = protein
                        organism = Humicola insolens
SEQUENCE: 56
MRLSLTTLLA SALSVQGHAI FQRVTVNGQD QGSLTGLRAP NNNPVQNVN SQDIICGAPG      60
SRSQSVINVN AGDRIGAWYQ HVIGGAQFPG DPDNPIARSH KGPISVYLAK VDNAATANHQ    120
GLQWFKIWHD GFNPSTRQWA VDTMINNNGW VYFNLPQCIA PGHYLMRVEL LALHSATYQG    180
QAQFYISCAQ INVQSGGNFT PWQTVSFPGA YQANHPGIQV NIYGAMGQPD NGGRPYQIPG    240
PEPIQC                                                              246

SEQ ID NO: 57           moltype = AA   length = 265
FEATURE                 Location/Qualifiers
source                  1..265
                        mol_type = protein
                        organism = Humicola insolens
SEQUENCE: 57
MGPTWAVILG LIAPSVLNIH GILLVNGTET PEWKYVLDVA PAVPISNPDS LPPGYQGYKV     60
DPIIGSGNPN ITCGRLAFDS APKTQIADVL AGSEVGFRVS ADGLGNRDLE KGYIPTFWHP    120
GPAQAYLSRA PNDDLYSYKG DGDWFKIAYA GPVDDLTWSL WPGVSDFNFT IPLSTPPGKY    180
LLRIENFMPT ASTGYLQFYV NCAFVNIIGP GGGTPTEFIR IPGDYTDEDP GFLVPPEQSS    240
LDGRVPRDQL KLMSYTPPGP AVWTG                                         265

SEQ ID NO: 58           moltype = AA   length = 310
FEATURE                 Location/Qualifiers
source                  1..310
```

```
                        mol_type = protein
                        organism = Humicola insolens
SEQUENCE: 58
MKALTLLAAA TAASAHTIFV QLEADGTRYP VSHGVRTPQY DGPITDVSSN DLACNGGPNP    60
TMKTDKIITV TAGSTVKAIW RHTLQSGPND VMDPSHKGPT LAYLKKVDNA LTDSGVGGGW   120
FKIQEDGHSN GNWGTLKVIN NQGIHYIDIP DCIDSGQYLL RAEMIALHAA GSPGGAQLYM   180
ECAQIEIVGG KGTVKPQTYS IPGIYKSNDP GILINIYSMS PSSQYIIPGP PLFTCNGGGG   240
SNNGGGNNGG SNPPVQQPPA TTLTTAIAQP TPICSVQQWG QCGGQGYSGC TTCASPYRCN   300
EINAWYSQCL                                                          310

SEQ ID NO: 59           moltype = AA   length = 354
FEATURE                 Location/Qualifiers
source                  1..354
                        mol_type = protein
                        organism = Humicola insolens
SEQUENCE: 59
MAPKTSTFLA SLTGAALVAA HGHVSHIIVN GVQYRNYDPT TDFYSGNPPT VIGWSALNQD    60
NGFIEPNNFG TPDIICHKSA KPGGGHVTVR AGDKISIVWT PEWPESHVGP VIDYLAACNG   120
DCETVDKTSL RFFKIDGAGY DAAAGRWAAD ALRANGNSWL VQIPADLKAG NYVLRHEIIA   180
LHGAANPNGA QAYPQCINIR VTGGGNNQPS GVPGTQLYKA SDPGILFNPW VANPQYPVPG   240
PALIPGAVSS IPQSRSTATA TGTATRPGAD TDPTGVPPVV TTTSAPAQVT TTTSSRTTSL   300
PQITTTFATS TTPPPPAATQ SKWGQCGGNG WTGPTVCAPG SSCNKLNDWY SQCI         354

SEQ ID NO: 60           moltype = AA   length = 267
FEATURE                 Location/Qualifiers
source                  1..267
                        mol_type = protein
                        organism = Humicola insolens
SEQUENCE: 60
MYLLPIAAAA LAFTTTAYAH AQVYGLRVND QHQGDGRNKY IRSPSSNSPI RWDHVTHPFL    60
ICNIRDDNQP PGPAPDFVRA FAGDRVAFQW YHARPNDPTD YVLDSSHLGV LVTWIAPYTD   120
GPGTGPIWTK IHQDGWNGTH WATSRLISNG GFVEFRLPGS LKPGKYLVRQ EIIALHQADM   180
PGPNRGPEFY PSCAQLEVFG SGEAAPPQGY DINKGYAESG DKLWFNIYIN KNDEFKMPGP   240
EVWDGGCRFG ERWATEEPGK PKVNQHG                                       267

SEQ ID NO: 61           moltype = AA   length = 237
FEATURE                 Location/Qualifiers
source                  1..237
                        mol_type = protein
                        organism = Humicola insolens
SEQUENCE: 61
MKLLAPLMLA GAASAHTIFT SLEVDGRNYG TGNGVRVPSY NGPVEDVTSN SIACNGPPNP    60
TSPTDTVITV QAGQNVTAIW RYMLNTQGTS PNDIMDSSHK GPTLAYLKKV NDARTDSGVG   120
DGWFKIQHDG FDGTTWGTER VIFGQGRHTI KIPECIEPGQ YLLRAEMIAL HGAQNYPGAQ   180
FYMECAQLNI VGGTGTKKPS TVSFPGAYKG TDPGVKLSIW WPPVTNYVIP GPDVFKC      237

SEQ ID NO: 62           moltype = AA   length = 234
FEATURE                 Location/Qualifiers
source                  1..234
                        mol_type = protein
                        organism = Humicola insolens
SEQUENCE: 62
MKLLSTLAAI AATLATADAH YIFNILYVNG QRMGGEYTYV RRNSNSYFPV FPDILNSNDM    60
RCNVGARPGN TQTATVRAGD RIGFKVFNNE VIEHPGPGFI YMSKAPGSVN NYDGSGDWFK   120
VYETGLCRGG GNVDTNWCSY YKDRLEFTIP PKTPPGEYLV RIEHIGLHEG HVNRAQFYIT   180
CAQLKIEGPG GGNPNPLVKI PGIYRANDPG IAYNKWTNNP APYIMPGPKV WDGN         234

SEQ ID NO: 63           moltype = AA   length = 226
FEATURE                 Location/Qualifiers
source                  1..226
                        mol_type = protein
                        organism = Humicola insolens
SEQUENCE: 63
MLGSALLLLG TALGATAHYT FPRINSGGDW QYVRRADNWQ DNGFVGNVNS PQIRCFQSRH    60
QAAPATLNVT AGSTVTYYAN PNVYHPGPMA FYMARVPDGQ DINSWTGEGA VWFKIYHEQP   120
TGLGQQLRWS SDGKNSFQVQ IPRCIRSGYY LLRAEHIGLH SAGSPGGAQF YISCAQLAVN   180
GGGSTEPPNK VSFPGAYSPS DPGIQINIYW PVPTSYKNPG PPVFQC                  226

SEQ ID NO: 64           moltype = AA   length = 231
FEATURE                 Location/Qualifiers
source                  1..231
                        mol_type = protein
                        organism = Humicola insolens
SEQUENCE: 64
MKLLPGLLLA ATAAQAHYTF PRLVVNGQPE ERDWSVTRMT KNHQSKSGIE NPTSPDIRCY    60
SSQTAPNVAI VPAGSTIHYI STQQINHPGP TQYYLAKVPA GQSAKTWDGS GNVWFKIATS   120
MPEYDQNRQL VWPGHNTYQT INATIPANTP SGEYLLRVEQ IALHMASQPN KAQFYISCSQ   180
IQITNGGNGT PGPLVAFPGA YRSNDPGILV NLYSGMQPSQ YQPPGPAVWR G            231
```

```
SEQ ID NO: 65              moltype = AA  length = 248
FEATURE                    Location/Qualifiers
source                     1..248
                           mol_type = protein
                           organism = Humicola insolens
SEQUENCE: 65
MLLNSVIGSA VLLATGAAAH GAVTSYVIAG KNYPGYNGYA PSTTPNTIQW QWSTYDPIYS    60
ATDPKLRCNG GRSATQSAPA APGDNITAIW QQWTHSQGPI LVWMYKCPGA FSSCDGSGQG   120
WPKIDEAGFN GDGKTVFLDT ERPSGWEIAK LVGGNKGWTS TIPKNLAPGN YLVRHELIAL   180
HQANAPQWYP ECAQVVITGS GTKEPPASYK AAIPGYCNQN DPNIRVPIND HSIPQTYKIP   240
GPPVWRGE                                                             248

SEQ ID NO: 66              moltype = AA  length = 233
FEATURE                    Location/Qualifiers
source                     1..233
                           mol_type = protein
                           organism = Humicola insolens
SEQUENCE: 66
MKLTTSIALL AAAGAQAHYT FPRTKVDGVT SGEWETIRIT ENHWSHGPVT DVTSQAMTCY    60
EKTPGQGAPK TVNVKAGGTV TFTVDTDVGH PGPLHFYLAK VPAGKTAATF DGKGAVWFKI   120
YQDGPGGLGT SSLTWPSFGK KEVSVQIPPC VQDGEYLLRV EHIALHSAAS VGGAQLYISC   180
AQINVTGGTG TLNPGQLVSF PGAYKPTDPG ILFQLYWPPP TQYINPGPAP VKC           233

SEQ ID NO: 67              moltype = AA  length = 243
FEATURE                    Location/Qualifiers
source                     1..243
                           mol_type = protein
                           organism = Humicola insolens
SEQUENCE: 67
MKTLASALIA AGLLAQYAAA HAIFQFASSG GTDFGTSCVR MPPNNSPVTS VTSSDMACNV    60
GGSRGVSGIC EVNAGSDFTV EMHAQPNDRS CASEAIGGNH FGPVMVYMAK VDDATRADGA   120
SASWFKVDEF GYDAGSKTWG TDMLNKNCGK RTFRIPSKIP SGDYLVRAEA IALHTAGQPS   180
GAQFYMSCYQ VRIKGSNNGQ LPAGVRIPGA YSATDPGILV DIWGNGFSQY TIPGPRVIDG   240
SFF                                                                  243

SEQ ID NO: 68              moltype = AA  length = 363
FEATURE                    Location/Qualifiers
source                     1..363
                           mol_type = protein
                           organism = Humicola insolens
SEQUENCE: 68
MPRFTKSIVS ALAGASLVAA HGHVTHIVIN GVLYPNFDPT SHPYLQNPPT VVGWTAANTD    60
NGFVAPDQFA SGDIICHNQA TNAGGHAVVA AGDKIWIQWD QWPESHHGPV LDYLASCGSS   120
GCESVNKLDL EFFKIGEKGL IDGSSAPGRW ASDELIANNA GWLVQIPADI APGHYVLRHE   180
IIALHAAGQP NGAQNYPQCF NLLVTGSGTA RPQGVKGTAL YTPNDKGILA GIYNAPVSYE   240
IPGPALYSGA ARNLQQSSSQ ATSTATALTG DAVPVPTQAP VTTTSSSSAD AATATSTTVQ   300
PPQQTTLTTA IATSTAAAAP TTTAGSGNGG NRPFPTRCPG LAGLGFDKRR RQLRAEEGVQ   360
VVA                                                                  363

SEQ ID NO: 69              moltype = AA  length = 296
FEATURE                    Location/Qualifiers
source                     1..296
                           mol_type = protein
                           organism = Humicola insolens
SEQUENCE: 69
MKGLLSIAAL SLAVGEASAH YIFQQLSTGG TKHPMWKYIR QHTNYNSPVI DLDSNDLRCN    60
VGARGAGTET VTVAAGSSLT FHLDTPVYHQ GPVSVYMSKA PGSVSDYDGS GGWFKIQDWG   120
PTFTGSGATW KLDDSYTFNI PSCIPDGEYL VRIQSLGIHN PWPAGIPQFY ISCAQVRVTG   180
GGNANPSPQV SIPGAFKETD PGYTANIYNN FRSYTVPGPS VFTCSGNSGG GSNPSNPNPP   240
TPTTFTTQVT TPTPASPPSC TVAKWGQCGG QGYSGCTNCE AGSTCRQQNA YYSQCI        296

SEQ ID NO: 70              moltype = AA  length = 318
FEATURE                    Location/Qualifiers
source                     1..318
                           mol_type = protein
                           organism = Humicola insolens
SEQUENCE: 70
MRPFSLVALA TAVSGHAIFQ RVSVNGVDQG QLKGVRAPSS NYPIENVNHP DFACNTNIQH    60
RDGTVIKIPA GATVGAWWQH EIGGPSFPGD PDNPIAASHK GPIQVYLAKV DNAATASPNG   120
LRWFKIAEKG LSGGVWAVDE MIRNNGWHYF TMPQCIAPGH YLMRVELLAL HSASFPGGAQ   180
FYMECAQIEV TGSGNFSPSE TVSFPGAYPA NHPGIVVSIY DAQGNANNGG REYQIPGPRP   240
ITCSGGGSNN GGGNNNGGGN NNGGGNNNGG GNNNGGGNTG GGSAPLWGQC GGNGYTGPTT   300
CAEGTCKKQN DWYSQCTP                                                  318

SEQ ID NO: 71              moltype = AA  length = 259
FEATURE                    Location/Qualifiers
source                     1..259
                           mol_type = protein
                           organism = Humicola insolens
```

```
SEQUENCE: 71
MVLRSLSILA FVARGVFAHG GLSNYTVGDT WYSGYDPFTP AAAQLSQPWL IQRQWTSIDP    60
LFSPTSPYLA CNFPGTAPPS YIPLRAGDIL TAVYWFWLHP VGPMSVWLAR CAGDCRDEDV   120
TRARWFKIWH AGFLEGPNLE LGMWYQKKFQ RWDGGPALWR VRIPRGLKKG LYMVRHEILS   180
IHVGGRPQFY PECAHLNVTE GGEVVVPGEW TRRFPGAYDD DDKSVFIDIY RPEHENRTDY   240
EIPGGPIWES LGEMELWPE                                                259

SEQ ID NO: 72           moltype = AA  length = 325
FEATURE                 Location/Qualifiers
source                  1..325
                        mol_type = protein
                        organism = Humicola insolens
SEQUENCE: 72
MRTVFAAALA ALAAREVAGH ATFQQLWVDG TDYGSTCVRL PASNSPLTDV TSSDFACNIG    60
GRRGVGGKCP VKAGGVVTIE MHQQPNDRNC RSEAIGGMHW GPVQVYLSKV PDASTAEPTQ   120
VGWFKIFSNA WAKKPGGNSG DDDYWGTREL NGCCGRMDVP IPTDLEDGDY LLRAEALALH   180
AMPGQFYMSC YQITITGGTG TAKPATVRFP GAYTNNDAGI RANIHAPLST YIAPGPEVYS   240
GGTTRAPGEG CPGCATTCQV GSSPSAQAPG HGTAVGGGAG GPSACTVQAY GQCGGQGYTG   300
CTECADGFVC RDVSAPWYSQ CQPAF                                         325

SEQ ID NO: 73           moltype = AA  length = 298
FEATURE                 Location/Qualifiers
source                  1..298
                        mol_type = protein
                        organism = Humicola insolens
SEQUENCE: 73
MRLPQVASVL ALAAQVHGHG YIYRVTADNI VYPGYDIYVD PLLQPPPYRI AYGGGQTGPV    60
YDINSKDIAC QRVHSPAPGL IAQARAGSNI TFWWSRWLYS HKGPISAWMA PYEGDIANVD   120
VNQLEFFKIG EEFHDETGKW ATEKLVDDPE GKWTVKIPAD IKPGLYVVRN EIIALHFAVR   180
MPPFFAAFTP LGPQFYMTCF AFNITGDGTA TPQGYKFPGA YSKDDPALWW DLEENKNPYP   240
GAGPKPHVSA YDVDLVPNEL YIVSPTNNAT ADELYWEAQR QALAAQAATT EYFDSIGG    298

SEQ ID NO: 74           moltype = AA  length = 298
FEATURE                 Location/Qualifiers
source                  1..298
                        mol_type = protein
                        organism = Humicola insolens
SEQUENCE: 74
MHVQSLLAGA LALAPSASAH FLFPHLMLNG VRTGAYEYVR EHDFGFMPHN NDWINSPDFR    60
CNEGSWRHRR EPKTAVVTAG VDVVGFNLHL DFDLYHPGPV TIYLSRAPGD VRDYDGSGDW   120
FKVYQLGTRQ PFNGTDEGWA TWKMKNWQFR LPAEIPAGEY LMRIEQMSVH PPYRQKEWYV   180
QCAHLKINSN YNGPAPGPTI KIPGGYKISD PAIQYDQWAQ PPPTYAPMPG PPLWPNNNPQ   240
QGNPNQGGNN GGGNQGGGNG GCTVPKWGQC GGQGYSGCRN CESGSTCRAQ NDWYSQCL    298

SEQ ID NO: 75           moltype = AA  length = 344
FEATURE                 Location/Qualifiers
source                  1..344
                        mol_type = protein
                        organism = Humicola insolens
SEQUENCE: 75
MPPPLLATVL SLLALTRGAL SHSHLAHVII NGQLYHGFDP RPNQNNHPAR VGWSTTATDD    60
GFVTPGNYSH PDIICHRGGV SPRAHAPVTA GGKVQVQWNG WPIGHVGPIL TYIAPCGGLP   120
GAEEGCTGVD KTDLRWTKID DSMPPFRFTD ATKPVSGRAQ FPIGQVWATD ALVEANNSWS   180
VVIPRNIPPG PYVLRQEIVA LHYAAKLNGA QNYPLCLNLW VEKGQQDGQE PFKFDAYDAR   240
EFYSEDHPGV LIDVMTMVGP RAVYRIPGPT VASGATRIPH SLQTSAETWV EGTPVAVTRA   300
TETVQMEITT TPAGQGAGVR TATPAMPTPT VTKRWKGRFE MGRP                   344

SEQ ID NO: 76           moltype = AA  length = 330
FEATURE                 Location/Qualifiers
source                  1..330
                        mol_type = protein
                        organism = Humicola insolens
SEQUENCE: 76
MKSLTYAALA ALWAQQTAAH ATFQQLWVDG VDYGSQCARL PPSNSPIASV TSTAMRCNNG    60
PRAAAKCPVK AGGTVTIEMH QQPGDRSCNQ DAIGGAHHGP VMVYMSKVSD APTADGSSGW   120
FKIFQDGWAK NPNGRVGDDD FWGTKDLNTC CGKMNVKIPA DIAPGDYLLR AEAIALHAAG   180
PSGGAQPYVT CYQLTVTGGG NANPPTVNFP GAYSERDPGI AVSIHGALSN YVVPGPPVYS   240
GGSEKRAGSP CEGCEATCKV GSSPSQTLAP SNPAPTSPAN GGGNNGGGNT GGGCTVPKWQ   300
QCGGQGYSGC TVCESGSTCR AQNQWYSQCV                                   330

SEQ ID NO: 77           moltype = AA  length = 216
FEATURE                 Location/Qualifiers
source                  1..216
                        mol_type = protein
                        organism = Humicola insolens
SEQUENCE: 77
MKLLLPALLA LAAESVSAHY IFQQLTVAGT KYPVWKYIRR NSNPAWLQNG PVTDLASTDL    60
RCNVGGQVSN GTETLTVRAG DQFTFHLDTA VYHGPTSLY MSRAPGKVED YDGSGPWFKI   120
YDWGPTGNNW VMRDSYTYNI PRCIPDGEYL LRIQQLGLHN PGAAPQFYIS CAQIKVTGGG   180
```

```
TTNPTPTALI PGAFRATDPG YTVNVSQTLS NSISTS                              216

SEQ ID NO: 78              moltype = AA   length = 490
FEATURE                    Location/Qualifiers
source                     1..490
                           mol_type = protein
                           organism = Humicola insolens
SEQUENCE: 78
MRSVSLLAAA FAPLATAHTV FTALFINNVH QGDGTCVRMA KQGNLATHPV SLNSNEMACG     60
RDGQQPVAFT CPAPAGAKLT LLFRMWADGS QPGSIDKSHV GPMSIYLKKV SDMNTDSAAG    120
PGWFKIWSEG YDAATKKWAT EKLIANNGLL SVNLPPGLPA GYYLARHEIV TLQNVTNNKA    180
DPQFYVGCAQ LFVQGLGTAA SVPADKTVSI PGHLNPNDPA LVFNPYTQNA ATYPSFGPPL    240
FFPNAASAGS NKAQSTLKQT SGVIPSDCLI KNANWCGREV PDYTNEAGCW TAAGNCWEQA    300
DQCYKTAPPS GHKGCKTWEE QKCNVIQNSC EAKRFSGPPN RGVKFADMDV NQLVPGAIPE    360
AVNAGQNGEA VVVDGTTSSA DEKASVDLTT SSLPTPTPAA EENGKEDERL ALDPTLTEDE    420
SFFSVEPTSE PTGVQVEVPL TTVVLLPTLT SSLNPLPTPT SISQPAHPGR PCTGRRRRPR    480
PGFPKHPRDF                                                          490

SEQ ID NO: 79              moltype = AA   length = 306
FEATURE                    Location/Qualifiers
source                     1..306
                           mol_type = protein
                           organism = Humicola insolens
SEQUENCE: 79
MPFRNAATLA LAYATTGVSA HALMYGVWVN GVDQGDGRNV YIRTPPNNSP VKDLASPDIV     60
CNVNGGRAVP DFVQASAGDT LTFEWLHNTR GDDIIDRSHL GPIITYIAPF TTGNPTGPVW    120
TKIAEQGFNP STRRWAVDDL IDNGGKTDFV LPASLAPGRY IIRQEIIAHH ESETTFESNP    180
ARGAQFYPSC VQIQVSSGSG TAVPDQNFDF NTGYTYADPG IHFNIYTSFN SYSIPGPEVW    240
TGASTGGGNG NGNGNGNATP TQPTPTPTVT PTPIETAQPV TTTTTSTRPF PTRCPGRRLK    300
REEPKA                                                              306

SEQ ID NO: 80              moltype = AA   length = 339
FEATURE                    Location/Qualifiers
source                     1..339
                           mol_type = protein
                           organism = Humicola insolens
SEQUENCE: 80
MAHPWARCVY TAIWLAASAS GHSRVWSVSV NGRYQGPGVD DYLRAPPSDS PVVDLDSPTL     60
NCNVNGNKPV PGFVEVSAGD SLEWKWYYIN PYNPSDMIIA AEHRGPIITY ITNYTDGQPQ    120
GAVWTKIDHE GYDPVTDRFA VDNLIANRGW KAIKLPMLAD GKYILRQEII ALHSAHNQGG    180
AQLYPNCIQI KVVGGKGSAV PNQNFDLNKG YTSDHPGLRF NLWQPFNNYT IPGPEVWKGV    240
VVASNGTTNS TTNLTNNTGT GFANSTMATG ETRTERSFMT LTASHSDTGV PAKSHTVAVS    300
WTTSAAVVGS PISVTTTFSS FTTTPVPTNS TGAYLYRYK                           339

SEQ ID NO: 81              moltype = AA   length = 334
FEATURE                    Location/Qualifiers
source                     1..334
                           mol_type = protein
                           organism = Malbranchea cinnamomea
SEQUENCE: 81
MSPSFKSTAI LGAVALAARV RAHGYVSGIV VDGAYHGGYI VDKYPYMPNP DDVVGWSTTA     60
TDLGFVAPDA FGDPDIICHR DGAPGAIHAK VNAGATIELQ WNTWPESHHG PVIDYLANCN    120
GDCSSVDKTS LKFFKISEAG LNDGSNAPGQ WASDDLIANN NSWTVTIPKS IAPGNYVLRH    180
EIIIALHSAGN QNGAQNYPQC FNLEITSNGS DNPEGVLGTE LYKADDPGIL FNIYQPMDSY    240
PIPGPALYTG GSSPSPNPPT STQSPVPQPT QSPPSGSNPG NGNGDDDNDN GNETPSPSLP    300
VEIPDDLTSR ELLLVAQEII ARLLELQNQL VVSN                                334

SEQ ID NO: 82              moltype = AA   length = 366
FEATURE                    Location/Qualifiers
source                     1..366
                           mol_type = protein
                           organism = Talaromyces leycettanus
SEQUENCE: 82
MHQHFRYTAL LTALLSASTR VASHGHVSNI VINGVPYQGW DIDSMPYESD PPVVVAWETP     60
NTSNGFITPD QYGTSDIICH LNATNAKGHA VVAAGDKISI QWTAWPSSHH GPVISYLANC    120
GASCETVDKT TLQFFKIDNI GFIDDSSPPG IWAADQLEAN NNTWLVEIPP TIAPGYYVLR    180
NEIIALHGAE NQDGAQNYPQ CFNLQVTGSG TDKPAGVLGT QLYSPTDPGI LVNIYTSLST    240
YIVPGPTPYS GWSVVQSSS AITASGTPVT GTGGVSPTTA ATTTSSSHST TSTTTGPTVT    300
STSHTTTTTT PTTLRTTTTT AAGGGATQTV YGQCGGSGWT GATACAAGAT CSTLNPYYAQ    360
CLPTGA                                                              366

SEQ ID NO: 83              moltype = AA   length = 364
FEATURE                    Location/Qualifiers
REGION                     174..176
                           note = misc_feature - Xaa can be any naturally occurring
                            amino acid
source                     1..364
                           mol_type = protein
                           organism = Chaetomium thermophilum
```

```
SEQUENCE: 83
MPSFASKTLI  SALAGAASVA  AHGHVKNFVI  NGLSYQAYDP  TVFPYMQNPP  IVAGWTASNT   60
DNGFVGPESY  SSPDIICHKS  ATNAKGHAVI  KAGDSVYIQW  DTWPESHHGP  VIDYLASCGS  120
AGCETVDKTQ  LEFFKIAEAG  LIDGSQAPGK  WAADQLIAQN  NSWLVTIPEN  IKPXXXGSYV  180
LRHEIIALHS  AGQTNGAQNY  PVCINLEVTG  GGSDVPSGVK  GTELYKPTDP  GILINIYQSL  240
SNYTIPGPAL  MPGAKPVTQH  TSAIIGSTTA  ITGTATAAPA  APTSTAAAIT  TSSANANPAP  300
TTTRGNANPV  PTTTLRTSTI  APQPTAAPIQ  TPTSSVGRPP  RPTRCPGLDN  FKRARRHARD  360
LAAH                                                                   364

SEQ ID NO: 84        moltype = AA  length = 344
FEATURE              Location/Qualifiers
source               1..344
                     mol_type = protein
                     organism = Trichoderma reesei
SEQUENCE: 84
MIQKLSNLLV  TALAVATGVV  GHGHINDIVI  NGVWYQAYDP  TTFPYESNPP  IVVGWTAADL   60
DNGFVSPDAY  QNPDIICHKN  ATNAKGHASV  KAGDTILFQW  VPVPWPHPGP  IVDYLANCNG  120
DCETVDKTTL  EFFKIDGVGL  LSGGDPGTWA  SDVLISNNNT  WVVKIPDNLA  PGNYVLRHEI  180
IALHSAGQAN  GAQNYPQCFN  IAVSGSGSLQ  PSGVLGTDLY  HATDPGVLIN  IYTSPLNYII  240
PGPTVVSGLP  TSVAQGSSAA  TATASATVPG  GGSGPTSRTT  TTARTTQASS  RPSSTPPATT  300
SAPAGGPTQT  LYGQCGGSGY  SGPTRCAPPA  TCSTLNPYYA  QCLN                    344

SEQ ID NO: 85        moltype = AA  length = 252
FEATURE              Location/Qualifiers
source               1..252
                     mol_type = protein
                     organism = Acrophialophora fusispora
SEQUENCE: 85
MRIEAITGLV  LASAGAVSAH  GWVDVWAIGG  KNYTGFNPTV  APWVPDQGTI  AWPAWNTDTG   60
PVYSKDVNTT  DIICSINATN  AKIYSDPIAA  GNVINLHWTV  WPDSHHGPIL  SYLAACNGDC  120
AKADKTKLKW  FKIAHAGQIS  LGTGGGQVGY  WASDKLQDDN  GTWPVTIPAS  IKPGNYVLRN  180
EIIALHSAYD  VGAAQLYPQC  VNIKITGNGR  VTPAGVVGTK  LYKETDPGLH  YNIYNDESKP  240
VYQIPGPALC  KC                                                         252

SEQ ID NO: 86        moltype = AA  length = 344
FEATURE              Location/Qualifiers
source               1..344
                     mol_type = protein
                     organism = Corynascus sepedonium
SEQUENCE: 86
MSKTSALLAG  LTGAALVAAH  GHVSHIIVNG  VYYENYDPTT  HWYQPNPPTV  IGWTAAQQDN   60
GFIEPNNFGT  SDIICHKSGS  PGGGHATVAA  GDKINIVWTP  EWPDSHIGPV  IDYLAACNGD  120
CETVNKESLR  FFKIDGAGYD  KAAGRWAAET  LRQNGNSWLV  QIPSDLKAGN  YVLRHEIIAL  180
HGAGSANGAQ  AYPQCINLRV  TGGGSSVPSG  VAGTSLYKAS  DAGILFNPYV  ASPDYPVPGP  240
ALIAGAASSI  VQSTSAVTAT  ASATAPGGGG  ANPNPTPTTT  SSSNPAPSTT  LRTTTSAAQT  300
TPPPTNGNVQ  TKYGQCGGRD  WSGPTACAAG  SSCSVLNDWY  SQCV                    344

SEQ ID NO: 87        moltype = AA  length = 347
FEATURE              Location/Qualifiers
source               1..347
                     mol_type = protein
                     organism = Corynascus sepedonium
SEQUENCE: 87
MPSSTSKGLF  SALMGAASVA  AHGHVTNIVI  NGVSYQNYDP  TSFPYMQNPP  TVVGWTASNT   60
DNGFVAPDAF  ASGDIICHRD  ATNAGGHAVV  AAGDKVFIQW  DTWPESHHGP  VLDYLASCGD  120
AGCETVDKNT  LEFFKIGEAG  LIDGSSAPGK  WASDQLIENN  NSWMVQIPAN  LAPGNYVLRH  180
EIIALHSAGQ  ANGAQNYPQC  FNLQVTGSGT  DKPAGVLGTE  LYTPTDAGIL  ANIYTSPVQY  240
EIPGPALISG  ASAVEQSSSA  ITASASAETG  SATAPPAGSA  TAAPTTTTTT  AGSDASATPS  300
SSSSSGASTT  AEPTPSATTT  AGGSTPRPTR  CPGLKRRRHA  RDVKLAL                 347

SEQ ID NO: 88        moltype = AA  length = 342
FEATURE              Location/Qualifiers
source               1..342
                     mol_type = protein
                     organism = Myceliophthora thermophila
SEQUENCE: 88
MSKASALLAG  LTGAALVAAH  GHVSHIVVNG  VYYRNYDPTT  DWYQPNPPTV  IGWTAADQDN   60
GFVEPNSFGT  PDIICHKSAT  PGGGHATVAA  GDKINIVWTP  EWPESHIGPV  IDYLAACNGD  120
CETVDKSSLR  WFKIDGAGYD  KAAGRWAADA  LRANGNSWLV  QIPSDLKAGN  YVLRHEIIAL  180
HGAQSPNGAQ  AYPQCINLRV  TGGGSNLPSG  VAGTSLYKAT  DPGILFNPYV  SSPDYTVPGP  240
ALIAGAASSI  AQSTSVATAT  GTATVPGGGG  ANPTATTTAA  TSAAPSTTLR  TTTTSAAQTT  300
APPSGDVQTK  YGQCGGNGWT  GPTVCAPGSS  CSVLNEWYSQ  CL                      342

SEQ ID NO: 89        moltype = AA  length = 254
FEATURE              Location/Qualifiers
source               1..254
                     mol_type = protein
                     organism = Talaromyces emersonii
SEQUENCE: 89
```

```
MLSSKAPVTL AFAGLAGLLS APLVKAHGFV QGIVIGDQFY SGYIVNEFPY ESNPPPVIGW    60
ATTATDLGFV DGTEYQGPDI ICHRNATPAL LTAPVAAGGT VELQWTPWPS SHHGPVITYL   120
ANCNGNCSTV DKTQLEFFKI DQSGLINDTD PPGTWASDNL IANNNSWTVT IPSTLEPGNY   180
VLRHEIIALH SAGNKDGAQN YPQCINIEVT GGGSVEPTGT LGEDLYHDTD PGILIDIYEP   240
IATYTIPGPP EPTF                                                    254

SEQ ID NO: 90            moltype = AA  length = 272
FEATURE                  Location/Qualifiers
source                   1..272
                         mol_type = protein
                         organism = Talaromyces thermophilus
SEQUENCE: 90
MKAPSAASIL LPFLASITRT SAHGFVSNIV INGVSYRGWL PNEDPYKPEP PIGVGWETPN    60
LSNGFVTPEE ALTDAIVCHK EAKPARGYAS VAAGDKIYIQ WQPIPWPESH HGPVLDYLAP   120
CNGDCQNVNK SSLEFFKIDG KGLIDGSSPP GFWADDELIA NGNGWLVQIP EDIKPGNYVL   180
RHEIIALHEG FNQNGAQLYP QCFNLQITGS GTVEPEGTPA TELYSPTDPG ILVDIYNPLS   240
TYVVPGPTLI PQAVEIEQSS SAVTATGTPT PA                                272

SEQ ID NO: 91            moltype = AA  length = 272
FEATURE                  Location/Qualifiers
source                   1..272
                         mol_type = protein
                         organism = Talaromyces thermophilus
SEQUENCE: 91
MKGSSAASVL LALLAGITRT SAHGYVSNIV VNGVYYRGWL PGEDPYNPDP PIGVGWETPN    60
LGNGFVTPEE ASTDAIICHK EAKPARGHAT VKAGDKIYIQ WQPIPWPESH HGPVLDYLAA   120
CNGDCETVDK TSLRFFKISN KGLIDGSSPP GYWADDQLIE NGNGWLVQIP EDIKPGNYVL   180
RHEIIALHAA GNPNGAQLYP QCFNLHITGS GTVEPQGIPA TELYSPDDPG ILINIYQPLT   240
TYEVPGPTPI PQAVEIEQSS SAITATGTPT PA                                272

SEQ ID NO: 92            moltype = AA  length = 863
FEATURE                  Location/Qualifiers
source                   1..863
                         mol_type = protein
                         organism = Aspergillus fumigatus
SEQUENCE: 92
MRFGWLEVAA LTAASVANAQ ELAFSPPFYP SPWADGQGEW ADAHRRAVEI VSQMTLAEKV    60
NLTTGTGWEM DRCVGQTGSV PRLGINWGLC GQDSPLGIRF SDLNSAFPAG TNVAATWDKT   120
LAYLRGKAMG EEFNDKGVDI LLGPAAGPLG KYPDGGRIWE GFSPDPVLTG VLFAETIKGI   180
QDAGVIATAK HYILNEQEHF RQVGEAQGYG YNITETISSN VDDKTMHELY LWPFADAVRA   240
GVGAVMCSYN QINNSYGCQN SQTLNKLLKA ELGFQGFVMS DWSAHHSGVG AALAGLDMSM   300
PGDISFDDGL SFWGTNLTVS VLNGTVPAWR VDDMAVRIGA AYYKVGRDRL RIPPNFSSWT   360
RDEYGWEHSA VSEGAWTKVN DFVNVQRSHS QIIREIGAAS TVLLKNTGAL PLTGKEVKVG   420
VLGEDAGSNP WGANGCPDRG CDNGTLAMAW GSGTANFPYL VTPEQAIQRE VISNGGNVFA   480
VTDNGALSQM ADVASQSSVS LVFVNADSGE GFISVDGNEG DRKNLTLWKN GEAVIDTVVS   540
HCNNTIVVIH SVGPVLIDRW YDNPNVTAII WAGLPGQESG NSLVDVLYGR VNPSAKTPFT   600
WGKTRESYGA PLLTEPNNGN GAPQDDFNEG VFIDYRHFDK HGLSYTTFGF              660
SHLRVQALNS SSSAYVPTSG ETKPAPTYGE IGSAADYLYP EGLKRITKFI YPWLNSTDLE   720
DSSDDPNYGW EDSEYIPEGA RDGSPQPLLK AGGAPGGNPT LYQDLVRVSA TITNTGNVAG   780
YEVPQLYVSL GGPNEPRVVL RKFDRIFLAP GEQKVWTTTL NRRDLANWDV EAQDWVITKY   840
PKKVHVGSSS RKLPLRAPLP RVY                                          863

SEQ ID NO: 93            moltype = AA  length = 208
FEATURE                  Location/Qualifiers
source                   1..208
                         mol_type = protein
                         organism = Myceliophthora thermophila
SEQUENCE: 93
HYTLPRVGTG SDWQHVRRAD NWQNNGFVGD VNSEQIRCFQ ATPAGAQDVY TVQAGSTVTY    60
HANPSIYHPG PMQFYLARVP DGQDVKSWTG EGAVWFKVYE EQPQFGAQLT WPSNGKSSFE   120
VPIPSCIRAG NYLLRAEHIA LHVAQSQGGA QFYISCAQLQ VTGGGSTEPS QKVSFPGAYK   180
STDPGILINI NYPVPTSYQN PGPAVFRC                                     208

SEQ ID NO: 94            moltype = AA  length = 225
FEATURE                  Location/Qualifiers
source                   1..225
                         mol_type = protein
                         organism = Myceliophthora thermophila
SEQUENCE: 94
MLTTTFALLT AALGVSAHYT LPRVGTGSDW QHVRRADNWQ NNGFVGDVNS EQIRCFQATP    60
AGAQDVYTVQ AGSTVTYHAN PSIYHPGPMQ FYLARVPDGQ DVKSWTGEGA VWFKVYEEQP   120
QFGAQLTWPS NGKSSFEVPI PSCIRAGNYL LRAEHIALHV AQSQGGAQFY ISCAQLQVTG   180
GGSTEPSQKV SFPGAYKSTD PGILININYP VPTSYQNPGP AVFRC                  225

SEQ ID NO: 95            moltype = AA  length = 515
FEATURE                  Location/Qualifiers
source                   1..515
                         mol_type = protein
                         organism = Bacillus thermoaerophilus
```

```
SEQUENCE: 95
AAPFNGTMMQ  YFEWYLPDDG  TLWTKVANEA  NNLSSLGITA  LWLPPAYKGT  SRSDVGYGVY   60
DLYDLGEFNQ  KGTVRTKYGT  KAQYLQAIQA  AHAAGMQVYA  DVVFDHKGGA  DGTEWVDAVE  120
VNPSDRNQEI  SGTYQIQAWT  KFDFPGRGNT  YSSFKWRWYH  FDGVDWDESR  KLSRIYKFRG  180
IGKAWDWEVD  TENGNYDYLM  YADLDMDHPE  VVTELKNWGK  WYVNTTNIDG  FRLDAVKHIK  240
FSFFPDWLSY  VRSQTGKPLF  TVGEYWSYDI  NKLHNYITKT  NGTMSLFDAP  LHNKFYTASK  300
SGGAFDMRTL  MTNTLMKDQP  TLAVTFVDNH  DTEPGQALQS  WVDPWFKPLA  YAFILTRQEG  360
YPCVFYGDYY  GIPQYNIPSL  KSKIDPLLIA  RRDYAYGTQH  DYLDHSDIIG  WTREGVTEKP  420
GSGLAALITD  GPGGSKWMYV  GKQHAGKVFY  DLTGNRSDTV  TINSDGWGEF  KVNGGSVSVW  480
VPRKTTVSTI  ARPITTRPWT  GEFVRWTEPR  LVAWP                               515

SEQ ID NO: 96           moltype = AA  length = 356
FEATURE                 Location/Qualifiers
source                  1..356
                        mol_type = protein
                        organism = Dictyogllomus thermophilum
SEQUENCE: 96
MKKPLGKIVA  STALLISVAF  SSSIASAKEE  AKGMEIPSLK  EVYKDYFTIG  AAVSHLNIYH   60
YENLLKKHFN  SLTPENQMKW  EVIHPKPYVY  DFGPADEIVD  FAMKNGMKVR  GHTLVWHNQT  120
PGWVYAGTKD  EILARLKEHI  KEVVGHYKGK  VYAWDVVNEA  LSDNPNEFLR  RAPWYDICGE  180
EVIEKAFIWA  HEVDPDAKLF  YNDYNLEDPI  KREKAYKLVK  KLKDKGVPIH  GIGIQGHWTL  240
AWPTPKMLED  SIKRFAELGV  EVQVTEFDIS  IYYDRNENNN  FKVPPEDRLE  RQAQLYKEAF  300
EILRKYKGIV  TGVTFWGVAD  DYTWLYFWPV  RGREDYPLLF  DKNHNPKKAF  WEIVKF      356

SEQ ID NO: 97           moltype = AA  length = 203
FEATURE                 Location/Qualifiers
source                  1..203
                        mol_type = protein
                        organism = Dictyogllomus thermophilum
SEQUENCE: 97
QTSITLTSNA  SGTFDGYYYE  LWKDTGNTTM  TVYTQGRFSC  QWSNINNALF  RTGKKYNQNW   60
QSLGTIRITY  SATYNPNGNS  YLCIYGWSTN  PLVEFYIVES  WGNWRPPGAT  SLGQVTIDGG  120
TYDIYRTTRV  NQPSIVGTAT  FDQYWSVRTS  KRTSGTVTVT  DHFRAWANRG  LNLGTIDQIT  180
LCVEGYQSSG  SANITQNTFS  QGS                                             203

SEQ ID NO: 98           moltype = AA  length = 383
FEATURE                 Location/Qualifiers
source                  1..383
                        mol_type = protein
                        organism = Rasomsonia byssochlamydoides
SEQUENCE: 98
DGLNTAAKAI  GKLYFGTATD  NPELSDVAYE  TQLNNTQDFG  QITPANSMKW  DATEPEQNTF   60
TFAAGDQIAD  LAEANGQILR  CHNLVWYNQL  PSWVTGSGSWT  NETLAAMKN  HITNVVTHYK  120
GRCYAWDVVN  EALNDDGTYR  DNVFYQYIGE  AYIPIAFETA  AAADPNVKLY  YNDYNIEYAG  180
VKATAAQNIV  KLVQSYGARI  DGVGLQSHFI  VGETPSTSTQ  ASNMASFTAL  GVEVAITELD  240
IRMQLPETTA  LLTQQSTDYQ  STVQACVNTP  GCVGITLWDW  TDKYSWVPST  FSGYGDACPW  300
DDNYQKKPAY  YGILTALGGS  ASTTTVGTGT  TTTSTATTSS  TGSSGTGVAQ  HWGQCGGIGW  360
TGPTVCASGY  TCTVVNPYYS  QCL                                             383

SEQ ID NO: 99           moltype = AA  length = 385
FEATURE                 Location/Qualifiers
source                  1..385
                        mol_type = protein
                        organism = Talaromyces leycettanus
SEQUENCE: 99
AGLNTAAKAI  GKLYFGTATD  NPELSDSTYM  QETDNTDDFG  QLTPANSMKW  DATEPSQNTF   60
TFTNGDQIAN  LAKSNGQMLR  CHNLVWYNQL  PSWVTGSGSWT  NATLLAAMKN  HITNVVTHYK  120
GQCYAWDVVN  EALNDDGTYR  SNVFYQYIGE  AYIPIAFATA  AAADPNAKLY  YNDYNIEYPG  180
AKATAAQNIV  KMVKAYGAKI  DGVGLQSHFI  VGSTPSQSSQ  QSNMAAFTAL  GVEVAITELD  240
IRMTLPSTSA  LLAQQSTDYQ  STVSACVNTP  KCIGITLWDW  TDKYSWVPNT  FSGQGDACPW  300
DSNYQKKPAY  YGILTALGGS  ASTSTTTTLV  TSTRTSTTTS  TSATSTSTGV  AQHWGQCGGI  360
GWTGPTTCAS  PYTCQELNPY  YYQCL                                           385

SEQ ID NO: 100          moltype = AA  length = 378
FEATURE                 Location/Qualifiers
source                  1..378
                        mol_type = protein
                        organism = Aspergillus fumigatus
SEQUENCE: 100
AGLNTAAKAK  GLKYFGSATD  NPELTDSAYV  AQLSNTDDFG  QITPGNSMKW  DATEPSQNSF   60
SFANGDAVVN  LANKNGQLMR  CHTLVWHSQL  PNWVSSGSWT  NATLLAAMKN  HITNVVTHYK  120
GKCYAWDVVN  EALNEDGTFR  NSVFYQIIGP  AYIPIAFATA  AAADPDVKLY  YNDYNIEYSG  180
AKATAAQNIV  KMIKAYGAKI  DGVGLQAHFI  VGSTPSQSDL  TTVLKGYTAL  GVEVAYTELD  240
IRMQLPSTAA  KLAQQSTDFQ  GVAAACVSTT  GCVGVTIWDW  TDKYSWVPSV  FQGYGAPLPW  300
DENYVKKPAY  DGLMAGLGAS  GSGTTTTTTT  TSTTTGGTDP  TGVAQKWGQC  GGIGWTGPTT  360
CVSGTTCQKL  NDWYSQCL                                                    378

SEQ ID NO: 101          moltype = AA  length = 409
FEATURE                 Location/Qualifiers
```

```
source                         1..409
                               mol_type = protein
                               organism = Talaromyces leycettanus
SEQUENCE: 101
MKFSNVILAA SASSLVLAAP KSKTKRTSAF QWFGANESGA EFGNQNIPGT LGTDYTWPDT    60
STIQTLRNAG MNIFRVPFLM ERLVPNQMTG SPDPTYLADL KSTVNFITGT GAYAVVDPHN   120
YGRYYNNIIT STSDFAAFWT TVASQFASNP RVIFDTNNEY NNMDQTLVLN LNQAAINAIR   180
AAGATSQYIF AEGNSWTGAW TWTSVNDNMK QLTDPSNKLV YEMHQYLDSD GSGTSDQCVN   240
STIGYDRIVS ATQWLQANGK VAFLGEFAGG SNSVCEAAVT GMLDYMEQNS DVWLGAEWWA   300
AGPWWGNYIY SMEPPSGIAY QNYLSILEPY FPGGSYSGGT GSGSGSTTTT ATTTTTKVPP   360
TSTTSSASST GTGVAQHWGQ CGGQGWTGPT TCVSPYTCQE LNPYYYQCL               409

SEQ ID NO: 102                 moltype = AA  length = 334
FEATURE                        Location/Qualifiers
source                         1..334
                               mol_type = protein
                               organism = Penicillium capsulatum
SEQUENCE: 102
MKFSNLVALA AAASSAMALP LTKKHAKRAS SFEWFGSNES GAEFGSGNIP GVYGTDYIFP    60
STSAIQTLIN NGMNIFRVTF MMERLVPNTM TGSFDAEYLS NLTSVVNYIT EAGAHAVIDP   120
HNYGRYYGSI ISSTSDFQTF WKNVAGQFKS NSLVIFDTNN EYHDMDQTLV LNLNQAAING   180
IRAAGATSQY IFVEGNSYTG AWTWADVNDN LKNLTDPQNK IVYEMHQYLD SDGSGTSATC   240
VSTTIGKERV TSATQWLQKN GKVGILGEFA GGVNDQCKTA ITGMLSYLED NSDVWRGAMW   300
WAAGPWWGDY IFSLEPPSGT AYTGMWSTLK SYLA                              334

SEQ ID NO: 103                 moltype = AA  length = 394
FEATURE                        Location/Qualifiers
source                         1..394
                               mol_type = protein
                               organism = Trichophaea saccata
SEQUENCE: 103
MHSFFSLALA VAGLPALINA QQSAWGQCGG VGWTGATTCV SGYYCSKLND YYSQCIPGTA    60
STTTSAVSTT TTATSPTGSV CSGNRTKFKY FGVNESGAEF GNNVVPGTLG KDYTWPTTDS   120
VDFFLGKGMN TFRIAFLMER LSPPAGGLTG TFDPTYLASL KNIASYITGK GGYAIIDPHN   180
YGRYNGNIIT DYTSFGTWCK NLASQFKSDS HIIFDTNNEY HDMDETLVFN LNQACINGIR   240
AAGATSQLIL IEGNSWTGAW TWISSGNAAS LINLTDPNNN IAYEMHQYLD SDGSGTSPTC   300
VSSTIGAERL AAATAWLQAN NKKGFLGEIG AGSNDDCIAA VKGALCSMQE AGGVWLGALW   360
WAAGPWWGDY YQSIEPPDGA AIARILPEAL LPFL                              394

SEQ ID NO: 104                 moltype = AA  length = 294
FEATURE                        Location/Qualifiers
source                         1..294
                               mol_type = protein
                               organism = Sordaria fimicola
SEQUENCE: 104
MRSSTILQTG LVAVLPFAVQ AASGSGKSTR YWDCCKPSCA WSGKASVNRP VLACDANNNP    60
LNDANVKSGC DGGSAYTCAN NSPWAVNDNL AYGFAATKLS GGTESSWCCA CYALTFTSGP   120
VSGKTLVVQS TSTGGDLGSN HFDLNMPGGG VGLFDGCKRE FGGLPGAQYG GISSRSECDS   180
FPPAALKPGCQ WRFDWFKNAD NPEFTFKQVQ CPSELTSRTG CKRNDDSQFP AFTPPSGGGS   240
NPSTPTTPPS SGGGGSGCAA AMYAQCGGSG FSGCTNCPSG STCKAINDYY HQCA         294

SEQ ID NO: 105                 moltype = AA  length = 278
FEATURE                        Location/Qualifiers
source                         1..278
                               mol_type = protein
                               organism = Thielavia terrestris
SEQUENCE: 105
ASGSGQSTRY WDCCKPSCAW PGKAAVSQPV YACDANFQRL SDFNVQSGCN GGSAYSCADQ    60
TPWAVNDNLA YGFAATSIAG GSESSWCCAC YALTFTSGPV AGKTMVVQST STGGDLGSNH   120
FDIAMPGGGV GIFNGCSSQF GGLPGAQYGG ISSRDQCDSF PAPLKPGCQW RFDWFQNADN   180
PTFTFQQVQC PAEIVARSGC KRNDDSSFPV FTPPSGGNGG TGTPTSTAPG SGQTSPGGGS   240
GCTSQKWAQC GGIGFSGCTT CVSGTTCQKL NDYYSQCL                          278

SEQ ID NO: 106                 moltype = AA  length = 595
FEATURE                        Location/Qualifiers
source                         1..595
                               mol_type = protein
                               organism = Penicillium oxalicum
SEQUENCE: 106
RPDPKGGNLT PFIHKEGERS LQGILDNLGG RGKKTPGTAA GLFIASPNTE NPNYYYTWTR    60
DSALTAKCLI DLFEDSRAKF PIDRKYLETG IRDYKSSQAI LQSVSNPSGT LKDGSGLGEP   120
KFEIDLNPFS GAWGRPQRDG PALRATAMIT YANYLISHGQ KSDVSQVMWP IIANDLAYVG   180
QYWNNTGFDL WEEVDGSSFF TIAVQHRALV EGSQLAKKLG CSDCACDSQP PQILCFLQSF   240
WNGKYITSNI NTQASRSGID LDSVLGSIHT FDPEAACDDA TFQPCSARAL ANHKVYVDSF   300
RSIYKINAGL AEGSAANVGR YPEDVYQGGN PWYLATLGAS ELLYDALYQW DRLGKLEVSE   360
TSLSFFKDFD ATVKIGSYSR NSKTYKKLTQ SIKSYADGFI QLVQQYTPSN GSLAEQYDRN   420
TAAPLSANDL TWSFASFLTA TQRRDAVVPP SWGAKSANKV PTTCSASPVV GTYKAPTATF   480
SSKTKCVPAK DIVPITFYLI ENTYYGENVF MSGNITALGN WDAKKGFPLT ANLYTQDQNL   540
WFASVEFIPA GTPFEYKYYK VEPNGDITWE KGPNRVFVAP TGCPVQPHSN DVWQF         595
```

```
SEQ ID NO: 107          moltype = AA  length = 863
FEATURE                 Location/Qualifiers
source                  1..863
                        mol_type = protein
                        organism = Aspergillus fumigatus
SEQUENCE: 107
MRFGWLEVAA LTAASVANAQ ELAFSPPFYP SPWADGQGEW ADAHRRAVEI VSQMTLAEKV    60
NLTTGTGWEM DRCVGQTGSV PRLGINWGLC GQDSPLGIRF SDLNSAFPAG TNVAATWDKT   120
LAYLRGKAMG EEFNDKGVDI LLGPAAGPLG KYPDGGRIWE GFSPDPVLTG VLFAETIKGI   180
QDAGVIATAK HYILNEQEHF RQVGEAQGYG YNITETISSN VDDKTMHELY LWPFADAVRA   240
GVGAVMCSYN QINNSYGCQN SQTLNKLLKA ELGFQGFVMS DWSAHHSGVG AALAGLDMSM   300
PGDISFDDGL SFWGTNLTVS VLNGTVPAWR VDDMAVRIMT AYYKVGRDRL RIPPNFSSWT   360
RDEYGWEHSA VSEGAWTKVN DFVNVQRSHS QIIREIGAAS TVLLKNTGAL PLTGKEVKVG   420
VLGEDAGSNP WGANGCPDRG CDNGTLAMAW GSGTANFPYL VTPEQAIQRE VISNGGNVFA   480
VTDNGALSQM ADVASQSSVS LVFVNADSGE GFISVDGNEG DRKNLTLWKN GEAVIDTVVS   540
HCNNTIVVIH SVGPVLIDRW YDNPNVTAII WAGLPGQESG NSLVDVLYGR VNPSAKTPFT   600
WGKTRESYGA PLLTEPNNGN GAPQDDFNEG VFIDYRHFDK RNETPIYEFG HGLSYTTFGY   660
SHLRVQALNS SSSAYVPTSG ETKPAPTYGE IGSAADYLYP EGLKRITKFI YPWLNSTDLE   720
DSSDDPNYGW EDSEYIPEGA RDGSPQPLLK AGGAPGGNPT LYQDLVRVSA TITNTGNVAG   780
YEVPQLYVSL GGPNEPRVVL RKFDRIFLAP GEQKVWTTTL NRRDLANWDV EAQDVVITKY   840
PKKVHVGSSS RKLPLRAPLP RVY                                          863

SEQ ID NO: 108          moltype = AA  length = 253
FEATURE                 Location/Qualifiers
source                  1..253
                        mol_type = protein
                        organism = Penicillium emersonii
SEQUENCE: 108
MLSSTTRTLA FTGLAGLLSA PLVKAHGFVQ GIVIGDQFYS GYIVNSFPYE SNPPPVIGWA    60
TTATDLGFVD GTGYQGPDII CHRNATPAPL TAPVAAGGTV ELQWTPWPDS HHGPVITYLA   120
PCNGNCSTVD KTTLEFFKID QQGLIDDTSP PGTWASDNLI ANNNSWTVTI PNSVAPGNYV   180
LRHEIIALHS ANNKDGAQNY PQCINIEVTG GGSDAPEGTL GEDLYHDTDP GILVDIYEPI   240
ATYTIPGPPE PTF                                                     253

SEQ ID NO: 109          moltype = AA  length = 532
FEATURE                 Location/Qualifiers
source                  1..532
                        mol_type = protein
                        organism = Aspergillus fumigatus
SEQUENCE: 109
MLASTFSYRM YKTALILAAL LGSGQAQQVG TSQAEVHPSM TWQSCTAGGS CTTNNGKVVI    60
DANWRWVHKV GDYTNCYTGN TWDTTICPDD ATCASNCALE GANYESTYGV TASGNSLRLN   120
FVTTSQQKNI GSRLYMMKDD STYEMFKLLN QEFTFDVDVS NLPCGLNGAL YFVAMDADGG   180
MSKYPTNKAG AKYGTGYCDS QCPRDLKFIN GQANVEGWQP SSNDANAGTG NHGSCCAEMD   240
IWEANSISTA FTPHPCDTPG QVMCTGDACG GTYSSDRYGG TCDPDGCDFN SFRQGNKTFY   300
GPGMTVDTKS KFTVVTQFIT DDGTSSGTLK EIKRFYVQNG KVIPNSESTW TGVSGNSITT   360
EYCTAQKSLF QDQNVFEKHG GLEGMGAALA QGMVLVMSLW DDHSANMLWL DSNYPTTASS   420
TTPGVARGTC DISSGVPADV EANHPDAYVV YSNIKVGPIG STFNSGGSNP GGGTTTTTTT   480
QPTTTTTTAG NPGGTGVAQH YGQCGGIGWT GPTTCASPYT CQKLNDYYSQ CL          532

SEQ ID NO: 110          moltype = AA  length = 454
FEATURE                 Location/Qualifiers
source                  1..454
                        mol_type = protein
                        organism = Aspergillus fumigatus
SEQUENCE: 110
MKHLASSIAL TLLLPAVQAQ QTVWGQCGGQ GWSGPTSCVA GAACSTLNPY YAQCIPGATA    60
TSTTLTTTTA ATTTSQTTTK PTTTGPTTSA PTVTASGNPT SGYQLYANPY YSSEVHTLAM   120
PSLPSSLQPK ASAVAEVPSF VWLDVAAKVP TMGTYLADIQ AKNKAGANPP IAGIFVVYDL   180
PDRDCAALAS NGEYSIANNG VANYKAYIDA IRAQLVKYSD VHTILVIEPD SLANLVTNLN   240
VAKCANAQSA YLECVDYALK QLNLPNVAMY LDAGHAGWLG WPANLGPAAT LFAKVYTDAG   300
SPAAVRGLAT NVANYNAWSL STCPSYTQGD PNCDEKKYIN AMAPLLKEAG FDAHFIMDTS   360
RNGVQPTKQN AWGDWCNVIG TGFGVRPSTN TGDPLQDAFV WIKPGGESDG TSNSTSPRYD   420
AHCGYSDALQ PAPEAGTWFQ AYFEQLLTNA NPSF                              454

SEQ ID NO: 111          moltype = AA  length = 412
FEATURE                 Location/Qualifiers
source                  1..412
                        mol_type = protein
                        organism = Pyrococcus furiosus
SEQUENCE: 111
AELEGLDESA AQVMATYVWN LGYDGSGITI GIIDTGIDAS HPDLQGKVIG WVDFVNGRSY    60
PYDDHGHGTH VASIAAGTGA ASNGKYKGMA PGAKLAGIKV LGADGSGSIS TIIKGVEWAV   120
DNKDKYGIKV INLSLGSSQS SDGTDALSQA VNAAWDAGLV VVVAAGNSGP NKYTIGSPAA   180
ASKVITVGAV DKYDVITSFS SRGPTADGRL KPEVVAPGNW IIAARASGTS MGQPINDYYT   240
AAPGTSMATP HVAGIAALLL QAHPSWTPDK VKTALIETAD IVKPDEIADI AYGARVNAY   300
KAINYDNYAK LVFTGYVANK GSQTHQFVIS GASFVTATLY WDNANSDLDL YLYDPNGNQV   360
DYSYTAYYGF EKVGYYNPTD GTWTIKVVSY SGSANYQVDV VSDGSLSQPG SS           412
```

```
SEQ ID NO: 112            moltype = AA  length = 177
FEATURE                   Location/Qualifiers
source                    1..177
                          mol_type = protein
                          organism = Thermoascus aurantiacus
SEQUENCE: 112
TRISSCSGSR QSALTTALRN AASLANAAAD AAQSGSASKF SEYFKTTSSS TRQTVAARLR    60
AVAREASSSS SGATTYYCDD PYGYCSSNVL AYTLPSYNII ANCDIFYTYL PALTSTCHAQ   120
DQATTALHEF THAPGVYSPG TDDLAYGYQA AMGLSSSQAV MNADTYALYA NAIYLGC     177

SEQ ID NO: 113            moltype = AA  length = 583
FEATURE                   Location/Qualifiers
source                    1..583
                          mol_type = protein
                          organism = Synthetic construct
SEQUENCE: 113
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFGDA SLYHPKCTID YNDQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                   583

SEQ ID NO: 114            moltype = AA  length = 330
FEATURE                   Location/Qualifiers
source                    1..330
                          mol_type = protein
                          organism = Streptomyces coelicolor
SEQUENCE: 114
HGVAMMPGSR TYLCQLDAKT GTGALDPTNP ACQAALDQSG ATALYNWFAV LDSNAGGRGA    60
GYVPDGTLCS AGDRSPYDFS AYNAARSDWP RTHLTSGATI PVEYSNWAAH PGDFRVYLTK   120
PGWSPTSELG WDDLELIQTV TNPPQQGSPG TDGGHYYWDL ALPSGRSDA LIFMQWVRSD   180
SQENFFSCSD VVFDGGNGEV TGIRGSGSTP DPDPTPTPTD PTTPPTHTGS CMAVYSVENS   240
WSGGFQGSVE VMNHGTEPLN GWAVQWQPGG GTTLGGVWNG SLTSGSDGTV TVRNVDHNRV   300
VPPDGSVTFG FTATSTGNDF PVDSIGCVAP                                  330

SEQ ID NO: 115            moltype = AA  length = 362
FEATURE                   Location/Qualifiers
source                    1..362
                          mol_type = protein
                          organism = Synthetic protein
SEQUENCE: 115
MALRSRLVSL AAVLATLLGG LGLSFLWQKD AQAHGVAMMP GSRTYLCQLD AVTGTGALDP    60
TNPACKAALN QSGATALYNW FAVLDSQAGG RGQYVPDGT LCSAGDRSPY DFSAYNAARS   120
DWPRTHLTSG STIKVQYSNW AAHPGDFRVY ITKPGWSPTS QLGWNDLELI QTVTDPPQQG   180
SPGANGGHYY WNLQLPSGRS GDALIFMQWV RSDSKENFFS CSDVVFDGGN GEVTGIRGSG   240
TDPGTDPTPD PTDPTDPPHT GECMAVYSVT NSWSGGFQGS VEVMNHGTSP LNGWAVQWKP   300
GQGTTIGSAW NGTLTKGSDG TVTVRNADHN RVIPPDGSVS FGFTATSSGN NFPVGTIGCV   360
NP                                                                362

SEQ ID NO: 116            moltype = AA  length = 362
FEATURE                   Location/Qualifiers
source                    1..362
                          mol_type = protein
                          organism = Streptomyces sp.
SEQUENCE: 116
MARRSRLISL AAVLATLLGA LGLTALWPGK AEAHGVAMTP GSRTYLCQLD ALSGTGALNP    60
TNPACRDALS QSGANALYNW FAVLDSNAGG RGAGYVPDGT LCSAGDRSPY DFSAYNAARA   120
DWPRTHLTSG ATLKVQYSNW AAHPGDFRVY LTKPGWAPTS ELAWDDLQLV QTVSNPPQQG   180
GAGTNGGHYY WDLALPSGRS GDALMFIQWV RSDSQENFFS CSDIVFDGGN GEVTGIGGTG   240
TPTPTPTPTP TPTPTDPEHS GSCMAVYNVV SSWAGGFQAS VEVMNHGTEP RNGWAVQWKP   300
GSGTQINSVW NGSLSTGSDG TVTVRDVDHN RVIAPDGSVT FGFTATSTGN DYPAGTIGCV   360
TS                                                                362

SEQ ID NO: 117            moltype = AA  length = 364
FEATURE                   Location/Qualifiers
source                    1..364
                          mol_type = protein
                          organism = Synthetic protein
SEQUENCE: 117
MARGKRLLVS LTAVFATLLG GIALTLFGQG NAQAHGVTMT PGSRTYLCWL DAKTSTGSLD    60
PTNPACKAAL SESGSNALYN WFAVLDSNAG GRGAGYVPDG KLCSAGDRSP YNFTGYNAAR   120
SDWPRTHLTA GRTIQVKHSN WAAHPGSFRV YLSKPGYSPS TELGWDDLEL IETVTNPPQT   180
GSPGTDGGHY YWNLDLPSGR SGDAVMFIQW VRSDSQENFF SCSDVVFDGG NGEVTGIRGS   240
```

```
GSTPDPTPTP  TPDPTPTPTD  PHSGCMAVYR  VTNYWSGGFQ  GSVEVMNHST  TARDGWAVKW   300
TPGAGAKVSS  VWNGALTTGS  DGAVTVRSLD  YNRSIPPDGS  VTFGFTATST  GNNLPVGSIG   360
CVNP                                                                    364

SEQ ID NO: 118          moltype = AA   length = 399
FEATURE                 Location/Qualifiers
source                  1..399
                        mol_type = protein
                        organism = Acremonium alcalophilum
SEQUENCE: 118
HMEISWPPPL  RSKYNPFAGG  DIDYSMTSPL  SASGSDFPCK  GSLSLLGSDA  ALPVTSYEAG    60
QTYNMTITGG  AHHNGGSCQA  SLSFDGGNTF  SVIHSYIGGC  PPAGTSSYDF  TIPADAPSAD   120
NAIFAWTWFN  QIGNREMYMN  CAVVSIQGSG  TSTSSLAGRP  EIMIANVGNG  CSTTEGTDVE   180
FPNPGPDVTV  AGSATTPPLG  SCGGGSGGGN  SGGDNGGDGN  RSNPDEGSNP  GVPTIQPDQP   240
AIKPDQPVPE  LPKTTTSLPG  GVFIPLPSEA  PPAERLSTLT  TVTIPTTTAP  PSQPTSSPGE   300
EEACDDVEDG  VEDGVQDDVQ  DGVEDGVEDG  VQDGAQNPGT  ACANEGQWNC  LGGTHFQRCA   360
SGVWSQLMQM  AAGTTCEAGL  SETLIMIRKR  GGARRFLIL                            399

SEQ ID NO: 119          moltype = AA   length = 400
FEATURE                 Location/Qualifiers
source                  1..400
                        mol_type = protein
                        organism = Aspergillus terreus
SEQUENCE: 119
MLLTVLAVVG  CFTAVNGHGY  LTIPASRTRL  GFETGIDTCP  ECSILEPVTA  WPDLEAAQVG    60
RSGPCGYNAR  VSVDYNQPSE  YWGNEPVVTY  TSGEVVEVQW  CVDANGDHGG  MFTYGICQNQ   120
TLVDKFLTPG  YLPTNEEKQA  AEDCFLDGEL  KCTDVSGQTC  GYNPDCTEGA  ACWRNDWFTC   180
NAFQANTARA  CQGVDGASLN  SCKTTIAGGY  TVTKRIKIPD  YSSDHTLLRF  RWNSFQTAQV   240
YLHCADIAIA  GSGGGTTSKS  TTSTTSTTST  SRSTSTSAPT  TTSSASTATP  ICTTQASLIP   300
VTFQEFVTTM  WGENVPVTGS  ISQLGSWSTD  KAVALSATGY  TASNPLWTTT  IDLPAGTTFE   360
YKFIKKETDG  SIIWESDPNR  SYTVPTGCSG  TTATAAASWR                           400

SEQ ID NO: 120          moltype = AA   length = 389
FEATURE                 Location/Qualifiers
source                  1..389
                        mol_type = protein
                        organism = Aspergillus lentulus
SEQUENCE: 120
MIFSILVAAG  CFASAYGHGY  LTIPASRTRL  GFEAGIDTCP  ECSILEPVTA  WPDLEEAQVG    60
RSGPCGYNAR  VSVDYNQPSD  HWGNEPVVTY  TSGEVVEVQW  CVDANGDHGG  MFTYGICQNQ   120
TLVDKFLTPG  YLPTNAEKQA  AEDCFLEGEL  KCTDVSGQTC  GYNPDCTEGK  ACWRNDWFTC   180
NAFQANTARA  CEGVDRAPLN  SCKTTIAGGY  TVTKRIKIPN  YSSNHTLLRF  RWNSFQTAQV   240
YLHCADIAIS  GSGSTTTSTS  TSATTSKTTS  TTSTSTSTST  CTATASLIPV  TFNELVTTTY   300
GENIFITGSI  SQLGSWSTNN  AVALSASRYS  ASNPLWITTI  NLPAGTTFEY  KFIKKETDGS   360
VIWESGPNRS  YTVPTGCSGT  TATATASWR                                       389

SEQ ID NO: 121          moltype = AA   length = 386
FEATURE                 Location/Qualifiers
source                  1..386
                        mol_type = protein
                        organism = Aspergillus lentulus
SEQUENCE: 121
MIFSILVAAG  CFASAYGHGY  LTIPASRTRL  GFEAGIDTCP  ECSILEPVTA  WPDLEEAQVG    60
RSGPCGYNAR  VSVDYNQPSD  HWGNEPVVTY  TSGEVVEVQW  CVDANGDHGG  MFTYGICQNQ   120
TLVDKFLTPG  YLPTNAEKQA  AEDCFLEGEL  KCTDVSGQTC  GYNPDCTEGA  ACWRNDWFTC   180
NAFQANTARA  CEGVDRAPLN  SCKTTIAGGY  TVTKRIKIPN  YSSNHTLLRF  RWNSFQTAQV   240
YLHCADIAIS  GSGSTTTSTS  TSATTSKTTS  TTSTSTSTST  CTATASLIPV  TFNELVTTTY   300
GENIFITGSI  SQLGSWSTNN  AVALSASRYS  ASNPLWITTI  NLPAGTTFEY  KFIKKETDGS   360
VIWESGPNRS  YTVPTGCSGT  TATATA                                          386

SEQ ID NO: 122          moltype = AA   length = 381
FEATURE                 Location/Qualifiers
source                  1..381
                        mol_type = protein
                        organism = Aspergillus fischerianus
SEQUENCE: 122
MIFSILVAAG  CFASAYGHGY  LTIPASRTRL  GFEAGIDTCP  ECSILEPVTA  WPDLEEAQVG    60
RSGPCGYNAR  VSVDYNQPSD  HWGNEPVVTY  TSGEVVEVQW  CVDANGDHGG  MFTYGICQNQ   120
TLVDKFLTPG  YLPTHGEKQA  AEDCFLEGEL  KCTDVSGQTC  GYNPDCTEGA  ACWRNDWFTC   180
NAFQANTARA  CQGVDGAPLN  SCKTTIAGGY  TVTKRIKIPN  YSSNHTLLRF  RWNSFQTAQV   240
YLHCADIAIS  GSGSTTTSTT  TSTTSTSTST  STCTATASLI  PVTFNELVTT  TYGENVFITG   300
SISQLGSWST  DNAVALSASR  YTTSNPLWIT  TINLPAGTTF  QYKFIKKETD  GSVIWESDPN   360
RSYTVPTGCS  GTTATATASW  R                                               381

SEQ ID NO: 123          moltype = AA   length = 385
FEATURE                 Location/Qualifiers
source                  1..385
                        mol_type = protein
                        organism = Aspergillus nidulans
```

-continued

```
SEQUENCE: 123
MKSLLALVAG NLVTAVSGHG YLTVPASRTR LGFEAGIDTC PECSILEPVS AWPDLTAAQV    60
GRSGPCGYNA RVSVDYNQPG DYWGNEPVVS YTAGDVVEVQ WCVDHNGDHG GMFTYGICQN   120
QTLVDLFLTP GYLPTNEEKQ AAEDCFLEGE LSCLHVPGQT CNYNPDCSAG EPCYQNDWFT   180
CNAFQADNNR ACQGVDGAAL NSCMTTIAGG YTVTKKIKIP DYSSSHTLLR FRWNSFQTAQ   240
VYLHCADIAI VGGSGSSPSP TSTTSTATST TTPSSTSCAS AISIPVTFNA LVTTTYGENV   300
YLAGSISQLG SWSTSSAVAL SASKYSSSSP LWTVTVDLPV GATFEYKYIK KESDGSIVWE   360
SGPNRSYTVP TGCSGTTATE SGAWR                                        385

SEQ ID NO: 124         moltype = AA   length = 392
FEATURE                Location/Qualifiers
source                 1..392
                       mol_type = protein
                       organism = Penicillium polonicum
SEQUENCE: 124
MKAFSILTLA GLFSSVNAHG YLTIPSSRTR LGFEAGIDTC PECSILEPVA PWPDLEGPQV    60
GRSGPCGYNA RVSVDYNQPA AHWGNSVVAT YTANQIVDVQ WCVDHNGDHG GMFTYGLCQN   120
QTLVDLFLDP TYLPTNDEKQ AAEDCFLEGE LKCTDVAGQT CGYSPDCTAG QACWRNDWFT   180
CNAFSADSNR GCQGVDGAPL NSCKTTIAGG YTVTKKIKIP DYDSAHTLLR FRWNSFQTGQ   240
VYLNCADIAV AGTGGGSTST TSSATSTTSK TSTITTSTTT TTACATTVTT VPVTFKELVT   300
TSYGQNVFVT GSISQLGSWS TSSAVALSAG SYTTSNPLWT ASIDLPAGTT FEYKFFKKGS   360
DGTITWESEP NRSYTVPTGC SGTTGTASAT WR                                392

SEQ ID NO: 125         moltype = AA   length = 405
FEATURE                Location/Qualifiers
source                 1..405
                       mol_type = protein
                       organism = Penicillium oxalicum
SEQUENCE: 125
MLLSSLLAVP WLASLVTAHG YLTVPFSRTR LGFEAGIDTC PECSILEPVT AWPDVEAAPV    60
GRSGPCGYNA RVGVDYNQPS AHWGQSVVAT YTANQVVEVQ WCVDNNGDHG GMFTYGICRN   120
QTLVDLFTNP NYLPTNAEKQ AAEDCFLDGE LKCTDVTGQT CGYNPDCQPG QPCYRNDWFT   180
CNAFNGDSSG GVRCQGVDA APLNSCKTTI AGGYTVTKKI RIPDYDSKHT LLRFRWNSFQ   240
TAQVYLHCAD IAISGSGSGS GSGSSTTSKT TLTTKATTAT SKTSTTTAAA TTTTTGTCSP   300
ASAVPVTFNE LATTTYGENI YLVGSISQLG SWATSSAIAL SASSYTTSNP LWTTTVNLPA   360
GTSFQYKFIR KKSDGSVVWE SDPNRSYSVP TGCSGIKATA SGTWR                  405

SEQ ID NO: 126         moltype = AA   length = 391
FEATURE                Location/Qualifiers
source                 1..391
                       mol_type = protein
                       organism = Penicillium arizonense
SEQUENCE: 126
MKTTSVLALA GLLTSVNAHG YLTIPSSRTR LGFEAGIDTC PECSILEPVT AWPDVEAAQV    60
GRSGPCGYNA RVSVDYNQPG DYWGNSVVAT YTANDIVEVQ WCVDNNGDHG GMFTYGVCQN   120
QTLVDLFLTP GYLPTTEEKQ AAEDCFLDGE LKCTDVDGQS CGYNPDCTSD QACYRNDWFT   180
CNAFNADSNR GCQGVDGAAL NSCKTTIAGG YTVTKKIKIP DYSSDHTLLR FRWNSFQTAQ   240
VYLHCADIAI SGSGSGSTSS TSSTTSTIAT SATKTSTTAS STTCTAATSV AVTFNELVTT   300
TYGEDVYVVG SISQLGSWST SSAIALSASS YTSSNPLWTA TISLPVGTTF EYKFIKKESD   360
GSIVWESDPN RSYTVPTGCS GTTATASATW R                                 391

SEQ ID NO: 127         moltype = AA   length = 382
FEATURE                Location/Qualifiers
source                 1..382
                       mol_type = protein
                       organism = Mycothermus thermophilus
SEQUENCE: 127
MKFTATGLFM SLPRIVLGHG YLTVPFSRTR LGAEAGIDSC PECSILEPVL AWPNLDAAPV    60
GRSGPCGYNA RVSVDYNQPS SHWGTTPVAT YSPGQIVEVE WCVDHNGDHG GMFSYRICQN   120
QTLVDKFLTP GYLPTEAEKQ EAEDCFEAGL LPCTDVSGQS CEYSPDCTPG QACWRKDWFT   180
CNAFQADSRR ACQGVDNAPR GSCYTSIAGG YPVTKKIRIP NYLSKHTLLS PKWNSYQTGQ   240
IYLSCADIAI IPGSDPTTPT STTSEASATA TPTASCTPVS TVTLTFSERV VTTWGQSIKL   300
VGSIPELGSW NLSAAPTLSS SEYTSTNPVW THTIMLPVGT SFQYKFVRVE ANGAVTWESD   360
PNRLYTVPSG CATSIRVTSE WR                                           382

SEQ ID NO: 128         moltype = AA   length = 381
FEATURE                Location/Qualifiers
source                 1..381
                       mol_type = protein
                       organism = Acremonium sp. XZ1982
SEQUENCE: 128
MKPASFFAHM GLVSSVLGHG YLTIPRSRTR LGAEAGIDTC PECTIREPVT AWPDLDQATV    60
GRSGPCGFNA RVSVDYNQPS ANWGSAPVAT YTRGQTVTVE WCVDNNGDHG GMFTYRICQD   120
QALVDKLLTP GYLPTEAEKE AAERCFQRGT LPCTDVSGQS CGYNPDCQQG QACWRNDWFT   180
CNAFQADSRR GCQGVDAAPL GSCYTSIAGG YRVTKQIKIP DYVSNHTLLS PKWNSFQTPQ   240
IYLSCADIAI TGGTGAPNPG TTTTRMTATP TNTACAAASS VAVTFNQVAT TSPGQTIKLV   300
GSIQQLGSWN PSAAPALSAS QYTSAKPLWS YTVTLAAGST FQYKFVNVQA DGTIRWESDP   360
NRSYTVPRGC DQRVTVESTW R                                            381
```

| SEQ ID NO: 129 | moltype = AA   length = 380 |
| --- | --- |
| FEATURE | Location/Qualifiers |
| source | 1..380 |
| | mol_type = protein |
| | organism = Acrostalagmus luteoalbus |

SEQUENCE: 129

```
MKTSGILSAL SLASSVLGHG YLTIPKSRTR LGQEAGIDTC PECTILEPVH AWPGLDQAVV   60
GRSGPCGYNA RVSVDYNQPG SAWGSAPVVT YSPGQTVTVE WCVDNNGDHG GMFAYRICQD  120
QDIVNKLITP GYLPTEAEKQ EAEDCFEEGT LPCTDVSGQS CGYSPDCQPG QPCWRNDWFT  180
CNAFDAGSRR GCQGVDNAPI GSCYTSIAGG YKVTKQIRIP DYVSEHTLLS FKWNAFQTPQ  240
IYLSCADIRI SSGGNPNPNP TTTSTSAGPS PTDCTVASNV AVTFNQLVNT VPGQTIKIAG  300
SIPQLGNWSP ASAPALSAAQ YTSSRPLWGH TVTLPAGTTF QYKYINVQSD GQVRWESDPN  360
RSYTVPRSCA QSVVVDTTWR                                             380
```

| SEQ ID NO: 130 | moltype = AA   length = 386 |
| --- | --- |
| FEATURE | Location/Qualifiers |
| source | 1..386 |
| | mol_type = protein |
| | organism = Aspergillus insuetus |

SEQUENCE: 130

```
MSPMKTYLLL VASNLLGTAY GHGYLTIPSS RTRLGFEAGI DTCPECSILE PVSAWPDLTA   60
VQVGRSGPCG YNARVSVDYN QPTDAAEGNEP VVTYSAGDII EIQWCVDNNG DHGGMFTYGI  120
CQDQTLVDLF LTPGYIPTNE EKQAAEDCFL EGELSCTDVP GQSCGYNPDC TAGQACYRND  180
WFTCNAFQAS SNRGCQGVDA APLNSCATTI SGGYTVTKKI KIPDYDSAHT LLRFRWNSFQ  240
TAQVYLGCAD IAISGSGGSP TSSSTATSTS TTTSPSSSCA AATSIPVTFD AKVTTSWGEK  300
VYLVGSISQL GSWSTGSAVA LNADKYTSSN PVWSVTLDIP VGTSFEYKYI KKESDGSVVW  360
ESDPNRSYTV PSGCQGAKVN ESGSWR                                      386
```

| SEQ ID NO: 131 | moltype = AA   length = 387 |
| --- | --- |
| FEATURE | Location/Qualifiers |
| source | 1..387 |
| | mol_type = protein |
| | organism = Cladosporium gossypiicola |

SEQUENCE: 131

```
MKTTTLAGLA ASLAATVNAH GYLTIPSSRT SLNFLKGNDT CPECTILEPV TTFPNLDSAL   60
VGRSGPCGYN ARVSTDYNTP GNVWGTSPVA TYSPGQIVDV EWCVDNNGDH GGMFSYRICQ  120
DQQLVNKLIT PGYIPTQAEK QAAEACFEAG TLDCTDVPGQ NCGINPDCQD SACKRTDWFT  180
CNAFQADTRR ACQGVDSSAL GSCKTTIAGG YTVTKKIKIP DYVSEHTLLS FKWNSWQTPQ  240
IYLGCADIAI KGSGTTPPSS TTSKASTTTS TGTTTSSTST ATNCPAKVAV TFSEKRATNY  300
GDTVKVVGSI AELGNWNVQN APSLSATGYT ASNPVWKQTI QLPAGSSFTY KFAIVSSSGA  360
VTWESDPNRS YTVPACQQSA EVSATWR                                     387
```

| SEQ ID NO: 132 | moltype = AA   length = 253 |
| --- | --- |
| FEATURE | Location/Qualifiers |
| source | 1..253 |
| | mol_type = protein |
| | organism = Fusarium sp_75363 |

SEQUENCE: 132

```
MFYSSIITIV TLSTKVYGHG YLSQPMSRTG LNAEAGPDTC PECAILEPVT AWPDLDAAKV   60
GRSGPCGYNA RVSVDYNRPG ANWGKEPVTT YSPGEVIDVQ WCVDNNGDHG GMFTYRICQD  120
QAIVDKFLDP DYIPTEAEKQ EAEDCFEAGI LPCTDVDGQS CEYSPDCTPD QPCWRNDWFT  180
CKSFQGNDDG KGCRGVDDSP INSCYTSIAG GYTVSSKIKI PDYVSEHTLL SFKWNSFQTP  240
QVYLTCADIA IKA                                                    253
```

| SEQ ID NO: 133 | moltype = AA   length = 377 |
| --- | --- |
| FEATURE | Location/Qualifiers |
| source | 1..377 |
| | mol_type = protein |
| | organism = Myrothecium sp. |

SEQUENCE: 133

```
MKTTTIVPFL SLVSQVVGHG YMVIPSSRTR LGAEAKLDSC PECTILEPVS AWPDLDVAQV   60
GRSGPCGYNA RVSIDYNRPS ANWGTKPVAT YTPGQTVDVQ WCVDNNGDHG GMFSWRVCHD  120
QAIVDKLLDP DRTPTDAEKQ AAEDCFEAGL LPCTDVSGQS CGYSPDCTQG QACWRNDWFT  180
CNAFSGDSGK RGCQGVDGSA LGSCYTSIAG GYTVTKKVKM PEIVSNHTLL SLRWNSFQTG  240
QVYLTCADIA ITDSGSGGTP TNPNPPTTTT CAAGASVKVT FNEQVKTVVG DSVRLVGSTA  300
QLGSWDATKG VALSADKYTD AKPLWSATVE MAPGTQFSYK FVKVASGGAV TWESDPNRAY  360
TVPTDCSKAY TLESTWK                                                377
```

| SEQ ID NO: 134 | moltype = AA   length = 388 |
| --- | --- |
| FEATURE | Location/Qualifiers |
| source | 1..388 |
| | mol_type = protein |
| | organism = Paraphoma sp. |

SEQUENCE: 134

```
MRSSVAFLSA FVASVQAHGY LSSPMSRTGL NAQAGADTCP ECTILEPVTA WPDLDSAAVG   60
RSGPCGYNAR VSVDYNQPGP RWGSQPVITY TAGDTDVQW CVDNNGDHGG MFAYRICQNQ  120
ALVDKLLTPG YLPTDAEKQA AEDCFEAGTL KCTDVNGQSC GFNPDCQQGQ ACWRNDWFTC  180
GGFQEGTKCR GVDNAPINSC YTSIAGGYTV TKRIKIPNYA SNHTLLSLKW NSFQTPQIYL  240
TCADIKINGA GGTTPNPPTS SRPATSTTTT SATSSVATGC CATPAATVAV TFNSKTTTVV  300
```

```
GQTIKIAGSI SQLGSWNTAN APALSASAYT SSNPLWSTTI NLPAGTSFEY KFIKVESSGT    360
VTYESGANRA YTVPRDCTGK ATVDTQWK                                      388

SEQ ID NO: 135           moltype = AA  length = 391
FEATURE                  Location/Qualifiers
source                   1..391
                         mol_type = protein
                         organism = Penicillium antarcticum
SEQUENCE: 135
MKTTSVLALA GLLTSVNAHG YLTIPSSRTR LGFEAGIDTC PECSILEPVT AWPDVEAAQV    60
GRSGPCGYNS RVSVDYNQPG DYWGNSVVAT YTANDIVEVQ WCVDNNGDHG GMFTYGVCQN    120
QTLVDLFLTP GYLPTTAEKQ AAEDCFLDGE LKCTDVDGQA CGYNPDCTSD QACYRNDWFT    180
CNAFSADSNR GCQGVDGAAL NSCKTTIAGG YTVTKQIKIP NYSSDHTLLR FRWNSFQTAQ    240
VYLHCADIAI TGSGLASTST TTSTKSTTTT SATKTSTTAS SITCTAATSL AVTFNELVTT    300
TYGENVYVIG SISQLGSWST SSAISLSASS YTSSNPLWTA TISLPVGTTF EYKFIKKDSD    360
GSIVWESDPN RSYTVPTGCS GATATASAIW R                                  391

SEQ ID NO: 136           moltype = AA  length = 387
FEATURE                  Location/Qualifiers
source                   1..387
                         mol_type = protein
                         organism = Penicillium concentricum
SEQUENCE: 136
MKASSILTWA GLLASVNAHG YLTIPSSRTR LGFEAGIDTC PECSILEPVS PWPDLEGPQV    60
GRSGPCGYNA RVSVDYNQPS AHWGDVVATY TANQIVEVQW CVDNNGDHGG MFTYGICQDQ    120
ALVDLFLDPD YLPTNAEKQA AEDCFLKGEL KCTDVAGQDC GYSPDCSPGQ LCWRNDWFTC    180
NAFSADTNRR GCQGVDGAPLN SCKTTIAGGY TVTKKIKIPD YDSAHTLLRF RWNSFQTGQA    240
YLHCADISIG GGSGGGPTTT NTATTLTTTT TKTTTTGACA TPATSVSVTF NELVTTTYGQ    300
NIFLVGSISQ LGSWSTSSAI ALSAGSYTSS NPLWTASVSL PVGTTFTYKF FKKGADGSIT    360
WESDPNRSYT VPAACAGTAV TESTTWR                                       387

SEQ ID NO: 137           moltype = AA  length = 397
FEATURE                  Location/Qualifiers
source                   1..397
                         mol_type = protein
                         organism = Penicillium hoeksii
SEQUENCE: 137
MKAVTILTLA SLLSSVSGHG YLTIPSSRTR LGFEAGIDTC PECSILEPVA AWPDLEEAQV    60
GRSGPCGYNA RVSVDYNQPS DYWGNSVVAT YTADEIVEVQ WCVDNNGDHG GMFTYGICQN    120
QTLVDLFLDP DYLPTTDEKQ AAEDCFLEGE LKCTDVSGQT CGYNPDCTSD EACYRNDWFT    180
CNAFNADTNR ACQGVDGAAE YSCTTTISGG YTVTKKIKIP DYDSDHTLLR LRWNSYQTTQ    240
VYLHCADIAI SGSGSSSSSS SSSSSSTSTS TKASTTLTTT TTSATSTATC TAATTIAVTF    300
NELVTTTYGE NVFIAGSISQ LGSWSTSSAI ALSASSYTSS NPLWTTTISL PVGTTFEYKF    360
IKKETNGSIV WESDPNRSYT VPTGCSGATA TATSTWR                            397

SEQ ID NO: 138           moltype = AA  length = 400
FEATURE                  Location/Qualifiers
source                   1..400
                         mol_type = protein
                         organism = Penicillium paxilli
SEQUENCE: 138
MNTALLLALF GTSSLVDAHG YLTIPSSRTR LGFEAGIDTC PECSILEPVA AWPDLEAAQV    60
GRSGPCGYNA RVSVDYNKPG DYWGNSVVAT YTGGDIVEVE WCVDNNGDHG GMFTYGICQN    120
QTLVDLFLDP DYLPSTDEKQ AAEDCFLDGE LKCTDVDGQT CGYNPDCSSD EACYRNDWFT    180
CNAFSADTNR ACQGVDGAAL NSCTTTIAGG YTVTKKIKIP DYSSDHTLLR FRWNSYQTAQ    240
VYLHCADIAI SGSGSGSSSS SSSSSSRTST STSSASSTTK TTTTSATTTT STCAAASSIS    300
VQFNELVTTT YGENIYISGS ISQLGSWDTS SAIALSSSSY TTSNPLWTTT ISLPVGTSFE    360
YKFIKKESDG SVVWESDPNR SYTVPTGCSG ATSVTASWQ                          400

SEQ ID NO: 139           moltype = AA  length = 390
FEATURE                  Location/Qualifiers
source                   1..390
                         mol_type = protein
                         organism = Penicillium roseopurpureum
SEQUENCE: 139
MKSTTIISLA GLVTWVDAHG YLTIPSSRTR LGFEAGIDTC PECSILEPVT AWPDLEEAQV    60
GRSGPCGYNA RVSVDYNQPG DYWGNSVVAS YTADEIVEVQ WCVDNNGDHG GMFTYGICQN    120
QTLVDLFLTP GYLPTTEEKQ AAEDCFLDGE LKCTDVDGQN CGYSPDCTSD EACYRNDWFT    180
CNAFSASTNR GCQGVDGAAL GSCATTIAGG YTVTKKIKIP NYQSDHTLLR FRWNSYQTAQ    240
VYLHCADIAI AGSGSGSSSS STTTSKSSTT SKTIMTTATT ATCTAAMSLS VVFNELATTT    300
YGENIYLVGS ISQLGSWDTS SAIALSASSY TTSNPLWTGT VTLPVGTSFE YKFIKKETDG    360
SITWESDPDR SYTVPSGCSG ATATVTATWR                                    390

SEQ ID NO: 140           moltype = AA  length = 389
FEATURE                  Location/Qualifiers
source                   1..389
                         mol_type = protein
                         organism = Penicillium samsonianum
SEQUENCE: 140
```

```
MKAVSILTLA GLLSSVNAHG YLTIPSSRTR LGFEAGIDTC PECSILEPVT AWPDLEGPQV    60
GRSGPCGYNA RVSVDYNQPG AHWGNSVVAT YTANQIVEVQ WCVDHNGDHG GMFTYGICQN   120
QTLVDLFLDP NYLPTNAEKQ AAEDCFLEGE LKCTDVPGQT CGYSPDCTSD QPCWRNDWFT   180
CNAFNADSNR GCQGVDGAPL NSCKTTIAGG YTVTKKIKIP EYDSAHTLLR FRWNSFQTAQ   240
AYLHCADIAI GGTGSGSTSA TSSTTSKTST ATTSTTTTTA CATTATTVPV TPKELVTTTY   300
GQNVFVTGSI SQLGSWSTSS AIALSAGSYT TSNPLWTASI DLPAGTTFEY KFFKKGSDGS   360
ITWESDPNRS YTVPTGCSGI TGTASATWR                                    389

SEQ ID NO: 141          moltype = AA   length = 386
FEATURE                 Location/Qualifiers
source                  1..386
                        mol_type = protein
                        organism = Penicillium sclerotiorum
SEQUENCE: 141
MRFAQFLAIS GTVTGVAAHG YLTIPSSRTR LGFEAGVDTC PECSILEPVE SWPDLEAAQV    60
GRSGPCGYNS RVSVDYNQPS DYWGNSVVAT YAAGDTIEVQ WCVDNNGDHG GMFTYGICQN   120
QTLVDLFLDP DYLPTTTEKQ LAEDCFLEGE LKCTDVDGQT CGYNPDCTSD EACYRNDWFT   180
CNAFAASTNR GCEGVDGAAE FSCTTTISGG YTVTKKIKIP NYESDHTLLR FRWNSYQTGQ   240
VYLHCADIAI AESGSGSGAS STISTTATTT TTATTTSTCS AAASVSVTFT ELVTTTYGEN   300
VFIVGSITQL GSWDTSSAVA LSASSYTSSN PLWKTTISLP AGTSFEYKFI KKESDGSIVW   360
EDDPNRTFTV PTGCSGATAT ESATWK                                       386

SEQ ID NO: 142          moltype = AA   length = 392
FEATURE                 Location/Qualifiers
source                  1..392
                        mol_type = protein
                        organism = Penicillium sp-52627
SEQUENCE: 142
MKFTCLLALA GTLATVDAHG YLTIPSSRTR LGFEAGIDTC PECSILEPVE SWPDLEAAQV    60
GRSGPCGYNA RVSVDYNQPG DYWGNSVVAT YTGGDTVEVQ WCVDNNGDHG GMFTYGICQN   120
QTLVDLFLDP DYLPSTDEKQ LAEDCFLEGE LKCTDVDGQT CGYNPDCTSD EACYRNDWFT   180
CNAFAATTNR GCEGVDGAAE YSCTTTISGG YTVTKKIKIP DYESDHTLLR FRWNSYQTGQ   240
IYLHCADIAI SGSGSGSDSS TTSSSTATTS KATSTTSTAT TTSCTAATS ISVTFDELVT    300
TTYGENVYIS GSISQLGSWD TSSAVALSAS SYTSSNPLWM ATISLPVGTS FEYKFIKKET   360
DGSIVWESDP NRSYTVPTGC SGATATVSAT WR                                392

SEQ ID NO: 143          moltype = AA   length = 395
FEATURE                 Location/Qualifiers
source                  1..395
                        mol_type = protein
                        organism = Penicillium sp-54569
SEQUENCE: 143
MKATSILTLA SFLSSVNAHG YLTIPSSRTR LGFEAGIDTC PECSILEPVT AWPDLEEAQV    60
GRSGPCGYNA RVSVDYNQPG DYWGNSVVAT YTADEVVEVQ WCVDNNGDHG GMFTYGICQN   120
QTLVDLFLTP GYLPTTDEKQ AAEDCFLEGE LKCTDVDGQT CGYNPDCTSD EACYRNDWFT   180
CNAFNADSNR ACQGVDGAAE GSCTTTISGG YTVTKKIKIP DYDSDHTLLR FRWNSYQTAQ   240
VYLHCADIAI SGSGSGSTSS SSSSASSTSS TTNTLTTTKS TTTSSATCTA ATTISVTFNE   300
LVTTTYGENI FISGSISQLS SWSTSSAIAL SASSYTSSNP LWTVTISLPV GSTFEYKFIK   360
KETDGSIVWE SDPNRSYTVP AGCSGATATA TATWR                             395

SEQ ID NO: 144          moltype = AA   length = 394
FEATURE                 Location/Qualifiers
source                  1..394
                        mol_type = protein
                        organism = Penicillium sp-72443
SEQUENCE: 144
MKAAFISTLQ CLLTLVNAHG YLTIPSSRTR LGFEAGIDTC PECSILEPVT AWPDLEAAQV    60
GRSGPCGYNA RVSVDYNQPG DYWGNSVVAT YTANDIVEVQ WCVDNNGDHG GMFTYGICQN   120
QTLVDLFLTP GYLPTTEEKQ AAEDCFLEGE LKCTDVSGQT CGYNPDCTSD QACYRTDWFT   180
CNAFNDDTNR ACQGVDGAAL NSCTTTIAGG YTVTKKIKIP DYSSDHTLLR FRWNSYQTAQ   240
VYLHCADIAI SGSGSGSSST LSTGSTSSTA ATSVTKTST TTASTTCISA TTVPVVFDEL    300
VTTTYGENIY ITGSIGQLSS WSTLSAIALS ASSYTSSNPL WTVTIDLPAG TTFEYKFIKK   360
ETDGSIIWES DPNRSYTVPT GCSGLTATAS ATWR                              394

SEQ ID NO: 145          moltype = AA   length = 390
FEATURE                 Location/Qualifiers
source                  1..390
                        mol_type = protein
                        organism = Penicillium steckii
SEQUENCE: 145
MKLKSFAIIL NLVTWANAHG YLTIPSSRTR LGFEAGIDTC PECSILEPVT AWPDLEEAQV    60
GRSGPCGYNA RVSVDYNQPG DYWGNSVVAT YTAGDIVEVQ WCVDNNGDHG GMFTYGICQN   120
QTLVDLFLTP GYLPTNEEKQ AAEDCFLDGE LKCTDVDGQT CGYNPDCASD NYSSDHTLLR   180
CNEFSASSNR GCQGVDGAAL NSCTTTIAGG YTVTKKIKIP NYSSDHTLLR FRWNSYQTAQ   240
VYLHCADIAI SGSGSGTTSS STTKSTTSAT SKTSTTTSQS TTTCTAATSL AVTFTELVTT   300
TYGENVYISG SISQLGSWDT SSAIALSADS YTTSNPLWKT TLNLPVGTTF EYKFIKKETD   360
GTVVWESDPN RSYTVPSGCS GATATATATW                                   390

SEQ ID NO: 146          moltype = AA   length = 389
```

| FEATURE | Location/Qualifiers |  |
|---|---|---|
| source | 1..389 |  |
|  | mol_type = protein |  |
|  | organism = Penicillium viticola |  |

SEQUENCE: 146
```
MKFTNVLAIA GTLTSVAAHG YLTIPSSRTR LGFEAGIDTC PECSILEPVE AWPDLEAAQV   60
GRSGPCYNS RVSVDYNQPS DYWGNSVVAT YSAGDIVEVQ WCVDNNGDHG GMFTYGICQN  120
QTLVDLFLDP DYLPTTAEKQ LAEDCFLEGE LKCTDVDGQT CGYNPDCTSD EACYRNDWFT  180
CNAFAATTNR GCEGVDGAAE FSCTTTISGG YTVTKKIKIP DYDSDHTLLR FRWNSYQTGQ  240
VYLHCADISI GSGSGTTTSS SSTTTTSSTT TQTTATTTTS TCSAAASVSV TFAELVTTTY  300
GENVYIAGSI SQLGSWDTSS AVALSASSYT SSNPLWQATI SLPVGTTFEY KFIKKESDGS  360
IVWESDPNRS YTVPTGCSGA TATVSGTWR                                   389
```

| SEQ ID NO: 147 | moltype = AA  length = 397 |
|---|---|
| FEATURE | Location/Qualifiers |
| source | 1..397 |
|  | mol_type = protein |
|  | organism = Penicillium vulpinum |

SEQUENCE: 147
```
MKTSSILTLA GLLATVNAHG YLTIPSSRTR LGFEAGIDTC PECSILEPVA AWPDLEAAQV   60
GRSGPCGYNA RVSVDYNQPS AHWGNSVVAT YTANDIVEVQ WCVDNNGDHG GMFTYGICQN  120
QTLVDLFLDP NYLPTNAEKQ AAEDCFLDGE LKCTDVSGQT CGYSPDCTFD QPCWRNDWFT  180
CNKFSADTNR GCQGVDGAPL NSCKTTIAGG YTVTKKIKIP DYNSAHTLLR FRWNSFQTAQ  240
AYLHCADIAI GGGSGPGSTS TKTTATTLTA TTSKTTTSTT TTTTTTTTA CATTAVPVAF  300
NELVTTAYGQ NIFLTGSISQ LSSWSTTSAI ALSASSYTSS NPLWTTSLTL PAGTTFEYKF  360
FRKNTDGSIT WESDPNRSYT VPSGCSGTAA TAGGSWR                          397
```

| SEQ ID NO: 148 | moltype = AA  length = 393 |
|---|---|
| FEATURE | Location/Qualifiers |
| source | 1..393 |
|  | mol_type = protein |
|  | organism = Pestalotiopsis sp-71627 |

SEQUENCE: 148
```
MFALPALLFA ASVSGHGYLT IPSSRTRLGF EAGTDTCPEC TILEPVSSWP DLDVAAVGRS   60
GVCGYNARVS VDYNFPASTW GSNTVATYSP GQIVDVQWCV DNNGDHGGMF SYRICQDQSV  120
VDKFLTPGYI PTDAEKQAGE DCFDAGLLPC TDVSGQVCDY SPDCTAGQAC YRNDWFTCNA  180
FGATDRRGCE GVDNAPLNSC KTTIAGGYTV SKQIKIPDYV SNHTLLQFKW NSFQTGQIYI  240
SCADIAISGS GSSPAPAPGT TLTTSKTTAT TTSTKTTTSA ASTSTATCVA AANVAVTFNE  300
VVTTAYGETI KIAGSIAALG SWDPSSAPAL SASAYTTANP LWSRTVSLPA GTAFEYKFVR  360
VSASGAITWE SDPNRSYTVP TCGSTATVGT SWK                              393
```

| SEQ ID NO: 149 | moltype = AA  length = 382 |
|---|---|
| FEATURE | Location/Qualifiers |
| source | 1..382 |
|  | mol_type = protein |
|  | organism = Setophaeosphaeria sp. NN051506 |

SEQUENCE: 149
```
MRSAIGKVIA FVASVNAHGY LTSPMSRTGL NAQSGADTCP ECTILEPVTA WPDLDSAQVG   60
RSGPCGYNAR VSVDYNQPGP RWGSAPVITY TAGDVVDVQW CVDNNGDHGG MFTYRICQDQ  120
ALVDKLITPG YLPTDAEKQA AEDCFERGLL KCTDVSGQTC GYNPDCQSGQ ACWRNDWFTC  180
KGFNEGSKCK GVDGAPLNSC YTSIAGGYTV SSKIKIPNYS SNHTLLSFKW NSFQTGQIYI  240
TCADIKIVGS GGTTPTSSST TTVSTSTATA SATSCATPVS NVAVTFTSKT TTIFGQTIKI  300
AGSIAQLGSW NTANAPALSA DQYTAANPIW RTTISLPAGT SFEYKFIKVE SSGAVTYESG  360
ANRVYTVPNG CAGTASVDTT WK                                          382
```

| SEQ ID NO: 150 | moltype = AA  length = 379 |
|---|---|
| FEATURE | Location/Qualifiers |
| source | 1..379 |
|  | mol_type = protein |
|  | organism = Talaromyces sayulitensis |

SEQUENCE: 150
```
MIVSIIVAAA CFASAYGHGY LTIPASRTRL GFEAGIDICP ECSILEPVTA WPDLETAQVG   60
RSGPCGYNAR VSVDYNQPGE YWGVEPVVTY MSGEVVEVQW CVDANGDHGG MFTYGVCQNQ  120
TLVDKFLTRG YLPTNDEKQA AENCFLEGEL KCTDVSGQTC GYNPDCTAGE ACWRNDWFTC  180
NAFQANTARA CEGVDGAPLN SCKTTIAGGY TVTKKIKIPD YSSNHTLRF RWNSFQTAQV   240
YLHCADIAIS GSGNTTTSTS TSATSTAVSS CTATANLIPV TFRELVTTTW GENIFITGSI  300
SQLGSWSTGN AVALSASQYT ASNPLWITTI DLPAGTTFEY KFIKKESDGS VIWESDPNRS  360
YTVPTGCSST IATAAASWR                                              379
```

| SEQ ID NO: 151 | moltype = AA  length = 383 |
|---|---|
| FEATURE | Location/Qualifiers |
| source | 1..383 |
|  | mol_type = protein |
|  | organism = Trichocladium asperum |

SEQUENCE: 151
```
MKQVTALSLI ALATSVQGHG YMIGPASRTR QGFEAGTDTC PECTILEPVA SWPDLDAAAI   60
GRSGPCGYNA RVSVDYNQPG KAWGNEIVET YAAGDVITVQ WCVDNNGDHG GMFTYRICQD  120
QALVDKFTDP SYLPTDAEKQ AAEDCFNEGI LSCGDVDGQD CSYSPDCSEG AACWRNDWFT  180
CEKFGEGSCK GVDGAALNSC VTTIAGGYTV TKKVKLPDYS SEHTLLSFKW NSFQTGQIYL  240
```

-continued

```
SCADIAITGG SGGGTSPNTT SSLAPVSSTS APPSSSTSSS PQETCDAGTS VPVTFEEVAV    300
PEAGQVIKLV GSISELGSWS PSAAIALARS ANTWSATVNI TAGESFEYKF INVEGSQVWW    360
ESDPNRSFTV PCGASANVTG TWR                                            383
```

PROCESSES FOR REDUCING LACTIC ACID IN A BIOFUEL FERMENTATION SYSTEM AND PROCESSES FOR PRODUCING A FERMENTATION PRODUCT

CROSS-REFERENCE TO RELATED APPLICATIONS

This application is a divisional application of U.S. patent application Ser. No. 17/713,797, filed on Apr. 5, 2022 and granted as U.S. Pat. No. 11,795,481, which is a divisional application of U.S. patent application Ser. No. 16/757,459, filed on Apr. 20, 2020 and granted as U.S. Pat. No. 11,326,187, which is a 35 U.S.C. 371 national application of international application no. PCT/US2018/056656 filed Oct. 19, 2018, which claims priority of U.S. provisional application No. 62/575,852 filed Oct. 23, 2017, the contents of which are fully incorporated herein by reference.

REFERENCE TO A SEQUENCE LISTING

This application contains a Sequence Listing in computer-readable form created on Sep. 12, 2023 as an xml file, 178 kb in size, and named SQ_ST26.xml, which is incorporated herein by reference.

FIELD OF THE INVENTION

The present invention relates to a process for reducing and/or preventing an increase in lactic acid devels (e.g., due to bacterial contamination) in a fermentation product production process, such as especially ethanol production, wherein a lytic polysaccharide monooxygenase is added before or during saccharification and/or fermentation to reduce and/or prevent an increase in lactic acid levels during fermentation.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separates the desired fermentation product, e.g. ethanol, from other liquids and/or solids. The remaining fraction is referred to as "whole stillage". Whole stillage typically contains about 10 to 20% solids. The whole stillage is separated into a solid and a liquid fraction, e.g., by centrifugation. The separated solid fraction is referred to as "wet cake" (or "wet grains") and the separated liquid fraction is referred to as "thin stillage". Wet cake and thin stillage contain about 35 and 7% solids, respectively. Wet cake, with optional additional dewatering, is used as a component in animal feed or is dried to provide "Distillers Dried Grains" (DDG) used as a component in animal feed. Thin stillage is typically evaporated to provide evaporator condensate and syrup or may alternatively be recycled to the slurry tank as "backset". Evaporator condensate may either be forwarded to a methanator before being discharged and/or may be recycled to the slurry tank as "cook water". The syrup may be blended into DDG or added to the wet cake before or during the drying process, which can comprise one or more dryers in sequence, to produce DDGS (Distillers Dried Grain with Solubles). Syrup typically contains about 25 to 35% solids. Oil can also be extracted from the thin stillage and/or syrup as a by-product for use in biodiesel production, as a feed or food additive or product, or other biorenewable products.

Contaminating bacteria and their metabolic end-products, such as lactic acid and/or acetic acid, lead to reduced fermentation yields which lead to considerable economic loss to the producer (see Thomas et al., 2001, J. Applied Microbiology, 90: 819-828). The contaminating bacteria compete with the fermenting organism (e.g., yeast) for sugars in the fermentation medium. The lactic acid and/or acetic acid produced by the unwanted bacteria also negatively impact yeast growth. Therefore, it is desirable to decrease the levels of lactic acid and/or unwanted bacteria that compete with fermenting organisms for sugar.

SUMMARY OF THE INVENTION

The present invention provides a solution to the problem of unwanted bacteria competing for sugar in the fermentation medium and the lactic acid they produce, by providing proving a biological solution to reduce and/or eliminate the lactic acid (e.g., due to bacterial cells) for instance, by adding at least one lytic polysaccharide monoxyenase (LPMO) polypeptide or an enzyme composition comprising a LPMO before or during saccharification and/or fermentation.

In an aspect, the present invention relates to a process for reducing and/or preventing an increase in lactic acid levels in a biofuel fermentation system, the process comprising introducing a lytic polysaccharide monooxygenase (LPMO) polypeptide or an enzyme composition comprising a LPMO polypeptide to a biofuel fermentation system, wherein the fermentation system comprises one or more fermentation vessels, pipes and/or components. In an embodiment, the LPMO polypeptide or enzyme composition comprising the LPMO polypeptide is added at a concentration sufficient to reduce and/or prevent an increase in lactic acid levels in the biofuel fermentation system.

In an embodiment, at least one of the fermentation vessels is a fermentation tank and the LPMO polypeptide or the enzyme composition comprising the LPMO polypeptide is introduced into the propagation or fermentation tank. In an embodiment, at least one of the fermentation vessels is a yeast propagation tank and the LPMO polypeptide or the enzyme composition comprising the LPMO polypeptide is introduced into the yeast propagation tank. In an embodiment, the biofuel is ethanol.

In an aspect the present invention relates to a process for producing a fermentation product from a starch-containing material, the process comprising: a) liquefying a starch-containing material in the presence of an alpha-amylase to form a liquefied mash; b) saccharifying the liquefied mash using a carbohydrate source generating enzyme to produce a fermentable sugar; c) fermenting the sugar using a fermenting organism under conditions suitable to produce the fermentation product, wherein at least one LPMO polypeptide or enzyme composition comprising an LPMO polypeptide is added before or during saccharifying step b) and/or fermenting step c).

In an embodiment, steps b) and c) are carried out simultaneously. In an embodiment, a slurry of the starch containing material is heated to above the gelatinization temperature.

In an embodiment, the at least one LPMO polypeptide or enzyme composition comprising the LPMO polypeptide is added after liquefaction. In an embodiment, the at least one LPMO polypeptide or the enzyme composition comprising the LPMO polypeptide is added before or during saccharification. In an embodiment, the at least one LPMO polypeptide or the enzyme composition comprising the LPMO polypeptide is added before or during fermentation. In an embodiment, the fermenting organism is yeast and the at least one LPMO polypeptide or the enzyme composition comprising the LPMO polypeptide is added before or during yeast propagation. In an embodiment, the LPMO polypeptide or the enzyme composition comprising the LPMO polypeptide is introduced just after liquefaction and before the fermentation tank or propagation tank. In an embodiment, the LPMO polypeptide or the enzyme composition comprising the LPMO polypeptide is introduced at any point of the mash cooling system. In an embodiment, the LPMO polypeptide or the enzyme composition comprising the LPMO polypeptide is added to a heat exchanger. In an embodiment, the LPMO polypeptide or the enzyme composition comprising the LPMO polypeptide is added to a mixing tank.

In an embodiment, the fermentation product is an alcohol, preferably ethanol.

In an embodiment, the bacterial cells are gram-positive bacteria or gram-negative bacteria cells. In an embodiment, the bacterial cells are *Lactobacillus* cells, or cells that produce lactic acid.

In an aspect, the present invention relates to the use of an LPMO polypeptide or enzyme composition comprising an LPMO polypeptide for reducing the levels of lactic acid during fermentation in an ethanol production process.

In an aspect, the present invention relates to the use of an LPMO polypeptide or enzyme composition comprising an LPMO polypeptide for reducing the levels of lactic acid during yeast propagation.

In an embodiment, the LPMO is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

In an embodiment, the LPMO polypeptide is a AA9 polypeptide selected from the group consisting of: i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and vi) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

In an embodiment, the LPMO polypeptide is a AA13 polypeptide selected from the group consisting of: i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; vi) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; vii) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; viii) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ix) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; x) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xi) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xii) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xiii) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xiv) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xv) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xvi) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xvii) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xviii) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xvii) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xix) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xx) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xxi) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; xxii) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and xxiii) the *Trichocladium aspergum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

DESCRIPTION OF THE INVENTION

Figure 1:
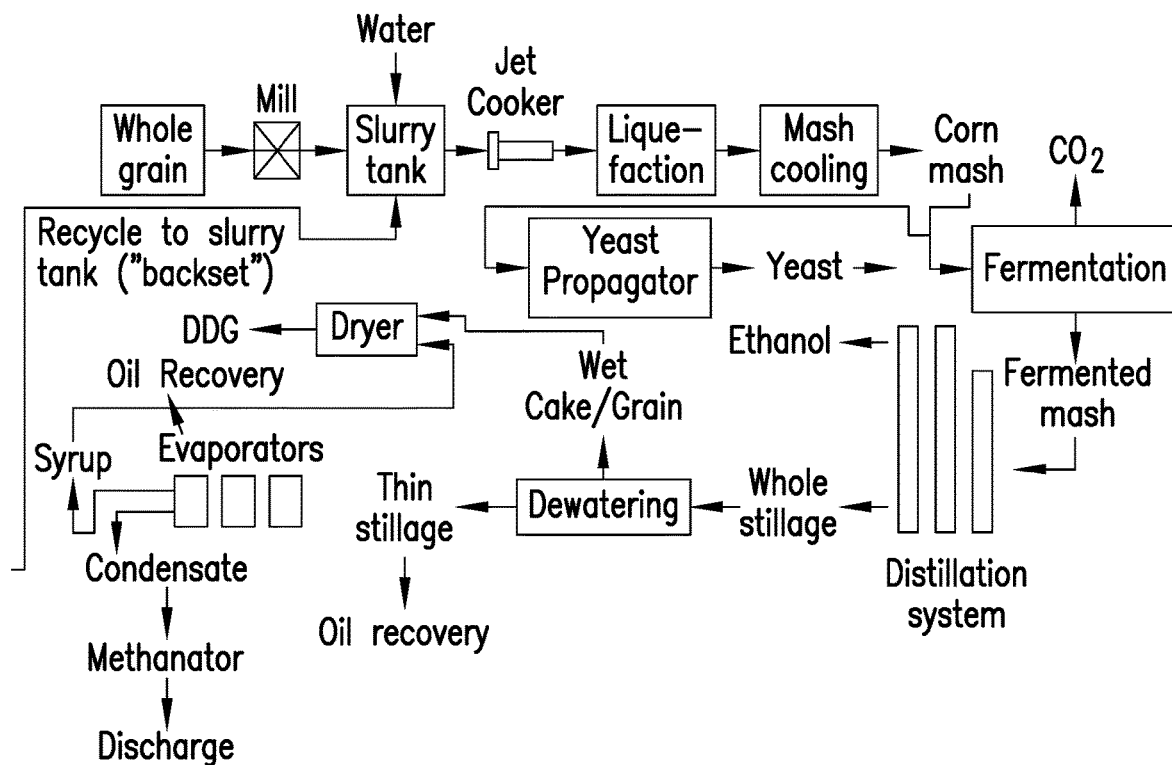
FIG. 1 shows an exemplary dry-grind ethanol production process.

The present invention relates to reducing and/or eliminating bacterial contamination, for instance, in biofuel fermentation systems. The present invention also relates to processes for producing a fermentation product from a starch-containing material using a fermenting organism, wherein at least one lytic polysaccharide monoxyenases (LPMO) is added before and/or during fermentation.

The inventors have surprisingly found that lytic polysaccharide monoxyenases (LPMOs), such as Auxiliary Activity 9 (AA9), are capable of reducing indicator levels of contamination (mainly by lactic acid bacteria) during ethanol fermentation, leading to lower lactic acid titers. Similar results were also demonstrated using certain Auxiliary Activity 13 (AA13) polypeptides. The addition of a LPMO during propagation or fermentation of a contaminated mash also results in increased ethanol yields compared to fermentation of a contaminated mash in the absence of a LPMO. Unexpectedly, LPMOs according to the present disclosure perform equal to or better than antibiotics, such as penicillin, at reducing levels of lactic acid during fermentation.

I. Reducing and/or Eliminating Bacterial Contamination in a Biofuel Fermentation System Accordingly, in an aspect the invention relates to a process for reducing and/or eliminating bacterial contamination in a biofuel fermentation system, the process comprising introducing a lytic polysaccharide monooxygenase (LPMO) polypeptide or an enzyme composition comprising a lytic polysaccharide monooxygenase (LPMO) polypeptide to a biofuel fermentation system. The LPMO polypeptide can be added at a concentration sufficient to inhibit growth of contaminating bacterial cells in the biofuel fermentation system.

The present disclosure contemplates reducing and/or eliminating bacterial contamination due to the presence of variety of types contaminating bacterial cells present in biofuel fermentation systems. In an embodiment, the bacterial cells are gram-positive bacteria or gram-negative bacteria cells. In an embodiment, the contaminating bacterial cells are, but are not limited to, lactic acid and/or acetic acid producing bacteria of the genus *Lactobacillus*, which are known to contaminate fermentation systems. Examples of *Lactobacillus* species that have been found to contaminate fermentation systems include strains of *Lactobacillus collinoides, Lactobacillus brevis, Lactobacillus fermentum, Lactobacillus paracasei, Lactobacillus plantarum*, and/or *Lactobacillus rhamnosus*, and mixtures thereof.

As used herein, the phrase "reducing and/or eliminating bacterial contamination" encompasses the reduction of existing populations of bacterial cells present in the fermentation system, as well as inhibition of bacterial growth. For instance, the LPMO polypeptide or the enzyme composition comprising at least one LPMO polypeptide can reduce the number of bacterial cells present in a fermentation system or inhibit bacterial growth by at least 1%, 3%, 5%, 10%, 11%, 13%, 15%, 17%, 21%, 24%, 26%, 32%, 35%, 40%, 45%, 50%, 54%, 58%, 61%, 63%, 66%, 70%, 75%, 77%, 80%, 85%, 90%, 93%, 95%, 96%, 97%, 98%, 99%, or 100%.

Systems and methods for biofuel fermentation are well known in the art. The fermentation system may include one or more fermentation vessels, pipes, and/or components, which are configured to perform a fermentation product production process, such as the exemplary dry-grind ethanol production process shown in FIG. 1. Those skilled in the art will appreciate that the LPMO polypeptide or enzyme composition comprising the LPMO polypeptide may be introduced into, or prior to, the propagation or fermentation system at a variety of different locations. In an embodiment, at least one of the fermentation vessels in the fermentation system is a fermentation tank and the enzyme composition is introduced into the fermentation tank. In an embodiment, the LPMO polypeptide or enzyme composition comprising the LPMO polypeptide is introduced to the fermentation tank before fermentation begins. In an embodiment, at least one of the fermentation vessels is a yeast propagation tank and the LPMO polypeptide or enzyme composition comprising the LPMO polypeptide is introduced into the yeast propagation tank. In an embodiment, the LPMO polypeptide or enzyme composition comprising the LPMO polypeptide is introduced just after liquefaction and before the fermentation tank or propagation tank. In an embodiment, the LPMO polypeptide or enzyme composition comprising the LPMO polypeptide is introduced at any point of the mash cooling system. In an embodiment, the LPMO polypeptide or enzyme composition comprising the LPMO polypeptide is added to a heat exchanger. In an embodiment, the LPMO polypeptide or enzyme composition comprising the LPMO polypeptide is added to a mixing tank. In an embodiment, the biofuel is an alcohol. In an embodiment, the alcohol is ethanol. In an embodiment, the alcohol is methanol. In an embodiment, the alcohol is butanol.

It is to be understood that any LPMO polypeptide, for instance the LPMO polypeptides described in Section III below, can be used in a composition or process described in this section.

II. Reducing and/or Preventing an Increase in Lactic Acid

In an aspect the invention relates to a process for reducing and/or preventing an increase, in lactic acid in a biofuel fermentation system, the process comprising introducing a LPMO polypeptide or an enzyme composition comprising a lytic polysaccharide monooxygenase (LPMO) polypeptide to a biofuel fermentation system. The LPMO polypeptide or enzyme composition comprising the LPMO polypeptide can be added at a concentration sufficient to reduce and/or prevent an increase in lactic acid in the biofuel fermentation system.

As used herein, the phrase "reducing and/or preventing an increase in lactic acid" encompasses the reduction of existing lactic acid molecules, as well as the addition or build-up of lactic acid molecules in the fermentation system. For instance, an LPMO polypeptide or enzyme composition comprising at least one LPMO can reduce the level of lactic acid in a fermentation system by at least 1%, 3%, 5%, 10%, 11%, 13%, 15%, 17%, 21%, 24%, 26%, 32%, 35%, 40%, 45%, 50%, 54%, 58%, 61%, 63%, 66%, 70%, 75%, 77%, 80%, 85%, 90%, 93%, 95%, 96%, 97%, 98%, 99%, or 100%. In an embodiment, an LPMO polypeptide or enzyme composition comprising at least one LPMO can prevent the increase in the level of lactic acid in a fermentation system by at least 1%, 3%, 5%, 10%, 11%, 13%, 15%, 17%, 21%, 24%, 26%, 32%, 35%, 40%, 45%, 50%, 54%, 58%, 61%, 63%, 66%, 70%, 75%, 77%, 80%, 85%, 90%, 93%, 95%, 96%, 97%, 98%, 99%, or 100% or more.

Systems and methods for biofuel fermentation are well known in the art. The fermentation system may include one or more fermentation vessels, pipes, and/or components, which are configured to perform a fermentation product production process, such as the exemplary dry-grind ethanol production process shown in FIG. 1. Those skilled in the art will appreciate that the LPMO polypeptide or enzyme composition comprising thea LPMO polypeptide may be introduced into the fermentation system at a variety of different locations. In an embodiment, at least one of the fermentation vessels in the fermentation system is a fermentation tank and the LPMO polypeptide or enzyme composition comprising the LPMO polypeptide is introduced into the fermentation tank. In an embodiment, the LPMO polypeptide or enzyme composition comprising the LPMO polypeptide is introduced to the fermentation tank before fermentation begins. In an embodiment, at least one of the fermentation vessels is a yeast propagation tank and the LPMO polypeptide or enzyme composition comprising the LPMO polypeptide is introduced into the yeast propagation tank. In an embodiment, the LPMO polypeptide or enzyme composition comprising the LPMO polypeptide is introduced just after liquefaction and before the fermentation tank or propagation tank In an embodiment, the LPMO polypeptide or enzyme composition comprising the LPMO polypeptide is introduced at any point of the mash cooling system.

In an embodiment, the biofuel is an alcohol. In an embodiment, the alcohol is ethanol. In an embodiment, the alcohol is methanol. In an embodiment, the alcohol is butanol.

It is to be understood that any LPMO polypeptide, for instance the LPMO polypeptides described in Section III below, can be used in a composition or process described in this section.

III. Lytic Polysaccharide Monooxygenases

The present disclosure contemplates processes and compositions comprising any lytic polysaccharide monoxygenases (LPMO) polypeptide that reduces or prevents an increase in lactic acid levels during fermentation and/or reduces the impact of contaminating bacterial cells in a fermentation medium. The term "lytic polysaccharide monooxygenase" or "LPMO" is used synonymously herein with "lytic polyscahharide monooxygenase polypeptide" and "LPMO polypeptide", which refer to an enzyme that oxidizes sp(3) carbons in polysaccharides such as chitin, cellulose, and starch in the presence of an external electron donor and is believed to utilize copper at the active site to activate molecular oxygen. Exemplary LPMOs belong to Auxiliary Activity families AA9, AA10, AA11, and AA13, as defined in the database of carbohydrate active enzymes (http://www.cazy.org/). In an embodiment, the LPMO is selected from the group consisting of Auxiliary Activity 9 (AA9), Auxiliary Activity 10 (AA10), Auxiliary Activity 11 (AA11), Auxiliary Activity 13 (AA13), and combinations thereof.

In an embodiment, the LPMO polypeptide is a AA9 polypeptide. The term "Auxiliary Activity 9 polypeptide" or "AA9 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061). AA9 polypeptides were formerly classified into the glycoside hydrolase Family 61 (GH61) according to Henrissat, 1991, Biochem. J. 280: 309-316, and Henrissat and Bairoch, 1996, Biochem. J. 316: 695-696.

Any AA9 polypeptide can be used as a component of the enzyme composition or used in the processes of the present invention, e.g., bacterial, fungal, archaea, etc.

Examples of AA9 lytic polysaccharide monooxygenases useful in the processes of the present invention include, but are not limited to, AA9 lytic polysaccharide monooxygenases from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290 and WO 2012/149344), *Myceliophthora thermophila* (WO 2009/085935, WO 2009/085859, WO 2009/085864, WO 2009/085868, and WO 2009/033071), *Aspergillus fumigatus* (WO 2010/138754), *Penicillium pinophilum* (WO 2011/005867), *Thermoascus* sp. (WO 2011/039319), *Penicillium* sp. (WO 2011/041397 and WO 2012/000892), *Thermoascus crustaceous* (WO 2011/041504), *Aspergillus aculeatus* (WO 2012/030799), *Thermomyces lanuginosus* (WO 2012/113340, WO 2012/129699, WO 2012/130964, and WO 2012/129699), *Aurantiporus alborubescens* (WO 2012/122477), *Trichophaea saccata* (WO 2012/122477), *Penicillium thomii* (WO 2012/122477), *Talaromyces stipitatus* (WO 2012/135659), *Humicola insolens* (WO 2012/146171), *Malbranchea cinnamomea* (WO 2012/101206), *Talaromyces leycettanus* (WO 2012/101206), *Chaetomium thermophilum* (WO 2012/101206), *Talaromyces thermophilus* (WO 2012/129697 and WO 2012/130950), *Acrophialophora fusispora* (WO 2013/043910), and *Corynascus sepedonium* (WO 2013/043910).

In an embodiment, the AA9 polypeptide is from the genus *Thermoascus*, such as *Thermoascus aurantiacus* or *Thermoascus crustaceus*, for example: the *Thermoascus aurantiacus* AA9 polypeptide of SEQ ID NO: 1, SEQ ID NO: 13, SEQ ID NO: 20, or SEQ ID NO: 22, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Thermoascus crustaceus* AA9 polypeptide of SEQ ID NO: 2, SEQ ID NO: 35, SEQ ID NO: 36, or SEQ ID NO: 37, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Penicillium*, such as *Penicillium emersonii*, for example: the *Penicillium emersonii* AA9 polypeptide of SEQ ID NO: 3 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium pinophilum* AA9 polypeptide of SEQ ID NO: 21, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp. AA9 polypeptide of SEQ ID NO: 23, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Penicillium thomii* AA9 polypeptide of SEQ ID NO: 49, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Thielavia*, such as *Thielavia terrestris*, for example, the *Thielavia terrestris* AA9 polypeptide of SEQ ID NO: 4, SEQ ID NO: 7, SEQ ID NO: 8, SEQ ID NO: 9, SEQ ID NO: 10, SEQ ID NO: 11, SEQ ID NO: 12, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, or SEQ ID NO: 34, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Aspergillus*, such as *Aspergillus fumigatus*, for example: the *Aspergillus fumigatus* AA9 polypeptide of SEQ ID NO: 5 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Aspergillus aculeatus* AA9 polypeptide of SEQ ID NO: 38, SEQ ID NO: 39, SEQ ID NO: 40, SEQ ID NO: 41, SEQ ID NO: 42, SEQ ID NO: 43, or SEQ ID NO: 44, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is the *Penicillium emersonii* AA9 polypeptide of SEQ ID NO: 6 expressed in a *Trichoderma reesei* background, or a variant of SEQ ID NO: 6 having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Trichoderma*, such as *Trichoderma reesei*, for example: the *Trichoderma reesei* AA9 polypeptide of SEQ ID NO: 14 or SEQ ID NO: 84, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Myceliophthora*, such as *Myceliophthora thermophila*, for example: the *Myceliophthora thermophila* AA9 polypeptide of SEQ ID: 15, SEQ ID: 16, SEQ ID: 17, SEQ ID: 18, SEQ ID: 19, SEQ ID: 88, SEQ ID: 93, or SEQ ID: 94, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Aurantiporus*, such as *Aurantiporus alborubescens*, for example, the *Aurantiporus alborubescens* AA9 polypeptide of SEQ ID: 45, or SEQ ID: 46, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Trichophaea*, such as *Trichophaea saccata*, for example, the *Trichophaea saccata* AA9 polypeptide of SEQ ID: 47, or SEQ ID: 48, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Talaromyces*, such as *Talaromyces stipitatus*, for example: the *Talaromyces stipitatus* AA9 polypeptide of SEQ ID: 50, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Talaromyces leycettanus* AA9 polypeptide of SEQ ID NO: 82, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Talaromyces emersonii* AA9 polypeptide of SEQ ID NO: 89, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Talaromyces thermophiles* AA9 polypeptide of SEQ ID NO: 90 or SEQ ID NO: 91, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Thermomyces*, such as *Thermomyces lanuginosus*, for example, the *Thermomyces lanuginosus* AA9 polypeptide of SEQ ID: 52, or SEQ ID: 53, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Humicola*, such as *Humicola insolens*, for example, the *Humicola insolens* AA9 polypeptide of SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO:73, SEQ ID NO: 74, SEQ ID NO: 75, SEQ ID NO: 76, SEQ ID NO:77, SEQ ID NO: 78, SEQ ID NO: 79, or SEQ ID NO: 80, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Malbranchea*, such as *Malbranchea cinnamomea*, for example, the *Malbranchea cinnamomea* AA9 polypeptide of SEQ ID: 81, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Chaetomium*, such as *Chaetomium thermophilum*, for example, the *Chaetomium thermophilum* AA9 polypeptide of SEQ ID: 83, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Acrophialophora*, such as *Acrophialophora fusispora*, for example, the *Acrophialophora fusispora* AA9 polypeptide of SEQ ID: 85, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is from the genus *Corynascus*, such as *Corynascus sepedonium*, for example, the *Corynascus sepedonium* AA9 polypeptide of SEQ ID: 86, or SEQ ID: 87, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA9 polypeptide is a AA9 variant comprising a substitution at one or more positions corresponding to positions 23, 61, 62, 63, 64, 103, 104, 105, 106, 108, 109, 156, 185, 186, and 194 of the full-length polypeptide of SEQ ID NO: 4 herein, wherein the variant reduces and/or eliminates contaminating bacterial cells in a fermentation medium.

In an embodiment, the AA9 variant has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, or 94.

The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 22 to 250 of SEQ ID NO: 4 based on the SignalP program that predicts amino acids 1 to 21 of SEQ ID NO: 4 are a signal peptide. In another aspect, the mature polypeptide is amino acids 20 to 326 of SEQ ID NO: 7 based on the SignalP 3.0 program (Bendtsen et al, 2004, J. Mol. Biol. 340: 783-795) that predicts amino acids 1 to 19 of SEQ ID NO: 7 are a signal peptide. In another aspect, the mature polypeptide is amino acids 18 to 239 of SEQ ID NO: 8 based on the SignalP program that predicts amino acids 1 to 17 of SEQ ID NO: 8 are a signal peptide. In another aspect, the mature polypeptide is amino acids 20 to 258 of SEQ ID NO: 9 based on the SignalP program that predicts amino acids 1 to 19 of SEQ ID NO: 9 are a signal peptide. In another aspect, the mature polypeptide is amino acids 19 to 226 of SEQ ID NO: 10 based on the SignalP program that predicts amino acids 1 to 18 of SEQ ID NO: 10 are a signal peptide. In another aspect, the mature polypeptide is amino acids 20 to 304 of SEQ ID NO: 11 based on the SignalP program that predicts amino acids 1 to 19 of SEQ ID NO: 11 are a signal peptide. In another aspect, the mature polypeptide is amino acids 16 to 317 of SEQ ID NO: 12 based on the SignalP program that predicts amino acids 1 to 15 of SEQ ID NO: 12 are a signal peptide. In another aspect, the mature polypeptide is amino acids 22 to 249 of SEQ ID NO: 13 based on the SignalP program that predicts amino acids 1 to 21 of SEQ ID NO: 13 are a signal peptide. In another aspect, the mature polypeptide is amino acids 20 to 249 of SEQ ID NO: 14 based on the SignalP program that predicts amino acids 1 to 19 of SEQ ID NO: 14 are a signal peptide. In another aspect, the mature polypeptide is amino acids 18 to 232 of SEQ ID NO: 15 based on the SignalP program that predicts amino acids 1 to 17 of SEQ ID NO: 15 are a signal peptide. In another aspect, the mature polypeptide is amino acids 16 to 235 of SEQ ID NO: 16 based on the SignalP program that predicts amino acids 1 to 15 of SEQ ID NO: 16 are a signal peptide. In another aspect, the mature polypeptide is amino acids 19 to 323 of SEQ ID NO: 17 based on the SignalP program that predicts amino acids 1 to 18 of SEQ ID NO: 17 are a signal peptide. In another aspect, the mature polypeptide is amino acids 16 to 310 of SEQ ID NO: 18 based on the SignalP program that predicts amino acids 1 to 15 of SEQ ID NO: 18 are a signal peptide. In another aspect, the mature polypeptide is amino acids 20 to 246 of SEQ ID NO: 19 based on the SignalP program that predicts amino acids 1 to 19 of SEQ ID NO: 19 are a signal peptide. In another aspect, the mature polypeptide is amino acids 22 to 354 of SEQ ID NO: 20 based on the SignalP program that predicts amino acids 1 to 21 of SEQ ID NO: 20 are a signal peptide. In another aspect, the mature polypeptide is amino acids 22 to 322 of SEQ ID NO: 21 based on the SignalP program that predicts amino acids 1 to 21 of SEQ ID NO: 21 are a signal peptide. In another aspect, the mature polypeptide is amino acids 24 to 444 of SEQ ID NO: 22 based on the SignalP program that predicts amino acids 1 to 23 of SEQ ID NO: 22 are a signal peptide. In another aspect, the mature polypeptide is amino acids 26 to 253 of SEQ ID NO: 23 based on the SignalP program that predicts amino acids 1 to 25 of SEQ ID NO: 23 are a signal peptide. In another aspect, the mature polypeptide is amino acids 18 to 246 of SEQ ID NO: 24 based on the SignalP program that predicts amino acids 1 to 17 of SEQ ID NO: 24 are a signal peptide. In another aspect, the mature polypeptide is amino acids 20 to 334 of SEQ ID NO: 25 based on the SignalP program that predicts amino acids 1 to 19 of SEQ ID NO: 25 are a signal peptide. In another aspect, the mature polypeptide is amino acids 18 to 227 of SEQ ID NO: 26 based on the SignalP program that predicts amino acids 1 to 17 of SEQ ID NO: 26 are a signal peptide. In another aspect, the mature polypeptide is amino acids 20 to 223 of SEQ ID NO: 27 based on the SignalP program that predicts amino acids 1 to 19 of SEQ ID NO: 27 are a signal peptide. In another aspect, the mature polypeptide is amino acids 22 to 368 of SEQ ID NO: 28 based on the SignalP program that predicts amino acids 1 to 21 of SEQ ID NO: 28 are a signal peptide. In another aspect, the mature polypeptide is amino acids 25 to 330 of SEQ ID NO: 29 based on the SignalP program that predicts amino acids 1 to 24 of SEQ ID NO: 29 are a signal peptide. In another aspect, the mature polypeptide is amino acids 17 to 236 of SEQ ID NO: 30 based on the SignalP program that predicts amino acids 1 to 16 of SEQ ID NO: 30 are a signal peptide. In another aspect, the mature polypeptide is amino acids 19 to 250 of SEQ ID NO: 31 based on the SignalP program that predicts amino acids 1 to 18 of SEQ ID NO: 31 are a signal peptide. In another aspect, the mature polypeptide is amino acids 23 to 478 of SEQ ID NO: 32 based on the SignalP program that predicts amino acids 1 to 22 of SEQ ID NO: 32 are a signal peptide. In another aspect, the mature polypeptide is amino acids 17 to 230 of SEQ ID NO: 33 based on the SignalP program that predicts amino acids 1 to 16 of SEQ ID NO: 33 are a signal peptide. In another aspect, the mature polypeptide is amino acids 20 to 257 of SEQ ID NO: 34 based on the SignalP program that predicts amino acids 1 to 19 of SEQ ID NO: 34 are a signal peptide. In another aspect, the mature polypeptide is amino acids 23 to 251 of SEQ ID NO: 35 based on the SignalP program that predicts amino acids 1 to 22 of SEQ ID NO: 35 are a signal peptide. In another aspect, the mature polypeptide is amino acids 19 to 349 of SEQ ID NO: 36 based on the SignalP program that predicts amino acids 1 to 18 of SEQ ID NO: 36 are a signal peptide. In another aspect, the mature polypeptide is amino acids 24 to 436 of SEQ ID NO: 37 based on the SignalP program that predicts amino acids 1 to 23 of SEQ ID NO:

37 are a signal peptide. In another aspect, the mature polypeptide is amino acids 21 to 344 of SEQ ID NO: 38 based on the SignalP program that predicts amino acids 1 to 23 of SEQ ID NO: 38 are a signal peptide. In another aspect, the mature polypeptide is amino acids 26 to 400 of SEQ ID NO: 39 based on the SignalP program that predicts amino acids 1 to 25 of SEQ ID NO: 39 are a signal peptide. In another aspect, the mature polypeptide is amino acids 21 to 389 of SEQ ID NO: 40 based on the SignalP program that predicts amino acids 1 to 20 of SEQ ID NO: 40 are a signal peptide. In another aspect, the mature polypeptide is amino acids 22 to 406 of SEQ ID NO: 41 based on the SignalP program that predicts amino acids 1 to 21 of SEQ ID NO: 41 are a signal peptide. In another aspect, the mature polypeptide is amino acids 20 to 427 of SEQ ID NO: 42 based on the SignalP program that predicts amino acids 1 to 19 of SEQ ID NO: 42 are a signal peptide. In another aspect, the mature polypeptide is amino acids 18 to 267 of SEQ ID NO: 43 based on the SignalP program that predicts amino acids 1 to 17 of SEQ ID NO: 43 are a signal peptide. In another aspect, the mature polypeptide is amino acids 21 to 273 of SEQ ID NO: 44 based on the SignalP program that predicts amino acids 1 to 20 of SEQ ID NO: 44 are a signal peptide. In another aspect, the mature polypeptide is amino acids 21 to 322 of SEQ ID NO: 45 based on the SignalP program that predicts amino acids 1 to 20 of SEQ ID NO: 45 are a signal peptide. In another aspect, the mature polypeptide is amino acids 18 to 234 of SEQ ID NO: 46 based on the SignalP program that predicts amino acids 1 to 17 of SEQ ID NO: 46 are a signal peptide. In another aspect, the mature polypeptide is amino acids 24 to 233 of SEQ ID NO: 47 based on the SignalP program that predicts amino acids 1 to 23 of SEQ ID NO: 47 are a signal peptide. In another aspect, the mature polypeptide is amino acids 17 to 237 of SEQ ID NO: 48 based on the SignalP program that predicts amino acids 1 to 16 of SEQ ID NO: 48 are a signal peptide. In another aspect, the mature polypeptide is amino acids 20 to 484 of SEQ ID NO: 49 based on the SignalP program that predicts amino acids 1 to 19 of SEQ ID NO: 49 are a signal peptide. In another aspect, the mature polypeptide is amino acids 22 to 320 of SEQ ID NO: 50 based on the SignalP program that predicts amino acids 1 to 21 of SEQ ID NO: 50 are a signal peptide. In another aspect, the mature polypeptide is amino acids 23 to 272 of SEQ ID NO: 51 based on the SignalP program that predicts amino acids 1 to 22 of SEQ ID NO: 51 are a signal peptide. In another aspect, the mature polypeptide is amino acids 22 to 327 of SEQ ID NO: 52 based on the SignalP program that predicts amino acids 1 to 21 of SEQ ID NO: 52 are a signal peptide. In another aspect, the mature polypeptide is amino acids 23 to 274 of SEQ ID NO: 53 based on the SignalP program that predicts amino acids 1 to 22 of SEQ ID NO: 53 are a signal peptide. In another aspect, the mature polypeptide is amino acids 18 to 227 of SEQ ID NO: 54 based on the SignalP program that predicts amino acids 1 to 17 of SEQ ID NO: 54 are a signal peptide. In another aspect, the mature polypeptide is amino acids 17 to 257 of SEQ ID NO: 55 based on the SignalP program that predicts amino acids 1 to 16 of SEQ ID NO: 55 are a signal peptide. In another aspect, the mature polypeptide is amino acids 20 to 246 of SEQ ID NO: 56 based on the SignalP program that predicts amino acids 1 to 19 of SEQ ID NO: 56 are a signal peptide. In another aspect, the mature polypeptide is amino acids 28 to 265 of SEQ ID NO: 57 based on the SignalP program that predicts amino acids 1 to 27 of SEQ ID NO: 57 are a signal peptide. In another aspect, the mature polypeptide is amino acids 16 to 310 of SEQ ID NO: 58 based on the SignalP program that predicts amino acids 1 to 15 of SEQ ID NO: 58 are a signal peptide. In another aspect, the mature polypeptide is amino acids 21 to 354 of SEQ ID NO: 59 based on the SignalP program that predicts amino acids 1 to 20 of SEQ ID NO: 59 are a signal peptide. In another aspect, the mature polypeptide is amino acids 22 to 267 of SEQ ID NO: 60 based on the SignalP program that predicts amino acids 1 to 21 of SEQ ID NO: 60 are a signal peptide. In another aspect, the mature polypeptide is amino acids 16 to 237 of SEQ ID NO: 61 based on the SignalP program that predicts amino acids 1 to 15 of SEQ ID NO: 61 are a signal peptide. In another aspect, the mature polypeptide is amino acids 20 to 234 of SEQ ID NO: 62 based on the SignalP program that predicts amino acids 1 to 19 of SEQ ID NO: 62 are a signal peptide. In another aspect, the mature polypeptide is amino acids 18 to 226 of SEQ ID NO: 63 based on the SignalP program that predicts amino acids 1 to 17 of SEQ ID NO: 63 are a signal peptide. In another aspect, the mature polypeptide is amino acids 17 to 231 of SEQ ID NO: 64 based on the SignalP program that predicts amino acids 1 to 16 of SEQ ID NO: 64 are a signal peptide. In another aspect, the mature polypeptide is amino acids 22 to 248 of SEQ ID NO: 65 based on the SignalP program that predicts amino acids 1 to 21 of SEQ ID NO: 65 are a signal peptide. In another aspect, the mature polypeptide is amino acids 18 to 233 of SEQ ID NO: 66 based on the SignalP program that predicts amino acids 1 to 17 of SEQ ID NO: 66 are a signal peptide. In another aspect, the mature polypeptide is amino acids 21 to 243 of SEQ ID NO: 67 based on the SignalP program that predicts amino acids 1 to 20 of SEQ ID NO: 67 are a signal peptide. In another aspect, the mature polypeptide is amino acids 21 to 363 of SEQ ID NO: 68 based on the SignalP program that predicts amino acids 1 to 20 of SEQ ID NO: 68 are a signal peptide. In another aspect, the mature polypeptide is amino acids 20 to 296 of SEQ ID NO: 69 based on the SignalP program that predicts amino acids 1 to 19 of SEQ ID NO: 69 are a signal peptide. In another aspect, the mature polypeptide is amino acids 16 to 318 of SEQ ID NO: 70 based on the SignalP program that predicts amino acids 1 to 15 of SEQ ID NO: 70 are a signal peptide. In another aspect, the mature polypeptide is amino acids 19 to 259 of SEQ ID NO: 71 based on the SignalP program that predicts amino acids 1 to 18 of SEQ ID NO: 71 are a signal peptide. In another aspect, the mature polypeptide is amino acids 20 to 325 of SEQ ID NO: 72 based on the SignalP program that predicts amino acids 1 to 19 of SEQ ID NO: 72 are a signal peptide. In another aspect, the mature polypeptide is amino acids 19 to 298 of SEQ ID NO: 74 based on the SignalP program that predicts amino acids 1 to 18 of SEQ ID NO: 74 are a signal peptide. In another aspect, the mature polypeptide is amino acids 20 to 298 of SEQ ID NO: 74 based on the SignalP program that predicts amino acids 1 to 19 of SEQ ID NO: 74 are a signal peptide. In another aspect, the mature polypeptide is amino acids 22 to 344 of SEQ ID NO: 75 based on the SignalP program that predicts amino acids 1 to 21 of SEQ ID NO: 75 are a signal peptide. In another aspect, the mature polypeptide is amino acids 20 to 330 of SEQ ID NO: 76 based on the SignalP program that predicts amino acids 1 to 19 of SEQ ID NO: 76 are a signal peptide. In another aspect, the mature polypeptide is amino acids 19 to 216 of SEQ ID NO: 77 based on the SignalP program that predicts amino acids 1 to 18 of SEQ ID NO: 77 are a signal peptide. In another aspect, the mature polypeptide is amino acids 18 to 490 of SEQ ID NO: 78 based on the SignalP program that predicts amino acids 1 to 17 of SEQ ID NO: 78 are a signal peptide. In another aspect, the mature polypeptide is amino acids 21 to 306 of SEQ ID NO: 79 based on the SignalP program that predicts amino acids 1 to 20 of SEQ ID NO: 79 are a signal peptide. In another aspect, the mature polypeptide is amino acids 22 to 339 of SEQ ID NO: 80 based on the SignalP program that predicts amino acids 1 to 21 of SEQ ID NO: 80 are a signal peptide. In another aspect, the mature polypeptide is amino acids 23 to 334 of SEQ ID NO: 81 based on the SignalP program that predicts amino acids 1 to 22 of SEQ ID NO: 81 are a signal peptide. In another aspect, the mature polypeptide is amino acids 24 to 366 of SEQ ID NO: 82 based on the SignalP program that predicts amino acids 1 to 23 of SEQ ID NO: 82 are a signal peptide. In another aspect, the mature polypeptide is amino acids 21 to 364 of SEQ ID NO: 83 based on the SignalP program that predicts amino acids 1 to 20 of SEQ ID NO: 83 are a signal peptide. In another aspect, the mature polypeptide is amino acids 22 to 344 of SEQ ID NO: 84 based on the SignalP program that predicts amino acids 1 to 21 of SEQ ID NO: 84 are a signal peptide. In another aspect, the mature polypeptide is amino acids 20 to 252 of SEQ ID NO: 85 based on the SignalP program that predicts amino acids 1 to 19 of SEQ ID NO: 85 are a signal peptide. In another aspect, the mature polypeptide is amino acids 20 to 344 of SEQ ID NO: 86 based on the SignalP program that predicts amino acids 1 to 19 of SEQ ID NO: 86 are a signal peptide. In another aspect, the mature polypeptide is amino acids 22 to 347 of SEQ ID NO: 87 based on the SignalP program that predicts amino acids 1 to 21 of SEQ ID NO: 87 are a signal peptide. In another aspect, the mature polypeptide is amino acids 20 to 342 of SEQ ID NO: 88 based on the SignalP program that predicts amino acids 1 to 19 of SEQ ID NO: 88 are a signal peptide. In another aspect, the mature polypeptide is amino acids 27 to 254 of SEQ ID NO: 89 based on the SignalP program that predicts amino acids 1 to 26 of SEQ ID NO: 89 are a signal peptide. In another aspect, the mature polypeptide is amino acids 23 to 272 of SEQ ID NO: 90 based on the SignalP program that predicts amino acids 1 to 22 of SEQ ID NO: 90 are a signal peptide. In another aspect, the mature polypeptide is amino acids 23 to 272 of SEQ ID NO: 91 based on the SignalP program that predicts amino acids 1 to 22 of SEQ ID NO: 91 are a signal peptide. In another aspect, the mature polypeptide is amino acids 19 to 381 of SEQ ID NO: 128 based on the SignalP program that predicts amino acids 1 to 18 of SEQ ID NO: 128 are a signal peptide. In another aspect, the mature polypeptide is amino acids amino acids 22 to 386 of SEQ ID NO: 130 based on the SignalP program that predicts amino acids 1 to 21 of SEQ ID NO: 130 are a signal peptide. In another aspect, the mature polypeptide is amino acids 20 to 387 of SEQ ID NO: 131 based on the SignalP program that predicts amino acids 1 to 19 of SEQ ID NO: 131 are a signal peptide. In another aspect, the mature polypeptide is amino acids 19 to 253 of SEQ ID NO: 132 based on the SignalP program that predicts amino acids 1 to 18 of SEQ ID NO: 132 are a signal peptide. In another aspect, the mature polypeptide is amino acids 19 to 377 of SEQ ID NO: 133 based on the SignalP program that predicts amino acids 1 to 18 of SEQ ID NO: 133 are a signal peptide. In another aspect, the mature polypeptide is amino acids 18 to 388 of SEQ ID NO: 134 based on the SignalP program that predicts amino acids 1 to 17 of SEQ ID NO: 134 are a signal peptide. In another aspect, the mature polypeptide is amino acids 19 to 391 of SEQ ID NO: 135 based on the SignalP program that predicts amino acids 1 to 18 of SEQ ID NO: 135 are a signal peptide. In another aspect, the mature polypeptide is amino acids 19 to 387 of SEQ ID NO: 136 based on the SignalP program that predicts amino acids 1 to 18 of SEQ ID NO: 136 are a signal peptide. In another aspect, the mature polypeptide is amino acids 19 to 390 of SEQ ID NO: 139 based on the SignalP program that predicts amino acids 1 to 18 of SEQ ID NO: 139 are a signal peptide. In another aspect, the mature polypeptide is amino acids 19 to 386 of SEQ ID NO: 141 based on the SignalP program that predicts amino acids 1 to 18 of SEQ ID NO: 141 are a signal peptide. In another aspect, the mature polypeptide is amino acids 19 to 394 of SEQ ID NO: 144 based on the SignalP program that predicts amino acids 1 to 18 of SEQ ID NO: 144 are a signal peptide. In another aspect, the mature polypeptide is amino acids 19 to 391 of SEQ ID NO: 145 based on the SignalP program that predicts amino acids 1 to 18 of SEQ ID NO: 145 are a signal peptide. In another aspect, the mature polypeptide is amino acids 16 to 393 of SEQ ID NO: 148 based on the SignalP program that predicts amino acids 1 to 15 of SEQ ID NO: 148 are a signal peptide. In another aspect, the mature polypeptide is amino acids 18 to 382 of SEQ ID NO: 149 based on the SignalP program that predicts amino acids 1 to 17 of SEQ ID NO: 149 are a signal peptide. In another aspect, the mature polypeptide is amino acids 18 to 379 of SEQ ID NO: 150 based on the SignalP program that predicts amino acids 1 to 17 of SEQ ID NO: 150 are a signal peptide. In another aspect, the mature polypeptide is amino acids 19 to 383 of SEQ ID NO: 151 based on the SignalP program that predicts amino acids 1 to 18 of SEQ ID NO: 151 are a signal peptide. It is known in the art that a host cell may produce a mixture of two of more different mature polypeptides (i.e., with a different C-terminal and/or N-terminal amino acid) expressed by the same polynucleotide.

In an embodiment, the AA9 polypeptide is the mature AA9 polypeptide of any one of SEQ ID NOs: 1-91, or a variant of any of SEQ ID NOs: 1-91 having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the LPMO polypeptide is a AA10 polypeptide. The term "Auxiliary Activity 10 polypeptide" or "AA10 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061). The AA10 may comprise a CBM33 domain comprising a carbohydrate-binding module (CBM), which is defined as a contiguous amino acid sequence within a carbohydrate binding protein with a discreet fold having carbohydrate-binding activity. For example, chitinases are known which contain one or more chitin binding modules in addition to catalytic regions. ChiA of *Serratia marcescens* contains a fibronectin type Ill-type CBM, ChiB of *Serratia marcescens* contains a family 5 CBM and ChiC of *Serratia marcescens* contains a family 12 and a fibronectin type Ill-like CBM. See Bourne and Henrissat, 2001, *Curr. Opin. Struct. Biol.* 11: 593 for domain nomenclature. Likewise, many cellulases contain CBMs that bind to cellulose. Proteins binding to chitin and containing CBMs that stimulate such binding may for example be structural or signaling molecules or they can be enzymes and the overall function of the protein may be determined by domains that are present in addition to the carbohydrate binding module.

Any AA10 polypeptide can be used as a component of the enzyme composition or used in the processes of the present invention, e.g., bacterial, fungal, archaea, etc. AA10 polypeptides of use herein may be identified according to the CAZY classification system (cazy.org/CAZY/fam/acc_CBM.html), which is based on sequence similarities (Davies and Henrissat, 2002, *Biochem Soc T* 30: 291-297 and Bourne and Henrissat, 2001, supra). Proteins in this family are known to bind to chitin, but binding to other polysaccharides, including cellulose, has also been observed (Moser et al., 2008, *Biotechnol. Bioeng.* 100(6):1066-77). For some of these proteins it has been shown that they act synergistically with chitinases and cellulases in the degradation of chitin and cellulose, respectively (Vaaje-Kolstad et al., 2005, *J. Biol. Chem.* 280(31): 28492-7; Vaaje-Kolstad et al., 2009, *FEBS J.* 276(8):2402-15).

AA10 polypeptides contain a family 33 carbohydrate binding module (CBM33). In several cases, the CBM33 module makes up the whole protein, i.e., the protein consists of or consists essentially of a single family 33 CBM, which is in nature synthesized and secreted as such. However some family 33 CBMs may be fused to one or more additional non-catalytic carbohydrate binding modules (e.g., CBM family 2, CBM family 3 and CBM family 5 modules). These proteins are bi- or multi-domain proteins. There is also one known example of a family 33 carbohydrate binding module that is present as an individual module within a much larger catalytic protein. This is the beta-1,4-mannanase protein of *Caldibacillus cellulovorans* (Sunna et al., 2000, *Appl. Environ. Micro.* 66(2): 664-670).

The family 33 CBMs are usually approximately 150-250 amino acids, e.g., 160-240, 170-230, 180-220, 190-210 amino acids in size and have a molecular weight of approximately 20 kDa, preferably 19-21 kDa, 18-21 kDa, 19-22 kDa or 18-20 kDa in size, though CBM33 domains as large as 300-400 amino acids with a molecular weight of approximately 30-40 kDa may also be used. The size of a protein can readily be determined by standard methods that are known in the art.

Preferably, the AA10 polypeptide consists of a single family 33 CBM, or consists essentially of a family 33 CBM. If said AA10 polypeptide "consists essentially of" a family 33 CBM, it is meant that additional amino acids may be present in the protein, in addition to those that make up the family 33 CBM. Preferably there are 1-3, 1-5, 1-10, 10-20, 20-30, 30-40, 40-50, 50-60, 60-70, 70-80, 80-90 or 90-100 or more additional amino acids present. These additional amino acids are in general present C terminal to the family 33 CBM.

Alternatively, the AA10 polypeptide can comprise a family 33 CBM. Additional modules or domains may thus be present in the protein. Examples of such modules are CBM family 2, CBM family 3 and CBM family 5 modules. If additional domains or modules are present, they are in general found C-terminal to the family 33 CBM.

Thus in a preferred aspect, the AA10 polypeptide can contain, consist or consist essentially of a naturally occurring family 33 CBM (or CBM33 family protein) such as CBP21 (or to a homologue thereof from another species) or a biologically active fragment thereof. It can alternatively contain, consist or consist essentially of a variant of a naturally occurring family 33 CBM (or CBM33 family protein) or a biologically active fragment thereof.

AA10 polypeptides which comprise or consist of a family 33 CBM module or the full family 33 CBM protein (which comprises the family 33 CBM module) or its fragments or variants are referred to herein, collectively, as CBM33 proteins or CBM33 family members or proteins. Naturally occurring CBM33 proteins that can be used in the invention include microbial (e.g., bacterial), eukaryotic (e.g., Dictyostelium) or viral CBM33 proteins. Bacterial CBM33 proteins are, however, preferred.

Examples of known CBM33 proteins which may be used in the compositions and methods of the invention and relevant database accession numbers (which are hereby incorporated by reference) are set out in Table 1 of WO 2012/019151 (incorporated herein by reference in its entirety).

Bacterial CBM33 proteins can be from any appropriate source but are preferably from a genus selected from the group consisting of *Bacillus, Chromobacterium, Enterococcus, Francisella, Hahella, Lactobacillus, Lactococcus, Legionella, Listeria, Oceanobacillus, Photobacterium, Photothabdus, Proteus, Pseudoalteromonas, Pseudomonas, Rickettsia, Saccharophagus, Salinvibrio, Serratia, Shewanella, Sodalis, Streptomyces, Thermobifida, Vibrio* and *Yersini* and optionally *Cellulomonas* and *Cellvibrio*.

In an embodiment, the CBM33 protein is a CBP21 as described in U.S. Patent Application No. 2007/0218046 which is incorporated herein by reference. For example the CBP21 of *Serratia marcescens* (SEQ ID NO: 4 in WO2012/019151) may be used. Alternatively, the EfCBM33 of *Enterococcus faecalis* (SEQ ID NO: 5 in WO2012/019151), E7 of *Thermobifida fusca* (SEQ ID NO: 6 in WO2012/019151), CelS2 of *Streptomyces coelicolor* A3(2) (SEQ ID NO: 7 in WO2012/019151), Cfla_0175 of *Cellulomonas flavigena* DSM 20109) (SEQ ID NO: 8 in WO2012/019151), Cfla_0172 of *Cellulomonas flavigena* DSM 20109) (SEQ ID NO: 9), Cfla_0316 of *Cellulomonas flavigena* DSM 20109) (SEQ ID NO: 10 in WO2012/019151), Cfla_0490 of *Cellulomonas flavigena* DSM 20109) (SEQ ID NO: 11 in WO2012/019151), CJA 2191 (Cbp33A) of *Cellvibrio japonicus* Ueda107 (SEQ ID NO: 12 in WO2012/019151), CJA_3139 (Cbp33/10B) of *Cellvibrio japonicus* Ueda107 (SEQ ID NO: 13 in WO2012/019151) and SC01734 of *Streptomyces coelicolar* A3(2)) (SEQ ID NO: 14 in WO2012/019151), may be used. ChbA of *B. amyloliquefaciens* (Chu et al., 2001, Microbiology 147 (Pt 7):1793-803) CHB1, 2 and 3 of *Streptomyces* (Svergun et al., 2000, Biochemistry 39(35):10677-83, Zeltins et al., 1997, *Eur. J. Biochem.* 246(2):557-64, Zeltins et al., 1995, *Anal. Biochem.* 231(2):287-94, Schnellmann et al., 1994, *Mol. Microbiol.* 13(5):807-19; Kolbe et al., 1998, *Microbiology* 144 (Pt 5):1291-7; Saito et al., 2001, *Appl. Environ. Microbiol.* 67(3):1268-73) and CBP1 of *Alteramonas* (Tsujibo et al., 2002, *Appl. Environ. Microbiol.* 68:263-270) are also preferred CBM33 proteins for use in the invention. All of these references are incorporated herein by reference.

The AA10 polypeptides can thus be or correspond to or comprise a naturally occurring CBM33 family protein (such as CBP21, EfCBM33, ChbA, CHB1, 2 and 3 and CBP1 or E7, CelS2, Cfla_0175, Cfla_0172, Cfla_0316, Cfla_0490, CJA_2191 (Cbp33A), CJA_3139 (Cbp33/10B) and SC01734) that it is found in nature or a biologically active fragment thereof. In the alternative the AA10 polypeptide may be a non-native variant.

In an embodiment, the AA10 polypeptide is from the genus *Streptomyces*, such as *Streptomyces coelicolor*, or another *Streptomyces* sp., for example: the *Streptomyces coelicolor* AA10 polypeptide of SEQ ID NO: 114, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Streptomyces* sp. AA10 polypeptide of SEQ ID NO: 115, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA10 polypeptide is the polypeptide of SEQ ID NO: 116, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity thereto. In an embodiment, the AA10 polypeptide is the polypeptide of SEQ ID NO: 116, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but not 100%, sequence identity thereto.

In an embodiment, the AA10 polypeptide is the polypeptide of SEQ ID NO: 117, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity thereto. In an embodiment, the AA10 polypeptide is the polypeptide of SEQ ID NO: 117, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but not 100%, sequence identity thereto.

In an embodiment, the LPMO polypeptide is a AA11 polypeptide. The term "Auxiliary Activity 11 polypeptide" or "AA11 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, *Structure* 20: 1051-1061).

Any AA11 polypeptide can be used as a component of the enzyme composition or used in the processes of the present invention, e.g., bacterial, fungal, archaea, etc. In an embodiment, the AA11 polypeptide is of fungal origin. Exemplary AA11 polypeptides suitable for use in the compositions and processes herein are from the genera *Aspergillus*, such as, *A. niger, A. nidulans, A. terreus, A. clavatus, A. oryzae* or *A. flavus, Neurospora*, such as *N. crassa* or *N. tetrasperma, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces*, and *Myceliophthora*.

In an embodiment, the AA11 polypeptide is from the genus *Acremonium*, such as *Acremonium alcalophilum*, for example the *Acremonium alcalophilum* AA10 polypeptide of SEQ ID NO: 118, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto. In an embodiment, the AA11 polypeptide is the *Acremonium alcalophilum* AA10 polypeptide of SEQ ID NO: 118.

In an embodiment, the LPMO polypeptide is a AA13 polypeptide. The term "Auxiliary Activity 13 polypeptide" or "AA13 polypeptide" means a polypeptide classified as a lytic polysaccharide monooxygenase (Quinlan et al., 2011, Proc. Natl. Acad. Sci. USA 08: 15079-15084; Phillips et al., 2011, ACS Chem. Biol. 6: 1399-1406; Li et al., 2012, Structure 20: 1051-1061).

Any AA13 polypeptide can be used as a component of the enzyme composition or used in the processes of the present invention, e.g., bacterial, fungal, archaea, etc. In an embodiment, the AA13 polypeptide is of fungal origin. Exemplary AA13 polypeptides suitable for use in the compositions and processes herein are from the genera *Aspergillus*, such as, *A. niger, A. nidulans, A. terreus, A. clavatus, A. oryzae* or *A. flavus, Neurospora*, such as *N. crassa* or *N. tetrasperma, Sclerotina, Gibberella, Coniothyrium, Psiticum, Magnaporthe, Podospora, Chaetomium, Phaeosphaeria, Botryotinia, Neosartorya, Pyrenophora, Panicum, Aureococcus, Penicillium, Trichoderma, Sordaria, Colleotrichum, Verticillium, Arthrobotrys, Nectria, Leptosphaeria, Fusarium, Glomerella, Geomyces*, and *Myceliophthora*.

In an embodiment, the AA13 polypeptide is from the genus *Aspergillus*, such as *Aspergillus terreus, Aspergillus lentulus, Aspergillus fischerianus, Aspergillus nidulans, Aspergillus insuetus*, etc., for example: the *Aspergillus terreus* AA13 polypeptide of SEQ ID NO: 119, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Aspergillus lentulus* AA13 polypeptide of SEQ ID NO: 120 or SEQ ID NO: 121, or variants thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Aspergillus fischerianus* AA13 polypeptide of SEQ ID NO: 122, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Aspergillus nidulans* AA13 polypeptide of SEQ ID NO: 123, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Aspergillus insuetus*

AA13 polypeptide of SEQ ID NO: 130, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 22 to 386 of SEQ ID NO: 130 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Penicillium*, such as *Penicillium polonicum*, *Penicillium oxalicum*, *Penicillium arizonense*, etc., for example: the *Penicillium polonicum* AA13 polypeptide of SEQ ID NO: 124 or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium oxalicum* AA13 polypeptide of SEQ ID NO: 125, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium arizonense* AA13 polypeptide of SEQ ID NO: 126, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium antarcticum* AA13 polypeptide of SEQ ID NO: 135, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium concentricum* AA13 polypeptide of SEQ ID NO: 136, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium hoeksii* AA13 polypeptide of SEQ ID NO: 137, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium paxilli* AA13 polypeptide of SEQ ID NO: 138, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium roseopurpureum* AA13 polypeptide of SEQ ID NO: 139, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium samsonianum* AA13 polypeptide of SEQ ID NO: 140, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium sclerotiorum* AA13 polypeptide of SEQ ID NO: 141, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp-52627 AA13 polypeptide of SEQ ID NO: 142, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp-54569 AA13 polypeptide of SEQ ID NO: 143, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium* sp-72443 AA13 polypeptide of SEQ ID NO: 144, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium steckii* AA13 polypeptide of SEQ ID NO: 145, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; the *Penicillium viticola* AA13 polypeptide of SEQ ID NO: 146, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto; or the *Penicillium vulpinum* AA13 polypeptide of SEQ ID NO: 147, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 391 of SEQ ID NO: 135, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 387 of SEQ ID NO: 136, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 390 of SEQ ID NO: 139, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 386 of SEQ ID NO: 141, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 394 of SEQ ID NO: 144, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 391 of SEQ ID NO: 145, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Mycothermus*, such as *Mycothermus thermophilus*, for example, the *Mycothermus thermophilus* AA13 polypeptide of SEQ ID NO: 127, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Acremonium*, such as *Acremonium* sp. XZ1982, for example, the *Acremonium* sp. XZ1982AA13 AA13 polypeptide of SEQ ID NO: 128, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto. In an embodiment, the AA13 polypeptide is amino acids 19 to 381 of SEQ ID NO: 128, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Acrostalagmus*, such as *Acrostalagmus luteoalbus*, for example, the *Acrostalagmus luteoalbus* AA13 polypeptide of SEQ ID NO: 129, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Cladosporium*, such as *Cladosporium gossypiicola*, for example, the *Cladosporium gossypiicola* AA13 polypeptide of SEQ ID NO: 131, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 20 to 387 of SEQ ID NO: 131, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Fusarium*, such as *Fusarium* sp-75363, for example, the *Fusarium* sp-75363 AA13 polypeptide of SEQ ID NO: 132, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 253 of SEQ ID NO: 132, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Myrothecium*, such as *Myrothecium* sp., for example, the *Myrothecium* sp AA13 polypeptide of SEQ ID NO: 133, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 377 of SEQ ID NO: 133, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Paraphoma*, such as *Paraphoma* sp., for example, the *Paraphoma* sp. AA13 polypeptide of SEQ ID NO: 134, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 18 to 388 of SEQ ID NO: 134, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Pestalotiopsis*, such as 15 *Pestalotiopsis* sp-71627, for example, the *Pestalotiopsis* sp-71627 AA13 polypeptide of SEQ ID NO: 148, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 16 to 393 of SEQ ID NO: 148, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Setophaeosphaeria*, such as *Setophaeosphaeria* sp. NN051506, for example, the *Setophaeosphaeria* sp. NN051506AA13 AA13 polypeptide of SEQ ID NO: 149, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 18 to 382 of SEQ ID NO: 149, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Talaromyces*, such as *Talaromyces sayulitensis*, for example, the *Talaromyces sayulitensis* AA13 polypeptide of SEQ ID NO: 150, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 18 to 379 of SEQ ID NO: 150, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is from the genus *Trichocladium*, such as *Trichocladium asperum*, for example, the *Trichocladium asperum* AA13 polypeptide of SEQ ID NO: 151, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

In an embodiment, the AA13 polypeptide is amino acids 19 to 383 of SEQ ID NO: 151, or a variant thereof having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, but less than 100%, sequence identity thereto.

IV. Enzyme Compositions

The present invention also relates to compositions comprising at least one lytic polysaccharide monooxygenase (LPMO) polypeptide of the present invention. Preferably, the compositions are enriched in the at least one LPMO polypeptide of the invention. The term "enriched" indicates that the activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10.

In an embodiment, the composition comprises at least one, at least two, at least three, or at least four LPMO polypeptides of the invention.

The compositions may further comprise multiple enzymatic activities, such as one or more (e.g., several) enzymes selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, glucan 1,4-α-glucosidase, glucan 1,4-alpha-maltohydrolase, glucan 1,4-α-glucosidase, glucan 1,4-alpha-maltohydrolase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In an embodiment, the composition comprises one or more formulating agents as disclosed herein, preferably one or more of the compounds selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

In an embodiment, the composition comprises one or more components selected from the list consisting of vitamins, minerals and amino acids.

IV. Processes for Producing Fermentation Products

The invention also relates to processes for producing a fermentation product from starch-containing material using a fermenting organism, wherein a lytic polysaccharide monooxygenase (LPMO) or an enzyme composition comprising at least one lytic polysaccharide monooxygenase (LPMO) is added before and/or during saccharification and/or fermentation.

Processes for Producing Fermentation Products from Un-Gelatinized Starch-Containing Material In an aspect, the invention relates to processes for producing fermentation products from starch-containing material without gelatinization (i.e., without cooking) of the starch-containing material (often referred to as a "raw starch hydrolysis" process), wherein at least one lytic polysaccharide monooxygenase is added. The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a variant protease of the invention. Saccharification and fermentation may also be separate. Thus in another aspect the invention relates to processes of producing fermentation products, comprising the following steps:

(i) saccharifying a starch-containing material at a temperature below the initial gelatinization temperature using a carbohydrate-source generating enzyme, e.g., a glucoamylase; and (ii) fermenting using a fermentation organism;

wherein step (i) and/or (ii) is carried out using at least a glucoamylase and at least one LPMO polypeptide of the invention or an enzyme composition comprising at least one LPMO polypeptide of the invention. In an embodiment, said at least one LPMO polypeptide or enzyme composition comprising an LPMO polypeptide is added at a concentration sufficient to inhibit growth of contaminating bacterial cells. In an embodiment, said at least one LPMO or enzyme composition comprising at least one LPMO polypeptide is added at a concentration sufficient to reduce the levels of lactic acid during saccharification, fermentation, and/or simultaneous saccharification or fermentation (SSF).

In an embodiment, the at least one LPMO polypeptide or enzyme composition comprising at least one LPMO polypeptide is added during saccharifying step (i). In an embodiment, the at least one LPMO polypeptide or enzyme composition comprising at least one LPMO polypeptide is added during fermenting step (ii).

In one embodiment, an alpha amylase, in particular a fungal alpha-amylase, is also added in step (i). Steps (i) and (ii) may be performed simultaneously. In an embodiment, the at least one LPMO is added during simultaneous saccharification and fermentation (SSF). In an embodiment, the process further includes propagating a fermenting organism under conditions suitable to be further used in fermentation. In an embodiment, the fermenting organism is yeast and the at least one LPMO enzyme composition comprising at least one LPMO polypeptide is added during yeast propagation. In an embodiment, said at least one LPMO or enzyme composition comprising at least one LPMO polypeptide is added at a concentration sufficient to reduce the levels of lactic acid during propagation.

Processes for Producing Fermentation Products from Gelatinized Starch-Containing Material In an aspect, the invention relates to processes for producing fermentation products, especially ethanol, from starch-containing material, which process includes a liquefaction step and sequentially or simultaneously performed saccharification and fermentation steps. Consequently, the invention relates to a process for producing a fermentation product from starch-containing material comprising the steps of:

(a) liquefying starch-containing material in the presence of an alpha-amylase to form a liquefied mash;

(b) saccharifying the liquefied mash using a carbohydrate-source generating enzyme to produce a fermentable sugar; and (c) fermenting the sugar using a fermenting organism under conditions suitable to produce the fermentation product;

wherein at least one LPMO enzyme composition comprising at least one LPMO polypeptide is added before or during saccharifying step (b) and/or fermenting step (c). In an embodiment, said at least one LPMO or enzyme composition comprising at least one LPMO polypeptide is added at a concentration sufficient to inhibit growth of contaminating bacterial cells. In an embodiment, said at least one LPMO or enzyme composition comprising at least one LPMO polypeptide is added at a concentration sufficient to reduce the levels of lactic acid during saccharification, fermentation, and/or simultaneous saccharification or fermentation (SSF).

In an embodiment, the at least one LPMO enzyme composition comprising at least one LPMO polypeptide is added before or during saccharifying step (b). In an embodiment, the at least one LPMO enzyme composition comprising at least one LPMO polypeptide is added before or during fermenting step (c). In one embodiment, an alpha amylase, in particular a fungal alpha-amylase, is also added in step (b). Steps (b) and (c) may be performed simultaneously. In an embodiment, the at least one LPMO enzyme composition comprising at least one LPMO polypeptide is added during simultaneous saccharification and fermentation (SSF). In an embodiment, the process further includes propagating a fermenting organism under conditions suitable to be further used in fermentation. In an embodiment, the fermenting organism is yeast and the at least one LPMO enzyme composition comprising at least one LPMO polypeptide is added before or during yeast propagation. In an embodiment, said at least one LPMO or enzyme composition comprising at least one LPMO polypeptide is added at a concentration sufficient to reduce the levels of lactic acid during propagation.

The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at a pH of 4-6, in particular at a pH of 4.5-5.5, and alpha-amylase variant, optionally together with a hemicellulase, an endoglucanase, a protease, a carbohydrate-source generating enzyme, such as a glucoamylase, a phospholipase, a phytase, and/or pullulanase, are added to initiate liquefaction (thinning). The liquefaction process is usually carried out at a pH of 4-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., in particular 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an embodiment the fermentation product is ethanol.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis*, or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Recovery of Fermentation Products

Subsequent to fermentation or SSF, the fermentation product may be separated from the fermentation medium. The slurry may be distilled to extract the desired fermentation product (e.g., ethanol). Alternatively the desired fermentation product may be extracted from the fermentation medium by micro or membrane filtration techniques. The fermentation product may also be recovered by stripping or other method well known in the art. Typically, the fermentation product, e.g., ethanol, with a purity of up to, e.g., about 96 vol. percent ethanol is obtained.

Thus, in one embodiment, the method of the invention further comprises distillation to obtain the fermentation product, e.g., ethanol. The fermentation and the distillation may be carried out simultaneously and/or separately/sequentially; optionally followed by one or more process steps for further refinement of the fermentation product.

Following the completion of the distillation process, the material remaining is considered the whole stillage. As used herein, the term "whole stillage" includes the material that remains at the end of the distillation process after recovery of the fermentation product, e.g., ethanol. The fermentation product can optionally be recovered by any method known in the art.

Separating (Dewatering) Whole Stillage into Thin Stillage and Wet Cake

In one embodiment, the whole stillage is separated or partitioned into a solid and liquid phase by one or more methods for separating the thin stillage from the wet cake.

Separating whole stillage into thin stillage and wet cake in order to remove a significant portion of the liquid/water, may be done using any suitable separation technique, including centrifugation, pressing and filtration. In a preferred embodiment, the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment, the separation is carried out using other conventional separation equipment such as a plate/frame filter presses, belt filter presses, screw presses, gravity thickeners and deckers, or similar equipment.

Processing of Thin Stillage

Thin stillage is the term used for the supernatant of the centrifugation of the whole stillage. Typically, the thin stillage contains 4-6 percent dry solids (DS) (mainly proteins, soluble fiber, fine fibers, and cell wall components) and has a temperature of about 60-90 degrees centigrade. The thin stillage stream may be condensed by evaporation to provide two process streams including: (i) an evaporator condensate stream comprising condensed water removed from the thin stillage during evaporation, and (ii) a syrup stream, comprising a more concentrated stream of the non-volatile dissolved and non-dissolved solids, such as non-fermentable sugars and oil, remaining present from the thin stillage as the result of removing the evaporated water. Optionally, oil can be removed from the thin stillage or can be removed as an intermediate step to the evaporation process, which is typically carried out using a series of several evaporation stages. Syrup and/or de-oiled syrup may be introduced into a dryer together with the wet grains (from the whole stillage separation step) to provide a product referred to as distillers dried grain with solubles, which also can be used as animal feed.

In an embodiment, syrup and/or de-oiled syrup is sprayed into one or more dryers to combine the syrup and/or de-oiled syrup with the whole stillage to produce distillers dried grain with solubles.

Between 5-90 vol-%, such as between 10-80%, such as between 15-70%, such as between 20-60% of thin stillage (e.g., optionally hydrolyzed) may be recycled (as backset) to step (a). The recycled thin stillage (i.e., backset) may constitute from about 1-70 vol.-%, preferably 15-60% vol.-%, especially from about 30 to 50 vol.-% of the slurry formed in step (a).

In an embodiment, the process further comprises recycling at least a portion of the thin stillage stream treated with a LPMO of the invention to the slurry, optionally after oil has been extracted from the thin stillage stream.

Drying of Wet Cake and Producing Distillers Dried Grains and Distillers Dried Grains with Solubles After the wet cake, containing about 25-40 wt-%, preferably 30-38 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for animals, such as livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS). Partially dried intermediate products, such as are sometimes referred to as modified wet distillers grains, may be produced by partially drying wet cake, optionally with the addition of syrup before, during or after the drying process.

Alpha-Amylase Present and/or Added During Liquefaction

According to the invention an alpha-amylase is present and/or added in liquefaction optionally together with a hemicellulase, an endoglucanase, a protease, a carbohydrate-source generating enzyme, such as a glucoamylase, a phospholipase, a phytase, and/or pullulanase.

The alpha-amylase added during liquefaction step i) may be any alpha-amylase. Preferred are bacterial alpha-amylases, such as especially *Bacillus* alpha-amylases, such as *Bacillus stearothermophilus* alpha-amylases, which are stable at temperature used during liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens*, *Bacillus licheniformis*,

*Bacillus stearothermophilus, Bacillus* sp. TS-23, or *Bacillus subtilis*, but may also be derived from other *Bacillus* sp.

Specific examples of bacterial alpha-amylases include the *Bacillus stearothermophilus* alpha-amylase of SEQ ID NO: 3 in WO 99/19467 or SEQ ID NO: 95 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 and the *Bacillus* sp. TS-23 alpha-amylase disclosed as SEQ ID NO: 1 in WO 2009/061380 (all sequences are hereby incorporated by reference).

In an embodiment the bacterial alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467 and SEQ ID NO: 1 in WO 2009/061380.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 95 herein.

In a preferred embodiment the alpha-amylase is derived from *Bacillus stearothermophilus*. The *Bacillus stearothermophilus* alpha-amylase may be a mature wild-type or a mature variant thereof. The mature *Bacillus stearothermophilus* alpha-amylases, or variant thereof, may be naturally truncated during recombinant production. For instance, the mature *Bacillus stearothermophilus* alpha-amylase may be truncated at the C-terminal so it is around 491 amino acids long (compared to SEQ ID NO: 3 in WO 99/19467 or SEQ ID NO: 95 herein), such as from 480-495 amino acids long.

The *Bacillus* alpha-amylase may also be a variant and/or hybrid. Examples of such a variant can be found in any of WO 96/23873, WO 96/23874, WO 97/41213, WO 99/19467, WO 00/60059, WO 02/10355 and WO2009/061380 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 95 herein or the deletion of amino acids R179 and G180 using SEQ ID NO: 3 in WO 99/19467 or SEQ ID NO: 95 herein. Even more preferred are *Bacillus* alpha-amylases, especially *Bacillus stearothermophilus* (BSG) alpha-amylases, which have at one or two amino acid deletions corresponding to positions R179, G180, 1181 and G182, preferably which have a double deletion corresponding to R179 and G180, or preferably a deletion of positions 181 and 182 (denoted I181*+G182*), and optionally further comprises a N193F substitution (denoted I181*+G182*+N193F) compared to the wild-type BSG alpha-amylase amino acid sequence set forth in SEQ ID NO: 3 disclosed in WO 99/19467 or SEQ ID NO: 95 herein. The bacterial alpha-amylase may also have a substitution in a position corresponding to S239 in the *Bacillus licheniformis* alpha-amylase shown in SEQ ID NO: 4 in WO 99/19467, or a S242 variant in the *Bacillus stearothermophilus* alpha-amylase of SEQ ID NO: 3 in WO 99/19467 or SEQ ID NO: 95 herein.

In an embodiment the variant is a S242A, E or Q variant, preferably a S242Q or A variant, of the *Bacillus stearothermophilus* alpha-amylase (using SEQ ID NO: 95 herein for numbering).

In an embodiment the variant is a position E188 variant, preferably E188P variant of the *Bacillus stearothermophilus* alpha-amylase (using SEQ ID NO: 95 herein for numbering).

Other contemplated variant are *Bacillus* sp. TS-23 variant disclosed in WO2009/061380, especially variants defined in claim 1 of WO2009/061380 (hereby incorporated by reference).

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al., 2002, *The Journal of Biological Chemistry* 277(29): 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

According to the invention the alpha-amylase is used in combination with a hemicellulase, preferably xylanase, having a Melting Point (DSC) above 80° C. Optionally an endoglucanase having a Melting Point (DSC) above 70° C., such as above 75° C., in particular above 80° C. may be included. The thermostable alpha-amylase, such as a bacterial an alpha-amylase, is preferably derived from *Bacillus stearothermophilus* or *Bacillus* sp. TS-23. In an embodiment the alpha-amylase has a T % (min) at pH 4.5, 85° C., 0.12 mM $CaCl_2$ of at least 10.

In an embodiment the alpha-amylase has a T % (min) at pH 4.5, 85° C., 0.12 mM $CaCl_2$, of at least 15.

In an embodiment the alpha-amylase has a T % (min) at pH 4.5, 85° C., 0.12 mM $CaCl_2$, of at least 20.

In an embodiment the alpha-amylase has a T % (min) at pH 4.5, 85° C., 0.12 mM $CaCl_2$, of at least 25.

In an embodiment the alpha-amylase has a T % (min) at pH 4.5, 85° C., 0.12 mM $CaCl_2$, of at least 30.

In an embodiment the alpha-amylase has a T % (min) at pH 4.5, 85° C., 0.12 mM $CaCl_2$, of at least 40.

In an embodiment the alpha-amylase has a T % (min) at pH 4.5, 85° C., 0.12 mM $CaCl_2$, of at least 50.

In an embodiment the alpha-amylase has a T % (min) at pH 4.5, 85° C., 0.12 mM $CaCl_2$, of at least 60.

In an embodiment the alpha-amylase has a T % (min) at pH 4.5, 85° C., 0.12 mM CaCl$_2$, between 10-70.

In an embodiment the alpha-amylase has a T % (min) at pH 4.5, 85° C., 0.12 mM CaCl$_2$, between 15-70.

In an embodiment the alpha-amylase has a T % (min) at pH 4.5, 85° C., 0.12 mM CaCl$_2$, between 20-70.

In an embodiment the alpha-amylase has a T % (min) at pH 4.5, 85° C., 0.12 mM CaCl$_2$, between 25-70.

In an embodiment the alpha-amylase has a T % (min) at pH 4.5, 85° C., 0.12 mM CaCl$_2$, between 30-70.

In an embodiment the alpha-amylase has a T % (min) at pH 4.5, 85° C., 0.12 mM CaCl$_2$, between 40-70.

In an embodiment the alpha-amylase has a T % (min) at pH 4.5, 85° C., 0.12 mM CaCl$_2$, between 50-70.

In an embodiment the alpha-amylase has a T % (min) at pH 4.5, 85° C., 0.12 mM CaCl$_2$, between 60-70.

In an embodiment the alpha-amylase is a bacterial alpha-amylase, preferably derived from the genus *Bacillus*, especially a strain of *Bacillus stearothermophilus*, in particular the *Bacillus stearothermophilus* as disclosed in WO 99/19467 as SEQ ID NO: 3 or SEQ ID NO: 95 herein with one or two amino acids deleted at positions R179, G180, I181 and/or G182, in particular with R179 and G180 deleted, or with I181 and G182 deleted, with mutations in below list of mutations. In preferred embodiments the *Bacillus stearothermophilus* alpha-amylases have double deletion I181+G182, and optional substitution N193F, optionally further comprising mutations selected from below list:

I181*+G182*+N193F+E129V+K177L+R179E+K220P+ N224L+S242Q+Q254S (using SEQ ID NO: 95 herein for numbering).

In an embodiment the bacterial alpha-amylase, such as *Bacillus* alpha-amylase, such as *Bacillus stearomthermphilus* alpha-amylase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 95 herein.

In an embodiment the bacterial alpha-amylase variant, such as *Bacillus* alpha-amylase variant, such as *Bacillus stearomthermphilus* alpha-amylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 95 herein.

It should be understood that when referring to *Bacillus stearothermophilus* alpha-amylase and variants thereof they are normally produced naturally in truncated form. In par-

---

- V59A + Q89R + G112D + E129V + K177L + R179E + K220P + N224L + Q254S;
- V59A + Q89R + E129V + K177L + R179E + H208Y + K220P + N224L + Q254S;
- V59A + Q89R + E129V + K177L + R179E + K220P + N224L + Q254S + D269E + D281N;
- V59A + Q89R + E129V + K177L + R179E + K220P + N224L + Q254S + 1270L;
- V59A + Q89R + E129V + K177L + R179E + K220P + N224L + Q254S + H274K;
- V59A + Q89R + E129V + K177L + R179E + K220P + N224L + Q254S + Y276F;
- V59A + E129V + R157Y + K177L + R179E + K220P + N224L + S242Q + Q254S;
- V59A + E129V + K177L + R179E + H208Y + K220P + N224L + S242Q + Q254S;
- V59A + E129V + K177L + R179E + K220P + N224L + S242Q + Q254S;
- V59A + E129V + K177L + R179E + K220P + N224L + S242Q + Q254S + H274K;
- V59A + E129V + K177L + R179E + K220P + N224L + S242Q + Q254S + Y276F;
- V59A + E129V + K177L + R179E + K220P + N224L + S242Q + Q254S + D281N;
- V59A + E129V + K177L + R179E + K220P + N224L + S242Q + Q254S + M284T;
- V59A + E129V + K177L + R179E + K220P + N224L + S242Q + Q254S + G416V;
- V59A + E129V + K177L + R179E + K220P + N224L + Q254S;
- V59A + E129V + K177L + R179E + K220P + N224L + Q254S + M284T;
- A91L + M961 + E129V + K177L + R179E + K220P + N224L + S242Q + Q254S;
- E129V + K177L + R179E;
- E129V + K177L + R179E + K220P + N224L + S242Q + Q254S;
- E129V + K177L + R179E + K220P + N224L + S242Q + Q254S + Y276F + L427M;
- E129V + K177L + R179E + K220P + N224L + S242Q + Q254S + M284T;
- E129V + K177L + R179E + K220P + N224L + S242Q + Q254S + N376* + 1377*;
- E129V + K177L + R179E + K220P + N224L + Q254S;
- E129V + K177L + R179E + K220P + N224L + Q254S + M284T;
- E129V + K177L + R179E + S242Q;
- E129V + K177L + R179V + K220P + N224L + S242Q + Q254S;
- K220P + N224L + S242Q + Q254S;
- M284V;
- V59A + Q89R + E129V + K177L + R179E + Q254S + M284V.

---

In an embodiment the alpha-amylase is selected from the group of *Bacillus stearomthermphilus* alpha-amylase variants:

I181*+G182*;
I181*+G182*+N193F;
preferably
I181*+G182*+E129V+K177L+R179E;
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A+Q89R+E129V+K177L+ R179E+Q254S+M284V; and ticular, the truncation may be so that the *Bacillus stearothermophilus* alpha-amylase shown in SEQ ID NO: 3 in WO 99/19467 or SEQ ID NO: 95 herein, or variants thereof, are truncated in the C-terminal and are typically around 491 amino acids long, such as from 480-495 amino acids long.

Thermostable Hemicellulase Present and/or Added During Liquefaction

According to the invention an optional hemicellulase, preferably xylanase, having a Melting Point (DSC) above 80° C. is present and/or added to liquefaction step i) in combination with an alpha-amylase, such as a bacterial alpha-amylase (described above).

The thermostability of a hemicellulase, preferably xylanase may be determined as described in the "Materials & Methods"-section under "Determination of $T_d$ by Differential Scanning Calorimetry for Endoglucanases and Hemicellulases".

In an embodiment the hemicellulase, in particular xylanase, especially GH10 or GH11 xylanase has a Melting Point (DSC) above 82° C., such as above 84° C., such as above 86° C., such as above 88° C., such as above 88° C., such as above 90° C., such as above 92° C., such as above 94° C., such as above 96° C., such as above 98° C., such as above 100° C., such as between 80° C. and 110° C., such as between 82° C. and 110° C., such as between 84° C. and 110° C.

In a preferred embodiment the hemicellulase, in particular xylanase, especially GH10 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 96 herein, preferably derived from a strain of the genus Dictyoglomus, such as a strain of Dictyogllomus thermophilum.

In a preferred embodiment the hemicellulase, in particular xylanase, especially GH11 xylanase has at least 60%, such as at least 70%, such as at least 75%, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 97 herein, preferably derived from a strain of the genus Dictyoglomus, such as a strain of Dictyogllomus thermophilum.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 98 herein, preferably derived from a strain of the genus Rasamsonia, such as a strain of Rasomsonia byssochlamydoides.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 99 herein, preferably derived from a strain of the genus Talaromyces, such as a strain of Talaromyces leycettanus.

In a preferred embodiment the hemicellulase, in particular xylanase, especially GH10 xylanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 100 herein, preferably derived from a strain of the genus Aspergillus, such as a strain of Aspergillus fumigatus.

Thermostable Endoglucanase Present and/or Added During Liquefaction

According to the invention an optional endoglucanase ("E") having a Melting Point (DSC) above 70° C., such as between 70° C. and 95° C. may be present and/or added in liquefaction step i) in combination with an alpha-amylase, such as a thermostable bacterial alpha-amylase and an optional hemicellulase, preferably xylanase, having a Melting Point (DSC) above 80° C.

The thermostability of an endoglucanase may be determined as described in the "Materials & Methods"-section of WO 2017/112540 (incorporated herein by reference in its entirety) under the heading "Determination of $T_d$ by Differential Scanning Calorimetry for Endoglucanases and Hemicellulases".

In an embodiment the endoglucanase has a Melting Point (DSC) above 72° C., such as above 74° C., such as above 76° C., such as above 78° C., such as above 80° C., such as above 82° C., such as above 84° C., such as above 86° C., such as above 88° C., such as between 70° C. and 95° C., such as between 76° C. and 94° C., such as between 78° C. and 93° C., such as between 80° C. and 92° C., such as between 82° C. and 91° C., such as between 84° C. and 90° C.

In a preferred embodiment the endogluconase used in a process of the invention or comprised in a composition of the invention is a Glycoside Hydrolase Family 5 endoglucnase or GH5 endoglucanase (see the CAZy database on the "www.cazy.org" webpage.

In an embodiment the GH5 endoglucanase is from family EG II, such as the Talaromyces leycettanus endoglucanase shown in SEQ ID NO: 101 herein; Penicillium capsulatum endoglucanase shown in SEQ ID NO: 102 herein, and Trichophaea saccata endoglucanase shown in SEQ ID NO: 103 herein.

In an embodiment the endoglucanase is a family GH45 endoglucanase. In an embodiment the GH45 endoglucanase is from family EG V, such as the Sordaria fimicola shown in SEQ ID NO: 104 herein or the Thielavia terrestris endoglucanase shown in SEQ ID NO: 105 herein.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 101 herein. In an embodiment the endoglucanase is derived from a strain of the genus Talaromyces, such as a strain of Talaromyces leycettanus.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 102 herein, preferably derived from a strain of the genus *Penicillium*, such as a strain of *Penicillium capsulatum*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 103 herein, preferably derived from a strain of the genus *Trichophaea*, such as a strain of *Trichophaea saccata*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 104 herein, preferably derived from a strain of the genus *Sordaria*, such as a strain of *Sordaria fimicola*.

In an embodiment the endoglucanase has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, such as 100% identity to the mature part of the polypeptide of SEQ ID NO: 105 herein, preferably derived from a strain of the genus *Thielavia*, such as a strain of *Thielavia terrestris*.

In an embodiment the endoglucanase is added in liquefaction step i) at a dose from 1-10,000 µg EP (Enzymes Protein)/g DS), such as 10-1,000 µg EP/g DS.

Carbohydrate-Source Generating Enzyme Present and/or Added During Liquefaction

According to the invention an optional carbohydrate-source generating enzyme, in particular a glucoamylase, preferably a thermostable glucoamylase, may be present and/or added in liquefaction together with an alpha-amylase and optional hemicellulase, preferably xylanase, having a Melting Point (DSC) above 80° C., and an optional endoglucanase having a Melting Point (DSC) above 70° C., and an optional a pullulanase and/or optional phytase.

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is thermostable. The carbohydrate-source generating enzyme, in particular thermostable glucoamylase, may be added together with or separately from the alpha-amylase and the thermostable protease.

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 106 herein.

In an embodiment the thermostable glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NOs: 106 herein.

In an embodiment the carbohydrate-source generating enzyme, in particular thermostable glucoamylase, is the *Penicillium oxalicum* glucoamylase shown in SEQ ID NO: 106 herein.

In a preferred embodiment the carbohydrate-source generating enzyme is a variant of the *Penicillium oxalicum* glucoamylase disclosed as SEQ ID NO: 2 in WO 2011/127802 and shown in SEQ ID NO: 106 herein, having a K79V substitution (referred to as "PE001") (using the mature sequence shown in SEQ ID NO: 14 for numbering). The K79V glucoamylase variant has reduced sensitivity to protease degradation relative to the parent as disclosed in WO 2013/036526 (which is hereby incorporated by reference).

Contemplated *Penicillium oxalicum* glucoamylase variants are disclosed in WO 2013/053801 (which is hereby incorporated by reference).

In an embodiment these variants have reduced sensitivity to protease degradation.

In an embodiment these variant have improved thermostability compared to the parent.

More specifically, in an embodiment the glucoamylase has a K79V substitution (using SEQ ID NO: 106 herein for numbering), corresponding to the PE001 variant, and further comprises at least one of the following substitutions or combination of substitutions: T65A; Q327F; E501V; Y504T; Y504*; T65A+Q327F; T65A+E501V; T65A+Y504T; T65A+Y504*; Q327F+E501V; Q327F+Y504T; Q327F+Y504*; E501V+Y504T; E501V+Y504*; T65A+Q327F+E501V; T65A+Q327F+Y504T; T65A+E501V+Y504T; Q327F+E501V+Y504T; T65A+Q327F+Y504*; T65A+E501V+Y504*; Q327F+E501V+Y504*; T65A+Q327F+E501V+Y504T; T65A+Q327F+E501V+Y504*; E501V+Y504T; T65A+K161S; T65A+Q405T; T65A+Q327W; T65A+Q327F; T65A+Q327Y; P11F+T65A+Q327F; R1K+D3W+K5Q+G7V+N8S+T10K+P11S+T65A+Q327F; P2N+P4S+P11F+T65A+Q327F; P11F+D26C+K33C+T65A+Q327F; P2N+P4S+P11F+T65A+Q327W+E501V+Y504T; R1E+D3N+P4G+G6R+G7A+N8A+T10D+P11D+T65A+Q327F; P11F+T65A+Q327W; P2N+P4S+P11F+T65A+Q327F+E501V+Y504T; P11F+T65A+Q327W+E501V+Y504T; T65A+Q327F+E501V+Y504T; T65A+S105P+Q327W; T65A+S105P+Q327F; T65A+Q327W+S364P; T65A+Q327F+S364P; T65A+S103N+Q327F; P2N+P4S+P11F+K34Y+T65A+Q327F; P2N+P4S+P11F+T65A+Q327F+D445N+V447S; P2N+P4S+P11F+T65A+I172V+Q327F; P2N+P4S+P11F+T65A+Q327F+N502*; P2N+P4S+P11F+T65A+Q327F+N502T+P563S+K571E; P2N+P4S+P11F+R31S+K33V+T65A+Q327F+N564D+K571S; P2N+P4S+P11F+T65A+

Q327F+S377T; P2N+P4S+P11F+T65A+V325T+Q327W; P2N+P4S+P11F+T65A+Q327F+D445N+V447S+E501V+Y504T; P2N+P4S+P11F+T65A+I172V+Q327F+E501V+Y504T; P2N+P4S+P11F+T65A+Q327F+S377T+E501V+Y504T; P2N+P4S+P11F+D26N+K34Y+T65A+Q327F; P2N+P4S+P11F+T65A+Q327F+I375A+E501V+Y504T; P2N+P4S+P11F+T65A+K218A+K221D+Q327F+E501V+Y504T; P2N+P4S+P11F+T65A+S103N+Q327F+E501V+Y504T; P2N+P4S+T10D+T65A+Q327F+E501V+Y504T; P2N+P4S+F12Y+T65A+Q327F+E501V+Y504T; K5A+P11F+T65A+Q327F+E501V+Y504T; P2N+P4S+T10E+E18N+T65A+Q327F+E501V+Y504T; P2N+T10E+E18N+T65A+Q327F+E501V+Y504T; P2N+P4S+P11F+T65A+Q327F+E501V+Y504T+T568N; P2N+P4S+P11F+T65A+Q327F+E501V+Y504T+K524T+G526A; P2N+P4S+P11F+K34Y+T65A+Q327F+D445N+V447S+E501V+Y504T; P2N+P4S+P11F+R31S+K33V+T65A+Q327F+D445N+V447S+E501V+Y504T; P2N+P4S+P11F+D26N+K34Y+T65A+Q327F+E501V+Y504T; P2N+P4S+P11F+T65A+F80*+Q327F+E501V+Y504T; P2N+P4S+P11F+T65A+K112S+Q327F+E501V+Y504T; P2N+P4S+P11F+T65A+Q327F+E501V+Y504T+T516P+K524T+G526A; P2N+P4S+P11F+T65A+Q327F+E501V+N502T+Y504*; P2N+P4S+P11F+T65A+Q327F+E501V+Y504T; P2N+P4S+P11F+T65A+S103N+Q327F+E501V+Y504T; K5A+P11F+T65A+Q327F+E501V+Y504T; P2N+P4S+P11F+T65A+Q327F+E501V+Y504T+T516P+K524T+G526A; P2N+P4S+P11F+T65A+V79A+Q327F+E501V+Y504T; P2N+P4S+P11F+T65A+V79G+Q327F+E501V+Y504T; P2N+P4S+P11F+T65A+V79I+Q327F+E501V+Y504T; P2N+P4S+P11F+T65A+V79L+Q327F+E501V+Y504T; P2N+P4S+P11F+T65A+V79S+Q327F+E501V+Y504T; P2N+P4S+P11F+T65A+L72V+Q327F+E501V+Y504T; S255N+Q327F+E501V+Y504T; P2N+P4S+P11F+T65A+E74N+Q327F+E501V+Y504T; P2N+P4S+P11F+T65A+G220N+Q327F+E501V+Y504T; P2N+P4S+P11F+T65A+Y245N+Q327F+E501V+Y504T; P2N+P4S+P11F+T65A+Q253N+Q327F+E501V+Y504T; P2N+P4S+P11F+T65A+D279N+Q327F+E501V+Y504T; P2N+P4S+P11F+T65A+Q327F+S359N+E501V+Y504T; P2N+P4S+P11F+T65A+Q327F+D370N+E501V+Y504T; P2N+P4S+P11F+T65A+Q327F+V460S+E501V+Y504T; P2N+P4S+P11F+T65A+Q327F+V460T+P468T+E501V+Y504T; P2N+P4S+P11F+T65A+Q327F+T463N+E501V+Y504T; P2N+P4S+P11F+T65A+Q327F+S465N+E501V+Y504T; or P2N+P4S+P11F+T65A+Q327F+T477N+E501V+Y504T.

In a preferred embodiment the *Penicillium oxalicum* glucoamylase variant has a K79V substitution using SEQ ID NO: 106 herein for numbering (PE001 variant), and further comprises one of the following mutations:

P11F+T65A+Q327F;
P2N+P4S+P11F+T65A+Q327F;
P11F+D26C+K33C+T65A+Q327F;
P2N+P4S+P11F+T65A+Q327W+E501V+Y504T;
P2N+P4S+P11F+T65A+Q327F+E501V+Y504T; or
P11F+T65A+Q327W+E501V+Y504T.

In an embodiment the glucoamylase variant, such as *Penicillium oxalicum* glucoamylase variant has at least 60%, such as at least 70%, such as at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature polypeptide of SEQ ID NO: 106 herein.

The carbohydrate-source generating enzyme, in particular glycoamylase, may be added in amounts from 0.1-100 micrograms EP/g DS, such as 0.5-50 micrograms EP/g DS, such as 1-25 micrograms EP/g DS, such as 2-12 micrograms EP/g DS.

Pullulanase Present and/or Added During Liquefaction

Optionally a pullulanase may be present and/or added during liquefaction step i) together with an alpha-amylase and an optional hemicellulase, preferably xylanase, having a melting point (DSC) above 80° C. As mentioned above a protease, a carbohydrate-source generating enzyme, preferably a thermostable glucoamylase, may also optionally be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in FEMS Mic. Let. (1994) 115, 97-106.

Additional pullulanases contemplated according to the present invention included the pullulanases from *Pyrococcus woesei*, specifically from *Pyrococcus woesei* DSM No. 3773 disclosed in WO 92/02614.

In an embodiment the pullulanase is a family GH57 pullulanase. In an embodiment the pullulanase includes an X47 domain as disclosed in WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown WO 2011/087836 truncated at the X4 site right after the X47 domain. The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in WO 2011/087836 (which is hereby incorporated by reference).

In another embodiment the pullulanase is one comprising an X46 domain disclosed in WO 2011/076123 (Novozymes).

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME 400L, PROMOZYME™ D2 (Novozymes A/S, Denmark), OPTIMAX L-300 (Genencor Int., USA), and AMANO 8 (Amano, Japan).

Phytase Present and/or Added During Liquefaction

Optionally a phytase may be present and/or added in liquefaction in combination with an alpha-amylase and hemicellulase, preferably xylanase, having a melting point (DSC) above 80° C.

A phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any specificity, e.g., be a 3-phytase (EC 3.1.3.8), a 6-phytase (EC 3.1.3.26) or a 5-phytase (no EC number). In an embodiment the phytase has a temperature optimum above 50° C., such as in the range from 50-90° C.

The phytase may be derived from plants or microorganisms, such as bacteria or fungi, e.g., yeast or filamentous fungi.

A plant phytase may be from wheat-bran, maize, soy bean or lily pollen. Suitable plant phytases are described in Thomlinson et al, Biochemistry, 1 (1962), 166-171; Barrientos et al, Plant. Physiol., 106 (1994), 1489-1495; WO 98/05785; WO 98/20139.

A bacterial phytase may be from genus *Bacillus, Citrobacter, Hafnia, Pseudomonas, Buttiauxella* or *Escherichia*, specifically the species *Bacillus subtilis, Citrobacter braakii, Citrobacter freundii, Hafnia alvei, Buttiauxella gaviniae, Buttiauxella agrestis, Buttiauxella noackies* and *E. coli*. Suitable bacterial phytases are described in Paver and Jagannathan, 1982, Journal of Bacteriology 151:1102-1108; Cosgrove, 1970, Australian Journal of Biological Sciences 23:1207-1220; Greiner et al, Arch. Biochem. Biophys., 303, 107-113, 1993; WO 1997/33976; WO 1997/48812, WO 1998/06856, WO 1998/028408, WO 2004/085638, WO 2006/037327, WO 2006/038062, WO 2006/063588, WO 2008/092901, WO 2008/116878, and WO 2010/034835.

A yeast phytase may be derived from genus *Saccharomyces* or *Schwanniomyces*, specifically species *Saccharomyces cerevisiae* or *Schwanniomyces occidentalis*. The former enzyme has been described as a Suitable yeast phytases are described in Nayini et al, 1984, Lebensmittel Wissenschaft und Technologie 17:24-26; Wodzinski et al, Adv. Appl. Microbiol., 42, 263-303; AU-A-24840/95;

Phytases from filamentous fungi may be derived from the fungal phylum of Ascomycota (ascomycetes) or the phylum Basidiomycota, e.g., the genus *Aspergillus, Thermomyces* (also called *Humicola*), *Myceliophthora, Manascus, Penicillium, Peniophora, Agrocybe, Paxillus,* or *Trametes*, specifically the species *Aspergillus terreus, Aspergillus niger, Aspergillus niger* var. *awamori, Aspergillus ficuum, Aspergillus fumigatus, Aspergillus oryzae, T. lanuginosus* (also known as *H. lanuginosa*), *Myceliophthora thermophila, Peniophora lycii, Agrocybe pediades, Manascus anka, Paxillus involtus,* or *Trametes pubescens*. Suitable fungal phytases are described in Yamada et al., 1986, Agric. Biol. Chem. 322:1275-1282; Piddington et al., 1993, Gene 133: 55-62; EP 684,313; EP 0 420 358; EP 0 684 313; WO 1998/28408; WO 1998/28409; JP 7-67635; WO 1998/44125; WO 1997/38096; WO 1998/13480.

In a preferred embodiment the phytase is derived from *Buttiauxella*, such as *Buttiauxella gaviniae, Buttiauxella agrestis,* or *Buttiauxella noackies*, such as the ones disclosed as SEQ ID NO: 2, SEQ ID NO: 4 and SEQ ID NO: 6, respectively, in WO 2008/092901 (hereby incorporated by reference).

In a preferred embodiment the phytase is derived from *Citrobacter*, such as *Citrobacter braakii*, such as one disclosed in WO 2006/037328 (hereby incorporated by reference).

Modified phytases or phytase variants are obtainable by methods known in the art, in particular by the methods disclosed in EP 897010; EP 897985; WO 99/49022; WO 99/48330, WO 2003/066847, WO 2007/112739, WO 2009/129489, and WO 2010/034835.

Commercially available phytase containing products include BIO-FEED PHYTASE™ PHYTASE NOVO™ CT or L (all from Novozymes), LIQMAX (DuPont) or RONOZYME™ NP, RONOZYME® HiPhos, RONOZYME® P5000 (CT), NATUPHOS™ NG 5000 (from DSM).

According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a stain of *Aspergillus*, preferably *A. niger, A. awamori,* or *A. oryzae*; or a strain of *Trichoderma*, preferably *T. reesei*; or a strain of *Talaromyces*, preferably *T. emersonii,*

Glucoamylase

According to the invention the glucoamylase present and/or added in saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), *EMBO J.* 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (*Agric. Biol. Chem.* (1991), 55 (4), p. 941-949), or variants or fragments thereof. Other *Aspergillus* glucoamylase variants include variants with enhanced thermal stability: G137A and G139A (Chen et al. (1996), *Prot. Eng.* 9, 499-505); D257E and D293E/Q (Chen et al. (1995), *Prot. Eng.* 8, 575-582); N182 (Chen et al. (1994), *Biochem. J.* 301, 275-281); disulphide bonds, A246C (Fierobe et al. (1996), *Biochemistry*, 35, 8698-8704; and introduction of Pro residues in position A435 and S436 (Li et al. (1997), *Protein Eng.* 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831).

Contemplated fungal glucoamylases include *Trametes cingulata, Pachykytospora papyracea*; and *Leucopaxillus giganteus* all disclosed in WO 2006/069289; and *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus Pycnoporus, in particular a strain of Pycnoporus as described in WO 2011/066576 (SEQ ID NOs 2, 4 or 6), or from a strain of the genus Gloephyllum, in particular a strain of Gloephyllum as described in WO 2011/068803 (SEQ ID NO: 2, 4, 6, 8, 10, 12, 14 or 16) or a strain of the genus Nigrofomes, in particular a strain of Nigrofomes sp. disclosed in WO 2012/064351 (SEQ ID NO: 2) (all references hereby incorporated by reference). Contemplated are also glucoamylases which exhibit a high identity to any of the above-mentioned glucoamylases, i.e., at least 70%, at least 75%, at least 80%, at least 85%, at least 90%, at least 95%, at least 96%, at least 97%, at least 98%, at least 99%, such as 100% identity to any one of the mature parts of the enzyme sequences mentioned above.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME™ ACHIEVE and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Danisco US).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from Bacillus stearothermophilus strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

Cellulase or Cellulolytic Enzyme Composition Present and/or Added During Saccharification and/or Fermentation or SSF The cellulolytic composition used in a process of the invention may be derived from any microorganism. As used herein, "derived from any microorganism" means that the cellulolytic composition comprises one or more enzymes that were expressed in the microorganism. For instance, a cellulolytic composition derived from a strain of Trichoderma reesei means that the cellulolytic composition comprises one or more enzymes that were expressed in Trichoderma reesei.

In an embodiment, the cellulolytic composition is derived from a strain of Aspergillus, such as a strain of Aspergillus aurantiacus, Aspergillus niger or Aspergillus oryzae.

In an embodiment, the cellulolytic composition is derived from a strain of Chrysosporium, such as a strain of Chrysosporium lucknowense.

In an embodiment, the cellulolytic composition is derived from a strain of Humicola, such as a strain of Humicola insolens.

In an embodiment, the cellulolytic composition is derived from a strain of Penicilium, such as a strain of Penicilium emersonii or Penicilium oxalicum.

In an embodiment, the cellulolytic composition is derived from a strain of Talaromyces, such as a strain of Talaromyces aurantiacus or Talaromyces emersonii.

In an embodiment, the cellulolytic composition is derived from a strain of Trichoderma, such as a strain of Trichoderma reesei.

In a preferred embodiment, the cellulolytic composition is derived from a strain of Trichoderma reesei.

The cellulolytic composition may comprise one or more of the following polypeptides, including enzymes: GH61 polypeptide having cellulolytic enhancing activity, beta-glucosidase, CBHI and CBHII, or a mixture of two, three, or four thereof.

In a preferred embodiment, the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

The cellulolytic composition may comprise some hemicellulase, such as, e.g., xylanase and/or beta-xylosidase. The hemicellulase may come from the cellulolytic composition producing organism or from other sources, e.g., the hemicellulase may be foreign to the cellulolytic composition producing organism, such as, e.g., Trichoderma reesei.

In a preferred embodiment the hemicellulase content in the cellulolytic composition constitutes less than 10 wt. % such as less than 5 wt. % of the cellulolytic composition.

In an embodiment the cellulolytic composition comprises a beta-glucosidase.

In an embodiment the cellulolytic composition comprises a GH61 polypeptide having cellulolytic enhancing activity and a beta-glucosidase.

In another embodiment the cellulolytic composition comprises a beta-glucosidase and a CBH.

In another embodiment the cellulolytic composition comprises a GH61 polypeptide having cellulolytic enhancing activity, a beta-glucosidase, and a CBHI.

In another embodiment the cellulolytic composition comprises a beta-glucosidase and a CBHI.

In another embodiment the cellulolytic composition comprises a GH61 polypeptide having cellulolytic enhancing activity, a beta-glucosidase, a CBHI, and a CBHII.

In another embodiment the cellulolytic composition comprises a beta-glucosidase, a CBHI, and a CBHII.

The cellulolytic composition may further comprise one or more enzymes selected from the group consisting of a cellulase, a GH61 polypeptide having cellulolytic enhancing activity, an esterase, an expansin, a laccase, a ligninolytic enzyme, a pectinase, a peroxidase, a protease, and a swollenin.

In an embodiment the cellulase is one or more enzymes selected from the group consisting of an endoglucanase, a cellobiohydrolase, and a beta-glucosidase.

In an embodiment the endoglucanase is an endoglucanase I.

In an embodiment the endoglucanase is an endoglucanase II.

Beta-Glucosidase

The cellulolytic composition used according to the invention may in one embodiment comprise one or more beta-glucosidase. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or SEQ ID NO: 107 herein or an *Aspergillus fumigatus* beta-glucosidase variant, such as one disclosed in WO 2012/044915 or co-pending PCT application PCT/US11/054185 (or U.S. provisional application No. 61/388,997), such as one with the following substitutions: F100D, S283G, N456E, F512Y.

In another embodiment the beta-glucosidase is derived from a strain of the genus *Penicillium*, such as a strain of the *Penicillium brasilianum* disclosed in WO 2007/019442, or a strain of the genus *Trichoderma*, such as a strain of *Trichoderma reesei*.

In an embodiment betaglucosidase is an *Aspergillus fumigatus* beta-glucosidase or homolog thereof selected from the group consisting of:
 (i) a beta-glucosidase comprising the mature polypeptide of SEQ ID NO: 107;
 (ii) a beta-glucosidase comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 107 herein;
 (iii) a beta-glucosidase encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 5 in WO 2013/148993; and
 (iv) a beta-glucosidase encoded by a polynucleotide that hybridizes under at least high stringency conditions, e.g., very high stringency conditions, with the mature polypeptide coding sequence of SEQ ID NO: 5 in WO 2013/148993 or the full-length complement thereof.

In an embodiment the beta-glucosidase is a variant comprises a substitution at one or more (several) positions corresponding to positions 100, 283, 456, and 512 of the mature polypeptide of SEQ ID NO: 107 herein, wherein the variant has beta-glucosidase activity.

In an embodiment the parent beta-glucosidase of the variant is (a) a polypeptide comprising the mature polypeptide of SEQ ID NO: 107 herein; (b) a polypeptide having at least 80% sequence identity to the mature polypeptide of SEQ ID NO: 107 herein; (c) a polypeptide encoded by a polynucleotide that hybridizes under high or very high stringency conditions with (i) the mature polypeptide coding sequence of SEQ ID NO: 5 in WO 2013/148993, (ii) the cDNA sequence contained in the mature polypeptide coding sequence of SEQ ID NO: 5 in WO 2013/148993, or (iii) the full-length complementary strand of (i) or (ii); (d) a polypeptide encoded by a polynucleotide having at least 80% identity to the mature polypeptide coding sequence of SEQ ID NO: 5 in WO 2013/148993 or the cDNA sequence thereof; or (e) a fragment of the mature polypeptide of SEQ ID NO: 107 herein, which has beta-glucosidase activity.

In an embodiment the beta-glucosidase variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, sequence identity to the amino acid sequence of the parent beta-glucosidase.

In an embodiment the variant has at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100% sequence identity to the mature polypeptide of SEQ ID NO: 107 herein.

In an embodiment the beta-glucosidase is from a strain of *Aspergillus*, such as a strain of *Aspergillus fumigatus*, such as *Aspergillus fumigatus* beta-glucosidase (SEQ ID NO: 107 herein), which comprises one or more substitutions selected from the group consisting of L89M, G91L, F100D, I140V, I186V, S283G, N456E, and F512Y; such as a variant thereof with the following substitutions:
 F100D+S283G+N456E+F512Y;
 L89M+G91L+I186V+I140V;
 I186V+L89M+G91L+I140V+F100D+S283G+N456E+F512Y.

In an embodiment the number of substitutions is between 1 and 4, such as 1, 2, 3, or 4 substitutions.

In an embodiment the variant comprises a substitution at a position corresponding to position 100, a substitution at a position corresponding to position 283, a substitution at a position corresponding to position 456, and/or a substitution at a position corresponding to position 512.

In a preferred embodiment the beta-glucosidase variant comprises the following substitutions: Phe100Asp, Ser283Gly, Asn456Glu, Phe512Tyr in SEQ ID NO: 107 herein.

In a preferred embodiment the beta-glucosidase has a Relative ED50 loading value of less than 1.00, preferably less than 0.80, such as preferably less than 0.60, such as between 0.1-0.9, such as between 0.2-0.8, such as 0.30-0.70.

GH61 Polypeptide Having Cellulolytic Enhancing Activity

The cellulolytic composition used according to the invention may in one embodiment comprise one or more GH61 polypeptide having cellulolytic enhancing activity. In one embodiment the enzyme composition comprises a GH61 polypeptide having cellulolytic enhancing activity, such as one derived from the genus *Thermoascus*, such as a strain of *Thermoascus aurantiacus*, such as the one described in WO 2005/074656 as SEQ ID NO: 2; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 2; or one derived from a strain derived from *Penicillium*, such as a strain of *Penicillium emersonii*, such as the one disclosed in WO 2011/041397 or SEQ ID NO: 108 herein.

In an embodiment the *Penicillium* sp. GH61 polypeptide having cellulolytic enhancing activity or homolog thereof is selected from the group consisting of:
 (i) a GH61 polypeptide having cellulolytic enhancing activity comprising the mature polypeptide of SEQ ID NO: 108 herein;
 (ii) a GH61 polypeptide having cellulolytic enhancing activity comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 108 herein;
 (iii) a GH61 polypeptide having cellulolytic enhancing activity encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 7 in WO 2013/148993; and (iv) a GH61 polypeptide having cellulolytic enhancing activity encoded by a polynucleotide that hybridizes under at least high stringency conditions, e.g., very high stringency conditions, with the mature polypeptide coding sequence of SEQ ID NO: 7 in WO 2013/148993 or the full-length complement thereof.

Cellobiohydrolase I

The cellulolytic composition used according to the invention may in one embodiment may comprise one or more CBH I (cellobiohydrolase 1). In one embodiment the cellulolytic composition comprises a cellobiohydrolase I (CBHI), such as one derived from a strain of the genus *Aspergillus*, such as a strain of *Aspergillus fumigatus*, such as the Cel7A CBHI disclosed in SEQ ID NO: 6 in WO 2011/057140 or SEQ ID NO: 109 herein, or a strain of the genus *Trichoderma*, such as a strain of *Trichoderma reesei*.

In an embodiment the *Aspergillus fumigatus* cellobiohydrolase I or homolog thereof is selected from the group consisting of:

(i) a cellobiohydrolase I comprising the mature polypeptide of SEQ ID NO: 109 herein;

(ii) a cellobiohydrolase I comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 109 herein;

(iii) a cellobiohydrolase I encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 1 in WO 2013/148993; and (iv) a cellobiohydrolase I encoded by a polynucleotide that hybridizes under at least high stringency conditions, e.g., very high stringency conditions, with the mature polypeptide coding sequence of SEQ ID NO: 1 in WO 2013/148993 or the full-length complement thereof.

Cellobiohydrolase II

The cellulolytic composition used according to the invention may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, such as the one in SEQ ID NO: 110 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In an embodiment the *Aspergillus fumigatus* cellobiohydrolase II or homolog thereof is selected from the group consisting of:

(i) a cellobiohydrolase II comprising the mature polypeptide of SEQ ID NO: 110 herein;

(ii) a cellobiohydrolase II comprising an amino acid sequence having at least 70%, e.g., 75%, 80%, 85%, 90%, 91%, 92%, 93%, 94%, 95%, 96%, 97%, 98%, or 99% identity to the mature polypeptide of SEQ ID NO: 110 herein;

(iii) a cellobiohydrolase II encoded by a polynucleotide comprising a nucleotide sequence having at least 70%, e.g., 75%, 80%, 85%, 90%, 91%, 92%, 93%, 94%, 95%, 96%, 97%, 98%, or 99% identity to the mature polypeptide coding sequence of SEQ ID NO: 3 in WO 2013/148993; and (iv) a cellobiohydrolase II encoded by a polynucleotide that hybridizes under at least high stringency conditions, e.g., very high stringency conditions, with the mature polypeptide coding sequence of SEQ ID NO: 3 in WO 2013/148993 or the full-length complement thereof.

Cellulolytic Compositions

As mentioned above the cellulolytic composition may comprise a number of difference polypeptides, such as enzymes.

In an embodiment the cellulolytic composition comprises a *Trichoderma reesei* cellulolytic composition, further comprising *Thermoascus aurantiacus* GH61A polypeptide having cellulolytic enhancing activity (WO 2005/074656) and *Aspergillus oryzae* beta-glucosidase fusion protein (WO 2008/057637).

In another embodiment the cellulolytic composition comprises a *Trichoderma reesei* cellulolytic composition, further comprising *Thermoascus aurantiacus* GH61A polypeptide having cellulolytic enhancing activity (SEQ ID NO: 2 in WO 2005/074656) and *Aspergillus fumigatus* beta-glucosidase (SEQ ID NO: 2 of WO 2005/047499).

In another embodiment the cellulolytic composition comprises a *Trichoderma reesei* cellulolytic composition, further comprising *Penicillium emersonii* GH61A polypeptide having cellulolytic enhancing activity disclosed in WO 2011/041397, *Aspergillus fumigatus* beta-glucosidase (SEQ ID NO: 2 of WO 2005/047499) or a variant thereof with the following substitutions: F100D, S283G, N456E, F512Y.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In a preferred embodiment the cellulolytic composition comprising a beta-glucosidase having a Relative ED50 loading value of less than 1.00, preferably less than 0.80, such as preferably less than 0.60, such as between 0.1-0.9, such as between 0.2-0.8, such as 0.30-0.70.

In an embodiment cellulolytic enzyme composition is dosed (i.e. during saccharification in step ii) and/or fermentation in step iii) or SSF) from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

Protease Present and/or Added During Liquefaction

In an embodiment of the invention an optional protease, such as a thermostable protease, may be present and/or added in liquefaction together with an alpha-amylase, such as a thermostable alpha-amylase, and a hemicellulase, preferably xylanase, having a melting point (DSC) above 80° C., and optionally an endoglucanase, a carbohydrate-source generating enzyme, in particular a glucoamylase, optionally a pullulanase and/or optionally a phytase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section of WO 2017/112540 (incorporated herein by reference), of which the so-called "AZCL-Casein Assay" is the preferred assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the protease activity of the JTP196 variant (Example 2 from WO 2017/112540) or Protease Pfu (SEQ ID NO: 111 herein) determined by the AZCL-casein assay described in the "Materials & Methods"-section in WO 2017/112540.

There are no limitations on the origin of the thermostable protease used in a process or composition of the invention as long as it fulfills the thermostability properties defined below.

In one embodiment the protease is of fungal origin.

In a preferred embodiment the thermostable protease is a variant of a metallo protease as defined above. In an embodiment the thermostable protease used in a process or composition of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 112 herein further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
S70V+D79L+Y82F+S87G+Y97W+A112P+D142L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

In a preferred embodiment the thermostable protease is a variant of the mature metallo protease disclosed as the mature part of SEQ ID NO: 2 disclosed in WO 2003/048353 or the mature part of SEQ ID NO: 1 in WO 2010/008841 or SEQ ID NO: 112 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 112 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company) and SEQ ID NO: 111 herein.

In an embodiment the thermostable protease is one disclosed in SEQ ID NO: 111 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-E1 or SEQ ID NO: 111 herein. The *Pyroccus furiosus* protease can be purchased from Takara Bio, Japan.

The *Pyrococcus furiosus* protease is a thermostable protease according to the invention. The commercial product *Pyrococcus furiosus* protease (Pfu S) was found (see Example 5 of) to have a thermostability of 110% (80° C./70° C.) and 103% (90° C./70° C.) at pH 4.5 determined as described in Example 2 of WO 2017/112540.

In one embodiment a thermostable protease has a thermostability value of more than 20% determined as Relative Activity at 80° C./70° C. determined as described in Example 2.

In an embodiment the protease has a thermostability of more than 30%, more than 40%, more than 50%, more than 60%, more than 70%, more than 80%, more than 90%, more than 100%, such as more than 105%, such as more than 110%, such as more than 115%, such as more than 120% determined as Relative Activity at 80° C./70° C.

In an embodiment protease has a thermostability of between 20 and 50%, such as between 20 and 40%, such as 20 and 30% determined as Relative Activity at 80° C./70° C.

In an embodiment the protease has a thermostability between 50 and 115%, such as between 50 and 70%, such as between 50 and 60%, such as between 100 and 120%, such as between 105 and 115% determined as Relative Activity at 80° C./70° C.

In an embodiment the protease has a thermostability value of more than 10% determined as Relative Activity at 85° C./70° C. determined as described in Example 2 of WO 2017/112540.

In an embodiment the protease has a thermostability of more than 10%, such as more than 12%, more than 14%, more than 16%, more than 18%, more than 20%, more than 30%, more than 40%, more that 50%, more than 60%, more than 70%, more than 80%, more than 90%, more than 100%, more than 110% determined as Relative Activity at 85° C./70° C.

In an embodiment the protease has a thermostability of between 10 and 50%, such as between 10 and 30%, such as between 10 and 25% determined as Relative Activity at 85° C./70° C.

In an embodiment the protease has more than 20%, more than 30%, more than 40%, more than 50%, more than 60%, more than 70%, more than 80%, more than 90% determined as Remaining Activity at 80° C.; and/or In an embodiment the protease has more than 20%, more than 30%, more than 40%, more than 50%, more than 60%, more than 70%, more than 80%, more than 90% determined as Remaining Activity at 84° C.

Determination of "Relative Activity" and "Remaining Activity" is done as described in Example 2 of WO 2017/112540.

In an embodiment the protease may have a themostability for above 90, such as above 100 at 85° C. as determined using the Zein-BCA assay as disclosed in Example 3 of WO 2017/112540.

In an embodiment the protease has a thermostability above 60%, such as above 90%, such as above 100%, such as above 110% at 85° C. as determined using the Zein-BCA assay.

In an embodiment protease has a themostability between 60-120, such as between 70-120%, such as between 80-120%, such as between 90-120%, such as between 100-120%, such as 110-120% at 85° C. as determined using the Zein-BCA assay.

In an embodiment the thermostable protease has at least 20%, such as at least 30%, such as at least 40%, such as at least 50%, such as at least 60%, such as at least 70%, such as at least 80%, such as at least 90%, such as at least 95%, such as at least 100% of the activity of the JTP196 protease variant or Protease Pfu determined by the AZCL-casein assay described in the "Materials & Methods"-section of WO 2017/112540.

V. Further Aspects of the Invention

In a further aspect of the invention it relates to the use of an LPMO polypeptide or enzyme composition comprising at least one LPMO polypeptide for reducing and/or eliminating bacterial contamination in a biofuel fermentation system.

In a further aspect of the invention it relates to the use of an LPMO polypeptide or enzyme composition comprising at least one LPMO polypeptide for reducing and/or eliminating bacterial contamination during yeast propagation.

In a further aspect of the invention it relates to the use of an LPMO polypeptide or enzyme composition comprising at least one LPMO polypeptide for reducing and/or eliminating bacterial contamination in a fermentation medium.

In a further aspect of the invention it relates to the use of an LPMO polypeptide enzyme composition comprising at least one LPMO polypeptide for reducing the levels of lactic acid in a biofuel fermentation system.

In a further aspect of the invention it relates to the use of an LPMO polypeptide or enzyme composition comprising at least one LPMO polypeptide for reducing the levels of lactic acid in a fermentation medium.

In a further aspect of the invention it relates to the use of an LPMO polypeptide or enzyme composition comprising at least one LPMO polypeptide for reducing the levels of lactic acid during yeast propagation.

Those skilled in the art will appreciate that the aspects and embodiments described in this section are applicable to any LPMO, for instance the LPMO's described section III herein.

In an embodiment, the LPMO polypeptide is selected from the group consisting of Auxiliary Activity 9 (AA9), Auxiliary Activity 10 (AA10), Auxiliary Activity 11 (AA11), Auxiliary Activity 13 (AA13), and combinations thereof.

The LPMO polypeptide may be a fungal, bacterial, or archeae LPMO polypeptide. In an embodiment, the LPMO polypeptide is a fungal AA9 polypeptide. In an embodiment, the LPMO polypeptide is a bacterial AA9 polypeptide. In an embodiment, the LPMO is an archeae AA9 polypeptide.

In an embodiment, the LPMO polypeptide is an AA9 selected from the group consisting of:
  i) the Ta AA9 shown in SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  ii) the Pe AA9 shown in SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iii) the Tt AA9 shown in SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iv) the Af AA9 shown in SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  v) the Tc AA9 shown in SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and
  iv) the VL AA9 shown in SEQ ID NO: 6 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

In an embodiment, the LPMO polypeptide is a fungal AA10 polypeptide. In an embodiment, the LPMO polypeptide is a bacterial AA10 polypeptide. In an embodiment, the LPMO is an archeae AA10 polypeptide.

In an embodiment, the LPMO polypeptide is a fungal AA11 polypeptide. In an embodiment, the LPMO polypeptide is a bacterial AA11 polypeptide. In an embodiment, the LPMO is an archeae AA11 polypeptide.

In an embodiment, the LPMO polypeptide is a fungal AA13 polypeptide. In an embodiment, the LPMO polypeptide is a bacterial AA13 polypeptide. In an embodiment, the LPMO is an archeae AA13 polypeptide.

In an embodiment, the LPMO polypeptide is a AA13 polypeptide selected from the group consisting of: i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and iv) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

The invention is further summarized in the following paragraphs:

1. A process for reducing and/or preventing an increase in lactic acid levels in a biofuel fermentation system, the process comprising introducing a LPMO polypeptide or an enzyme composition comprising a lytic polysaccharide monooxygenase (LPMO) polypeptide to a biofuel fermentation system, wherein the fermentation system comprises one or more fermentation vessels, pipes and/or components, and wherein the LPMO polypeptide or enzyme composition comprising the LPMO polypeptide is added at a concentration sufficient to reduce and/or prevent an increase in lactic acid levels in the biofuel fermentation system.
2. A process for reducing and/or eliminating bacterial contamination in a biofuel fermentation system, the process comprising introducing a LPMO polypeptide or an enzyme composition comprising a lytic polysaccharide monooxygenase (LPMO) to a biofuel fermentation system, wherein the fermentation system comprises one or more fermentation vessels, pipes and/or components, and wherein the LPMO polypeptide or enzyme composition comprising the LPMO polypeptide is added at a concentration sufficient to inhibit growth of contaminating bacterial cells in the biofuel fermentation system.
3. The process of paragraph 2, wherein the bacterial cells are gram-positive bacteria or gram-negative bacteria cells.
4. The process of any one of paragraphs 1 to 3, wherein the bacterial cells are *Lactobacillus* cells.
5. The process of any of paragraphs 1 to 4, wherein at least one of the fermentation vessels is a fermentation tank and the LPMO polypeptide or the enzyme composition is introduced into the fermentation tank.
6. The process of any of paragraphs 1 to 5, wherein at least one of the fermentation vessels is a fermentation tank and the LPMO polypeptide or the enzyme composition is introduced into the fermentation tank.
7. The process of any of paragraphs 1 to 6, wherein at least one of the fermentation vessels is a yeast propagation tank and the LPMO polypeptide or the enzyme composition is introduced into the yeast propagation tank.
8. The process of any one of paragraphs 1 to 7, wherein the biofuel is ethanol.
9. The process of any of paragraphs 1 to 8, wherein the LPMO polypeptide is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.
10. The process of any of paragraphs 1 to 9, wherein the LPMO polypeptide is a AA9 polypeptide selected from the group consisting of:
i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and
vi) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

11. The process of any of paragraphs 1 to 10, wherein the LPMO polypeptide is a AA13 polypeptide selected from the group consisting of:
  i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  vi) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  vii) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  viii) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  ix) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  x) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xi) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xii) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xiii) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xiv) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xv) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xvi) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xvii) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xviii) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xix) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xx) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xxi) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
  xxii) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxiii) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and xxiv) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

12. A process for producing a fermentation product from a starch-containing material, the process comprising:
a) liquefying a starch-containing material in the presence of an alpha-amylase to form a liquefied mash;
b) saccharifying the liquefied mash using a carbohydrate source generating enzyme to produce a fermentable sugar;
c) fermenting the sugar using a fermenting organism under conditions suitable to produce the fermentation product, wherein at least one LPMO polypeptide or an enzyme composition comprising an LPMO polypeptide is added before or during saccharifying step b) and/or fermenting step c).

13. The process of paragraph 12, wherein steps b) and c) are carried out simultaneously.

14. The process of paragraph 12 or 13, wherein a slurry of the starch containing material is heated to above the gelatinization temperature.

15. The process of any one of paragraphs 12 to 14, wherein the at least one LPMO polypeptide or enzyme composition is added during liquefaction.

16. The process of any one of paragraphs 12 to 15, wherein the at least one LPMO polypeptide or enzyme composition is added before or during saccharification.

17. The process of any one of paragraphs 12 to 16, wherein the at least one LPMO polypeptide or enzyme composition is added before or during fermentation.

18. The process of any one of paragraphs 12 to 17, wherein the fermenting organism is yeast and the at least one LPMO polypeptide or enzyme composition is added before or during yeast propagation.

19. The process of any one of paragraphs 12 to 18, wherein the fermentation product is an alcohol, preferably ethanol.

20. The process of any one of paragraphs 12 to 19, wherein the bacterial cells are gram-positive bacteria or gram-negative bacteria cells.

21. The process of any one of paragraphs 12 to 20, wherein the bacterial cells are *Lactobacillus* cells.

22. The process of any of any one of paragraphs 12 to 21, wherein the LPMO polypeptide is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

23. The process of any one of paragraphs 12 to 22, wherein the LPMO polypeptide is a AA9 polypeptide selected from the group consisting of:
i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and vi) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

24. The process of any of paragraphs 12 to 23, wherein the LPMO polypeptide is a AA13 polypeptide selected from the group consisting of:
i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

vi) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

vii) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

viii) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

ix) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

x) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xi) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xii) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xiii) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xiv) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xv) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvi) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvii) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xviii) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xix) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xx) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxi) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxii) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxiii) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and xxiv) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

25. Use of an LPMO polypeptide or enzyme composition comprising an LPMO polypeptide for reducing and/or eliminating bacterial contamination in a biofuel fermentation system.

26. Use of an LPMO polypeptide or enzyme composition comprising an LPMO polypeptide for reducing and/or eliminating bacterial contamination during yeast propagation.

27. Use of an LPMO polypeptide or enzyme composition comprising an LPMO polypeptide for reducing the levels of lactic acid during fermentation in an ethanol production process.

28. Use of an LPMO polypeptide or enzyme composition comprising an LPMO polypeptide for reducing the levels of lactic acid during yeast propagation.

29. Use according to any one of paragraphs 25 to 28, wherein the LPMO polypeptide is selected from the group consisting of a Auxiliary Activity 9 (AA9) polypeptide, a Auxiliary Activity 10 (AA10) polypeptide, a Auxiliary Activity 11 (AA11) polypeptide, a Auxiliary Activity 13 (AA13) polypeptide, and combinations thereof.

30. Use according to any one of paragraphs 25 to 29, wherein the LPMO polypeptide is an AA9 polypeptide selected from the group consisting of:
i) the *Thermoascus aurantiacus* AA9 polypeptide of SEQ ID NO: 1 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
ii) the *Penicillium emersonii* AA9 polypeptide of SEQ ID NO: 2 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
iii) the *Thielavia terrestris* AA9 polypeptide of SEQ ID NO: 3 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
iv) the *Aspergillus fumigatus* AA9 polypeptide of SEQ ID NO: 4 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
v) the *Thermoascus crustaceus* AA9 polypeptide of SEQ ID NO: 5 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and
vi) the *Penicillium emersonii* polypeptide of SEQ ID NO: 6 expressed in *Trichoderma reesei* background, or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

31. Use according to any one of paragraphs 25 to 30, wherein the LPMO polypeptide is a AA13 polypeptide selected from the group consisting of:
i) the *Aspergillus terreus* AA13 polypeptide of SEQ ID NO: 119 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
ii) the *Aspergillus lentulus* AA13 polypeptide of SEQ ID NO: 120 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
iii) the *Aspergillus nidulans* polypeptide of SEQ ID NO: 123 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
iv) the *Penicillium polonicum* polypeptide of SEQ ID NO: 124 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
v) the *Penicillium oxalicum* polypeptide of SEQ ID NO: 125 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
vi) the *Mycothermus thermophiles* polypeptide of SEQ ID NO: 127 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
vi) the *Acremonium* sp. XZ1982 polypeptide of SEQ ID NO: 128 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
viii) the *Aspergillus insuetus* polypeptide of SEQ ID NO: 130 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
ix) the *Cladosporium gossypiicola* polypeptide of SEQ ID NO: 131 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
x) the *Fusarium* sp-75363 polypeptide of SEQ ID NO: 132 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
xi) the *Myrothecium* sp. polypeptide of SEQ ID NO: 133 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
xii) the *Paraphoma* sp. polypeptide of SEQ ID NO: 134 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
xiii) the *Penicillium antarcticum* polypeptide of SEQ ID NO: 135 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
xiv) the *Penicillium concentricum* polypeptide of SEQ ID NO: 136 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
xv) the *Penicillium roseopurpureum* polypeptide of SEQ ID NO: 139 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;
xvi) the *Penicillium sclerotiorum* polypeptide of SEQ ID NO: 141 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xvii) the *Penicillium* sp-52627 polypeptide of SEQ ID NO: 142 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xviii) the *Penicillium* sp-72443 polypeptide of SEQ ID NO: 144 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xix) the *Penicillium steckii* polypeptide of SEQ ID NO: 145 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xx) the *Penicillium vulpinum* polypeptide of SEQ ID NO: 147 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxi) the *Pestalotiopsis* sp-71627 polypeptide of SEQ ID NO: 148 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxii) the *Setophaeosphaeria* sp. NN051506 polypeptide of SEQ ID NO: 149 or a variant thereof having at least 60%, at least 65%, at least 70%, at least 75%, at least 80%, at least 85%, at least 90%, at least 95%, at least 96%, at least 97%, at least 98%, or at least 99% sequence identity thereto;

xxiii) the *Talaromyces sayulitensis* polypeptide of SEQ ID NO: 150 or a variant thereof having at least 60%, at least 65%, at least 70%, at least 75%, at least 80%, at least 85%, at least 90%, at least 95%, at least 96%, at least 97%, at least 98%, or at least 99% sequence identity thereto; and xxiv) the *Trichocladium asperum* polypeptide of SEQ ID NO: 151 or a variant thereof having at least 60%, at least 65%, at least 70%, at least 75%, at least 80%, at least 85%, at least 90%, at least 95%, at least 96%, at least 97%, at least 98%, or at least 99% sequence identity thereto.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Materials & Methods

Ta AA9: AA9 polypeptide from *Thermoascus aurantiacus* having the amino acid sequence of SEQ ID NO: 1.

Pe AA9: AA9 polypeptide from *Penicillium emersonii* having the amino acid sequence of SEQ ID NO: 2.

Tt AA9: AA9 polypeptide from *Thielavia terrestris* having the amino acid sequence of SEQ ID NO: 3.

Af AA9: AA9 polypeptide from *Aspergillus fumigatus* having the amino acid sequence of SEQ ID NO: 4.

Tc AA9: AA9 polypeptide from *Thermoascus crustaceus* having the amino acid sequence of SEQ ID NO: 5.

VL-AA9: AA9 polypeptide from *Penicillium emersonii* expressed in *Trichoderma reesei* background having the amino acid sequence of SEQ ID NO: 6.

At-AA13: AA13 polypeptide from *Aspergillus terreus* having the amino acid sequence of SEQ ID NO: SEQ ID NO: 119.

Al-AA13: AA13 polypeptide from *Aspergillus lentulus* having the amino acid sequence of SEQ ID NO: SEQ ID NO: 120.

An-AA13: AA13 polypeptide from *Aspergillus nidulans* having the amino acid sequence of SEQ ID NO: 123.

Pp-AA13: AA13 polypeptide from *Penicillium polonicum* having the amino acid sequence of SEQ ID NO: 124.

Po-AA13: AA13 polypeptide from *Penicillium oxalicum* having the amino acid sequence of SEQ ID NO: 125.

Mt-AA13: AA13 polypeptide from *Mycothermus thermophiles* having the amino acid sequence of SEQ ID NO: 127.

Alpha-Amylase 369 (AA369): *Bacillus stearothermophilus* alpha-amylase with the mutations: I181*+G182*+N193F+V59A+Q89R+E129V+K177L+R179E+Q254S+M284V (SEQ ID NO: 95 herein) truncated to 491 amino acids.

Glucoamylase SA (GSA): Blend comprising *Talaromyces emersonii* glucoamylase disclosed as SEQ ID NO: 34 in WO99/28448, *Trametes cingulata* glucoamylase disclosed as SEQ ID NO: 2 in WO 06/69289, and *Rhizomucor pusillus* alpha-amylase with *Aspergillus niger* glucoamylase linker and starch binding domain (SBD) disclosed in SEQ ID NO: 113 herein having the following substitutions G128D+D143N (activity ratio in AGU:AGU:FAU-F is about 20:5:1).

Protease Pfu: Protease derived from *Pyrococcus furiosus* shown in SEQ ID NO: 111 herein.

EXAMPLES

Example 1—Evaluation of LPMO as Microbial Control Bio-Solution in Biofuels Fermentation This example demonstrates that LPMO's can be used to reduce the levels of bacterial contamination during ethanol fermentation as evidenced by the reduction of levels of a metabolic product of the bacteria present in infected corn mash. In particular, this example demonstrates that LPMO's, such as AA9 polypeptides, can reduce the impact of bacterial contamination in corn mash during ethanol fermentation, as evidenced by a reduction in the levels of lactic acid formation in the fermenting mash.

Clean corn mash: Corn mash was prepared in our laboratories under typical liquefaction conditions using a blend of AA369 and Protease Pfu. Infection was found to be undetectable via plating in selective media. Substrate is frozen and thawed before use.

Infected corn mash: Commercial industrial relevant corn mash with an unknown degree of infection (identified by lactic acid formation and initial cell counts around $10^5$ cells/mL) was incubated overnight and used as our source of contamination.

Control: Clean corn mash plus 1% infected corn mash was used at 36% dry solids and mixed with urea, to a final concentration of 400 ppm, and commercial glucoamylase GSA, at 0.6 AGU per g dry solids in fermentation. The mix was incubated for 60 minutes at 32° C. Thereafter, yeast was added aiming a pitch of 0.5 g/L in fermentation. Six replicates of fermentations were run for 3 days.

Control with commercial antibiotic: Clean corn mash plus 1% infected corn mash was used at 36% dry solids and mixed with urea, to a final concentration of 400 ppm, commercial glucoamylase GSA, at 0.6 AGU per g dry solids in fermentation, and penicillin at 2, 6 or 12 ppm per dry solids. The mix was incubated for 60 minutes at 32° C. Thereafter, yeast was added aiming a pitch of 0.5 g/L in fermentation. Fermentations were run in triplicate for 3 days.

Clean corn mash plus 1% infected corn mash was used at 36% dry solids and mixed with urea, to a final concentration of 400 ppm, commercial glucoamylase GSA, at 0.6 AGU per g dry solids in fermentation, and the AA9 polypeptides listed in the Materials & Methods section above, at 5, 25 or 125 ppm of protein per dry solids. The mix was incubated for 60 minutes at 32° C. Thereafter, yeast was added aiming a pitch of 0.5 g/L in fermentation. Fermentations were run in triplicate for 3 days.

Figure 2:
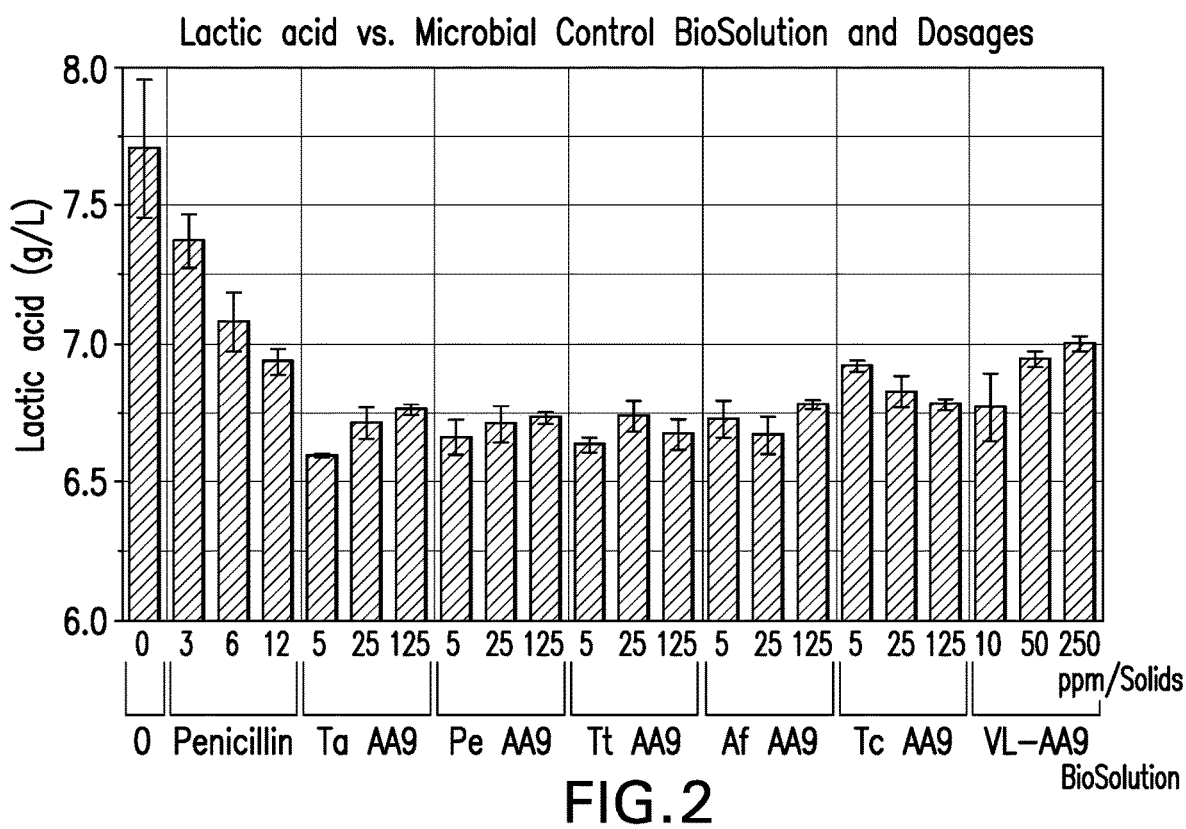
FIG. 2 shows lactic acid concentrations after fermentation of corn mash in the presence of various AA9 polypeptides compared to control (0, 0).
Figure 3:
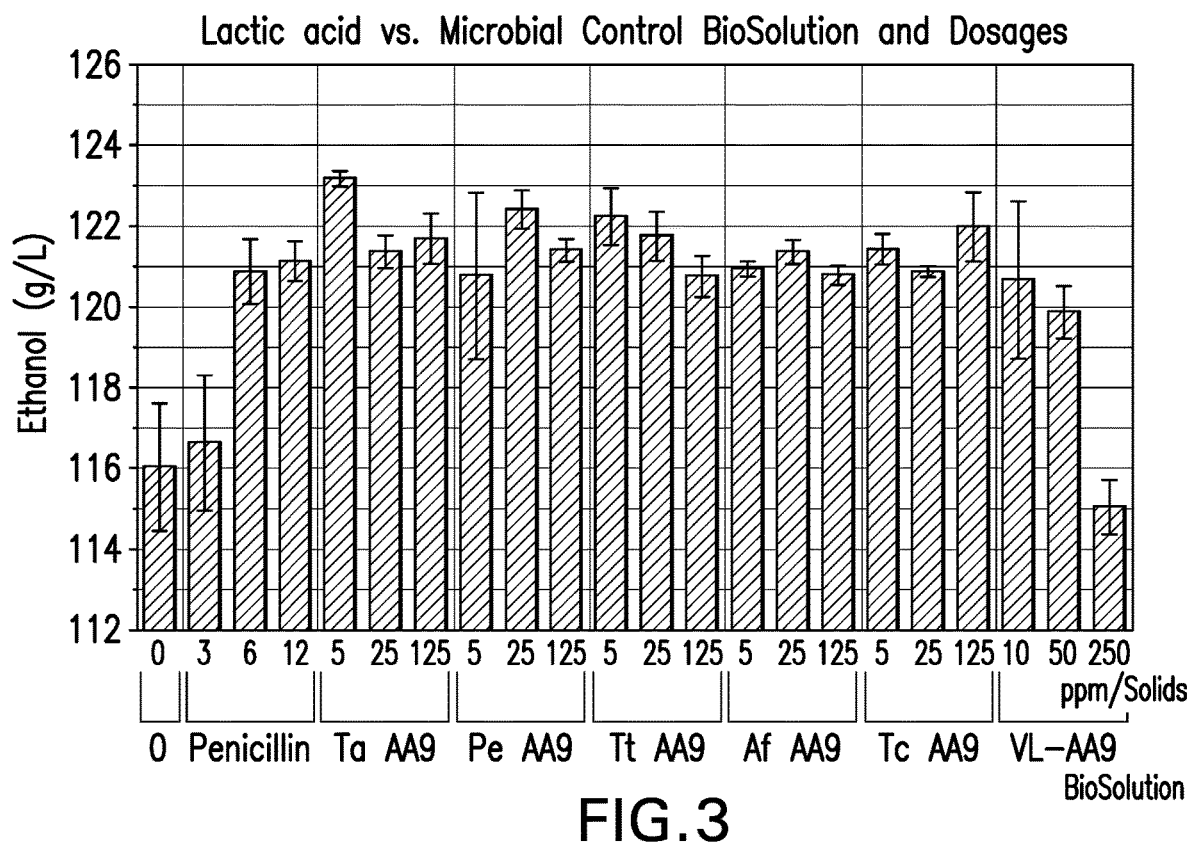
FIG. 3 shows ethanol concentrations after fermentation of corn mash in the presence of various AA9 polypeptides compared to control (0, 0).

FIG. 2 shows lactic acid concentrations after fermentation of corn mash in the presence of various AA9 polypeptides and control (Control, Control with commercial antibiotic). As shown in FIG. 2, each of the AA9 polypeptides tested reduced the lactic acid formation to a greater extent than in the control (no antibiotic used) and comparable to the positive control in which the largest dosage of penicillin was used. These data demonstrate that LPMO's, such as AA9 polypeptides, are effective at reducing the levels of lactic acid formation in an infected mash during ethanol fermentation. FIG. 3 shows ethanol concentrations after fermentation of corn mash in the presence of various AA9 polypeptides and control (Control, Control with commercial antibiotic). As shown in FIG. 3, the AA9 polypeptides tested improved the ethanol formation to a greater extent than in the control (no antibiotic used) and comparable to the positive control in which the largest dosage of penicillin was used. These data demonstrate that LPMO's, such as AA9 polypeptides, are effective at improving the levels of ethanol formation in an infected mash during ethanol fermentation The LPMO's of the present disclosure can be used during ethanol fermentation to reduce the impact of baseline bacterial contamination as well as infection events caused by lactic acid and acetic acid producing bacteria, aligned with improvements in ethanol production, in biofuel fermentation systems.

Example 2—Evaluation of LPMO as Microbial Control Bio-Solution in Biofuels Fermentation This example demonstrates that LPMO's can be used to reduce the impact of bacterial contamination during ethanol fermentation as evidenced by the reduction of levels of a metabolic product of the bacteria present in infected corn mash. In particular, this example demonstrates that LPMO's, such as AA13 polypeptides, can reduce lactic acid produced from unwanted bacterial cells present from during ethanol fermentation.

Clean liquefied corn mash: Clean corn mash was prepared in our laboratories under typical liquefaction conditions using a blend of AA369 and Protease Pfu. Infection rate was found to be undetectable via plating in selective media. Substrate is stored frozen and thawed before use.

Infected liquefied corn mash: Clean corn mash was inoculated with a mixed bacterial population previously isolated from an infected commercial corn mash. The infected mash was incubated with the inoculant for up to 24 hours at approximately 32° C. Final infection rate was found to be greater than $10^8$ colony forming units (CFUs) per plating on MRS selective media. Substrate is frozen in 20% glycerol solution and then thawed before use.

1% Infected liquefied mash: Per every 100 g of "clean" mash, 1 g of infected mash is added and mixed thoroughly.

Fermentation Procedures

Low Dry Solids fermentation. 1% Infected Mash was diluted to 20% dry solids. 200 ppm target urea was added as an exogenous nitrogen source for yeast. Commercial glucoamylase GSA, was used at a dose of 0.6 AGU/g-dry solids. Yeast was pitched at a rate of 0.25 g/L. Experimental enzymes were dosed between 2 ppm and 100 ppm. Dosage were against dry solids.

Positive control: Penicillin was used at 25 ppm.

Negative control: No treatment was added.

Yeast, enzymes, and any additional tap water was added at approximately the same time to start fermentation. Fermentations were incubated in a 32° C. static water bath for up to 24 hours. All treatments were performed in triplicate.

HPLC Analysis

Fermentations were sampled at various time points to examine soluble carbohydrates and organic acids. Samples were first centrifuged at approximately 3 krpm for up to 5 minutes. The supernatant was then filtered through a 0.2 μm filter. The filtrate was diluted up 5× (to be within the linear range of internal standards) with 5 mmolL$^{-1}$ sulfuric acid mobile phase and using an H-column for separation of the analytes. Refractive index was used has detection mode. Analytes were quantified against internal standards. Analytes of interest were: maltotriose, maltose, glucose, fructose, arabinose, lactic acid, glycerol, acetic acid, and ethanol.

Data Analysis

Data was analyzed using SAS JMP statistical software.

Results

Figure 4:
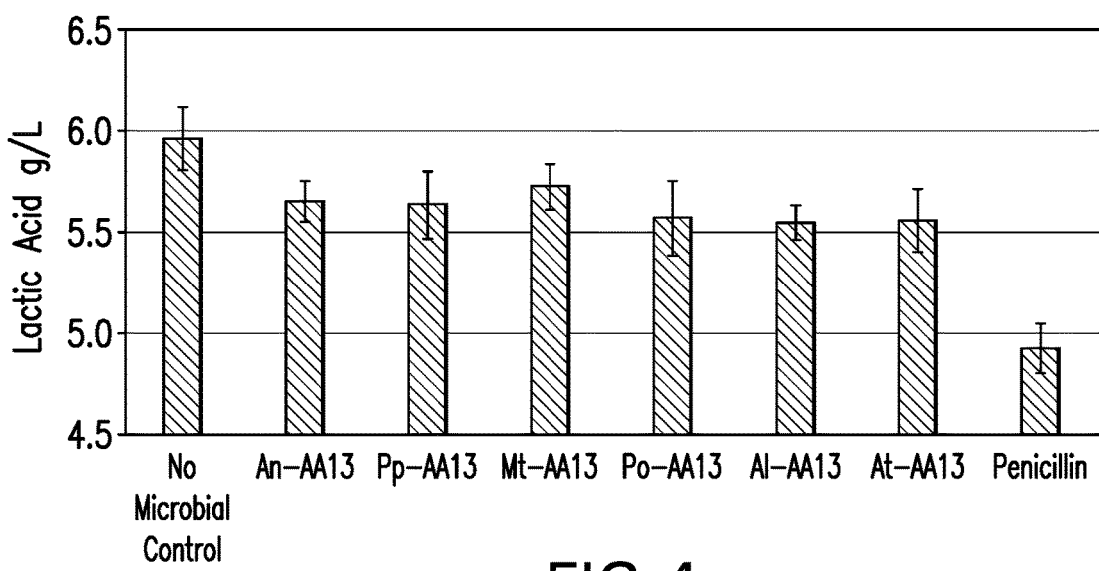
FIG. 4 shows lactic acid concentrations after fermentation of corn mash in the presence of various AA13 polypeptides compared to controls.

At the start of fermentation, treatments have measured lactic acid titers of lower than 0.3 g/L. FIG. 4 shows lactic acid concentrations after 24 hours of Low Dry Solids fermentations of corn mash in the presence of various AA13 polypeptides and controls. As shown in FIG. 4, each of the AA13 polypeptides tested reduced the lactic acid formation more than the negative control. These data suggest that LPMOs, such as AA13 polypeptides, can reduce the levels of lactic formation in an infected mash during ethanol fermentation, like the AA9 polypeptides in Example 1 above.

Figure 5:
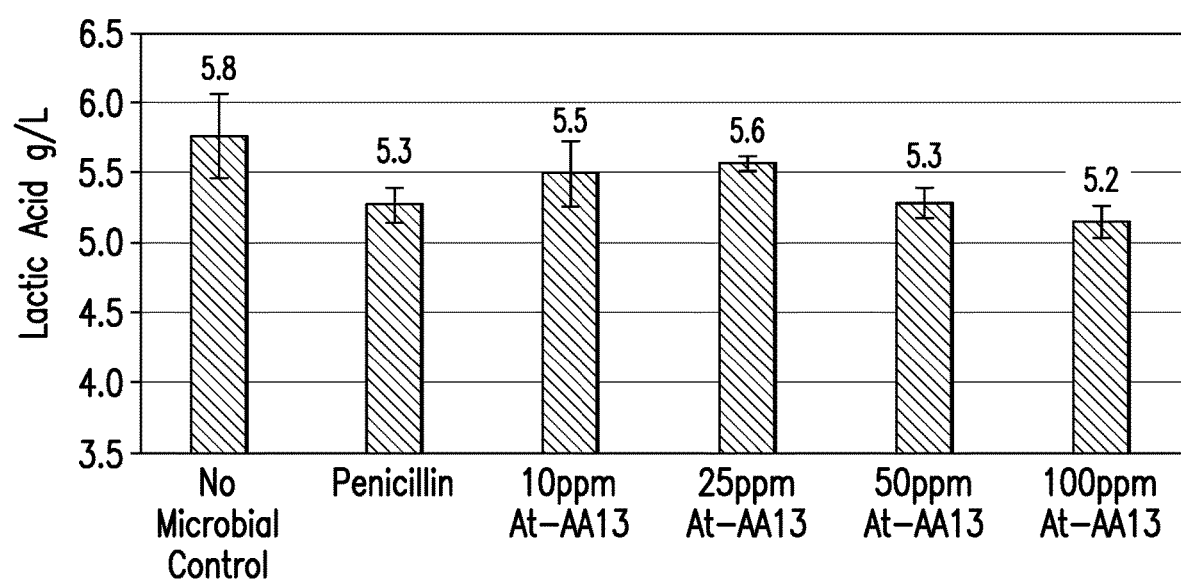
FIG. 5 shows lactic acid concentrations after fermentation of corn mash in the presence of increasing doses of an At-AA13 polypeptide compared to controls.

At-AA13 was selected for additional screening for dose response, and it continued to show reduced lactic acid titers compared to the control after 20 hrs of Low Dry Solids fermentation of corn mash under the above described conditions. These results are shown in FIG. 5.

Example 3—Evaluation of LPMO as Lactic Acid Control Bio-Solution in Biofuels Fermentation This example demonstrates that LPMO's can be used to reduce the levels of lactic acid during ethanol fermentation challenged by infection. In particular, this example demonstrates that LPMO's, such as AA13 polypeptides, can reduce the levels of lactic acid during ethanol fermentation when challenged by infection.

A control mash was prepared in-house with an industry relevant blend of AA369 and Protease Pfu using a Lab-O-Mat incubator for 2 hours at 85° C. and 36% DS to simulate typical industry conditions. The mash was then frozen prior to use in SSF. An infected mash was prepared by infecting the control mash with a multi-strain LAB culture grown in MRS. The bacteria in control mash was incubated overnight, and then frozen with 20% glycerol. For this experiment, 1% weight/weight of the infected mash was mixed into the control mash. This mimics an infection event at a large-scale ethanol facility. For SSF, all mash was prepared with 1000 ppm of urea to aid with yeast fermentation. All treatments were dosed with a baseline commercial glucoamylase GSA, while AA13 candidates were dosed at either 10 ug/g-DS or 50 ug/g-DS. SSF was performed at 5 g scale with 10 uL/g rehydrated Ethanol Red yeast at 32° C. for up to 24 hours at 20% DS. At the end of fermentation, samples were deactivated with 50 uL of 40% sulfuric acid and then centrifuged. The supernatant was filtered through a 0.2 um filter and then measured for soluble carbohydrates and organic acids using an ion-exchange H-column on HPLC.

In this study, several candidates showed decreased lactic acid in addition to increased ethanol compared to the no treatment control at both the high and low dose, as presented in the table below. Candidates of interest are highlighted in bold.

Results:

| Treatment_Dose | Dose in ppm or ug/g-% DS | % de Ita Lactic Acid | % delta Ethanol | average Lactic Acid g/L | average Ethanol g/L |
|---|---|---|---|---|---|
| No Treatment | 0 | 0.0% | 0.0% | 3.3 | 77.6 |
| Penicillin | 25 | −62.4% | 3.1% | 1.2 | 80.1 |
| Aspergillus terreus | 10 | 1.3% | −0.7% | 3.4 | 77.1 |
| Penicillium viticola | 10 | 2.2% | −1.3% | 3.4 | 76.6 |
| Fusarium sp-75363 | 10 | −3.5% | 0.6% | 3.2 | 78.1 |
| Aspergillus insuetus | 10 | 1.7% | −1.2% | 3.4 | 76.7 |
| Penicillium samsonianum | 10 | 2.2% | 0.6% | 3.4 | 77.1 |
| Penicillium sp-52627 | 10 | 3.9% | 0.0% | 3.4 | 77.6 |
| Pestalotiopsis sp-71627 | 10 | 0.0% | 0.5% | 3.3 | 78.0 |
| Myrothecium sp. | 10 | −0.8% | 0.4% | 3.3 | 77.9 |
| Paraphoma sp. | 10 | 1.4% | 1.2% | 3.4 | 78.5 |
| Penicillium vulpinum | 10 | −2.9% | 1.7% | 3.2 | 79.0 |
| Talaromyces sayulitensis | 10 | 1.5% | 1.3% | 3.4 | 78.7 |
| Penicillium steckii | 10 | 4.5% | −1.4% | 3.5 | 76.6 |
| Penicillium antarcticum | 10 | 2.2% | −1.6% | 3.4 | 76.4 |
| Penicillium paxilli | 10 | −4.9% | 0.2% | 3.2 | 77.8 |
| Acremonium sp. XZ1982 | 10 | −9.5% | 1.3% | 3.0 | 78.7 |
| Penicillium sp-72443 | 10 | 12.5% | 2.2% | 2.9 | 79.3 |
| Acrosta lagmus luteoalbus | 10 | −10.9% | 1.7% | 3.0 | 78.9 |
| Cladosporium gossypiicola | 10 | −1.8% | −0.2% | 3.3 | 77.5 |
| Setophaeosphaeria sp. NN051506 | 10 | −0.2% | −0.5% | 3.3 | 77.2 |
| Trichocladium asperum | 10 | −1.5% | 0.5% | 3.3 | 78.0 |
| Penicillium rose opurpureum | 10 | −1.3% | 0.5% | 3.3 | 78.0 |
| Penicillium sclerotiorum | 10 | 6.9% | −1.6% | 3.5 | 76.4 |
| Penicillium sp-54569 | 10 | 3.0% | −1.8% | 3.4 | 76.2 |
| Penicillium hoeksii | 10 | −2.8% | 0.6% | 3.2 | 78.1 |
| Penicillium concentricum | 10 | −0.6% | 0.6% | 3.3 | 78.1 |
| No Treatment | 0 | 0.0% | 0.0% | 3.3 | 77.6 |
| Penicillin | 25 | 62.4% | 3.1% | 1.2 | 80.1 |
| Aspergillus terreus | 50 | 1.3% | 0.4% | 3.4 | 78.0 |
| Penicillium viticola | 50 | 2.8% | 0.2% | 3.4 | 77.8 |
| Fusarium sp-75363 | 50 | −1.6% | 1.2% | 3.3 | 78.5 |
| Aspergillus insuetus | 50 | 2.1% | −0.6% | 3.4 | 77.2 |
| Penicillium samsonianum | 50 | 2.0% | −0.4% | 3.4 | 77.4 |
| Penicillium sp-52627 | 50 | 0.8% | 0.1% | 3.3 | 77.7 |
| Pestalotiopsis sp-71627 | 50 | 2.9% | 0.4% | 3.4 | 78.0 |
| Myrothecium sp. | 50 | −0.9% | 0.7% | 3.3 | 78.2 |
| Paraphoma sp. | 50 | 6.9% | 0.2% | 3.5 | 77.8 |
| Penicillium vulpinum | 50 | 4.6% | 0.9% | 3.5 | 78.3 |
| Talaromyces sayulitensis | 50 | 1.4% | 1.2% | 3.4 | 78.5 |
| Penicillium steckii | 50 | −1.0% | −0.4% | 3.3 | 77.3 |
| Penicillium antarcticum | 50 | 3.0% | −1.8% | 3.4 | 76.2 |
| Penicillium paxilli | 50 | −5.7% | 0.5% | 3.1 | 78.1 |
| Acremonium sp. XZ1982 | 50 | −4.1% | 0.4% | 3.2 | 78.0 |
| Penicillium sp-72443 | 50 | −10.3% | 2.3% | 3.0 | 79.5 |
| Acrostalagmus luteoalbus | 50 | −13.2% | 3.0% | 2.9 | 80.0 |
| Cladosporium gossypiicola | 50 | −4.6% | 1.1% | 3.2 | 78.5 |
| Setophaeosphaeria sp. NN051506 | 50 | −1.7% | −0.1% | 3.3 | 77.5 |
| Trichocladium asperum | 50 | −0.4% | 0.3% | 3.3 | 77.8 |
| Penicillium roseopurpureum | 50 | −1.8% | 0.6% | 3.3 | 78.1 |
| Penicillium sclerotiorum | 50 | −0.9% | 0.6% | 3.3 | 78.1 |
| Penicillium sp-54569 | 50 | −0.6% | −0.3% | 3.3 | 77.4 |
| Penicillium hoeksii | 50 | −4.8% | 1.9% | 3.2 | 79.1 |
| Penicillium concentricum | 50 | −3.2% | 0.7% | 3.2 | 78.2 |

The invention claimed is:

1. A process for reducing and/or preventing an increase in lactic acid levels in a biofuel fermentation system, the process comprising introducing a lytic polysaccharide monooxygenase (LPMO) polypeptide or an enzyme composition comprising the LPMO polypeptide into the biofuel fermentation system, wherein the biofuel fermentation system comprises one or more fermentation vessels, pipes and/or components, and wherein the LPMO polypeptide or enzyme composition comprising the LPMO polypeptide is added at a concentration sufficient to reduce and/or prevent an increase in lactic acid levels in the biofuel fermentation system by reducing and/or preventing bacterial contamination during fermentation.

2. The process of claim 1, wherein at least one of the fermentation vessels is a fermentation tank and the LPMO polypeptide or enzyme composition is introduced into the fermentation tank.

3. The process of claim 1, wherein at least one of the fermentation vessels is a mash cooling system and the LPMO polypeptide or enzyme composition is introduced into the mash cooling system.

4. The process of claim 1, wherein at least one of the fermentation vessels is a yeast propagation tank and the LPMO polypeptide or enzyme composition is introduced into the yeast propagation tank.

5. The process of claim 1, wherein the biofuel is ethanol.

6. The process of claim 1, wherein the LPMO polypeptide is selected from the group consisting of an Auxiliary Activity 9 (AA9) polypeptide, an Auxiliary Activity 10 (AA10) polypeptide, an Auxiliary Activity 11 (AA11) polypeptide, an Auxiliary Activity 13 (AA13) polypeptide, and combinations thereof.

7. The process of claim 1, wherein the LPMO polypeptide is an AA9 polypeptide selected from the group consisting of:
  i) the polypeptide of SEQ ID NO: 1 or one having at least 60% sequence identity thereto;
  ii) the polypeptide of SEQ ID NO: 2 or one having at least 60% sequence identity thereto;
  iii) the polypeptide of SEQ ID NO: 3 or one having at least 60% sequence identity thereto;
  iv) the polypeptide of SEQ ID NO: 4 or one having at least 60% sequence identity thereto;
  v) the polypeptide of SEQ ID NO: 5 or one having at least 60% sequence identity thereto; and
  vi) the polypeptide of SEQ ID NO: 6 expressed in *Trichoderma reesei* background, or one having at least 60% sequence identity thereto expressed in a *Trichoderma reesei* background.

8. The process of claim 1, wherein the LPMO polypeptide is an AA13 polypeptide selected from the group consisting of:
  i) the polypeptide of SEQ ID NO: 119 or one having at least 60% sequence identity thereto;
  ii) the polypeptide of SEQ ID NO: 120 or one having at least 60% sequence identity thereto;
  iii) the polypeptide of SEQ ID NO: 123 or one having at least 60% sequence identity thereto;
  iv) the polypeptide of SEQ ID NO: 124 or one having at least 60% sequence identity thereto;
  v) the polypeptide of SEQ ID NO: 125 or one having at least 60% sequence identity thereto;
  vi) the polypeptide of SEQ ID NO: 127 or one having at least 60% sequence identity thereto;
  vii) the polypeptide of SEQ ID NO: 128 or one having at least 60% sequence identity thereto;
  viii) the polypeptide of SEQ ID NO: 130 or one having at least 60% sequence identity thereto;
  ix) the polypeptide of SEQ ID NO: 131 or one having at least 60% sequence identity thereto;
  x) the polypeptide of SEQ ID NO: 132 or one having at least 60% sequence identity thereto;
  xi) the polypeptide of SEQ ID NO: 133 or one having at least 60% sequence identity thereto;
  xii) the polypeptide of SEQ ID NO: 134 or one having at least 60% sequence identity thereto;
  xiii) the polypeptide of SEQ ID NO: 135 or one having at least 60% sequence identity thereto;
  xiv) the polypeptide of SEQ ID NO: 136 or one having at least 60% sequence identity thereto;
  xv) the polypeptide of SEQ ID NO: 139 or one having at least 60% sequence identity thereto;
  xvi) the polypeptide of SEQ ID NO: 141 or one having at least 60% sequence identity thereto;
  xvii) the polypeptide of SEQ ID NO: 142 or one having at least 60% sequence identity thereto;
  xviii) the polypeptide of SEQ ID NO: 144 or one having at least 60% sequence identity thereto;
  xix) the polypeptide of SEQ ID NO: 145 or one having at least 60% sequence identity thereto;
  xx) the polypeptide of SEQ ID NO: 147 or one having at least 60% sequence identity thereto;
  xxi) the polypeptide of SEQ ID NO: 148 or one having at least 60% sequence identity thereto;
  xxii) the polypeptide of SEQ ID NO: 149 or one having at least 60% sequence identity thereto;
  xxiii) the polypeptide of SEQ ID NO: 150 or one having at least 60% sequence identity thereto;
  xxiv) the polypeptide of SEQ ID NO: 151 or one having at least 60% sequence identity thereto.

9. A process for producing a fermentation product from a starch-containing material, the process comprising:
  a) saccharifying a starch-containing material at a temperature below the initial gelatinization temperature using a carbohydrate source generating enzyme; and
  b) fermenting the saccharified starch-containing material using a fermenting organism,
wherein at least one LPMO polypeptide or enzyme composition comprising at least one LPMO polypeptide is added before or during saccharifying step a) and/or fermenting step b).

10. The process of claim 9, wherein steps a) and b) are carried out simultaneously.

11. The process of claim 9, wherein the at least one LPMO polypeptide or the at least one enzyme composition is added before or during saccharification.

12. The process of claim 9, wherein the at least one LPMO polypeptide or the at least one enzyme composition is added before or during fermentation.

13. The process of claim 9, wherein the fermenting organism is yeast and the at least one LPMO polypeptide or the at least one enzyme composition is added before or during yeast propagation.

14. The process of claim 9, wherein the fermentation product is ethanol.

15. The process of claim 9, wherein the LPMO polypeptide is selected from the group consisting of an Auxiliary Activity 9 (AA9) polypeptide, an Auxiliary Activity 10 (AA10) polypeptide, an Auxiliary Activity 11 (AA11) polypeptide, an Auxiliary Activity 13 (AA13) polypeptide, and combinations thereof.

16. The process of claim 9, wherein the LPMO polypeptide is an AA9 polypeptide selected from the group consisting of:
   i) the polypeptide of SEQ ID NO: 1 or one having at least 60% sequence identity thereto;
   ii) the polypeptide of SEQ ID NO: 2 or one having at least 60% sequence identity thereto;
   iii) the polypeptide of SEQ ID NO: 3 or one having at least 60% sequence identity thereto;
   iv) the polypeptide of SEQ ID NO: 4 or one having at least 60% sequence identity thereto;
   v) the polypeptide of SEQ ID NO: 5 or one having at least 60% sequence identity thereto; and
   vi) the polypeptide of SEQ ID NO: 6 expressed in a *Trichoderma reesei* background, or one having at least 60% sequence identity thereto expressed in a *Trichoderma reesei* background.

17. The process of claim 9, wherein the LPMO polypeptide is an AA13 polypeptide selected from the group consisting of:
   i) the polypeptide of SEQ ID NO: 119 or one having at least 60% sequence identity thereto;
   ii) the polypeptide of SEQ ID NO: 120 or one having at least 60% sequence identity thereto;
   iii) the polypeptide of SEQ ID NO: 123 or one having at least 60% sequence identity thereto;
   iv) the polypeptide of SEQ ID NO: 124 or one having at least 60% sequence identity thereto;
   v) the polypeptide of SEQ ID NO: 125 or one having at least 60% sequence identity thereto;
   vi) the polypeptide of SEQ ID NO: 127 or one having at least 60% sequence identity thereto;
   vii) the polypeptide of SEQ ID NO: 128 or one having at least 60% sequence identity thereto;
   viii) the polypeptide of SEQ ID NO: 130 or one having at least 60% sequence identity thereto;
   ix) the polypeptide of SEQ ID NO: 131 or one having at least 60% sequence identity thereto;
   x) the polypeptide of SEQ ID NO: 132 or one having at least 60% sequence identity thereto;
   xi) the polypeptide of SEQ ID NO: 133 or one having at least 60% sequence identity thereto;
   xii) the polypeptide of SEQ ID NO: 134 or one having at least 60% sequence identity thereto;
   xiii) the polypeptide of SEQ ID NO: 135 or one having at least 60% sequence identity thereto;
   xiv) the polypeptide of SEQ ID NO: 136 or one having at least 60% sequence identity thereto;
   xv) the polypeptide of SEQ ID NO: 139 or one having at least 60% sequence identity thereto;
   xvi) the polypeptide of SEQ ID NO: 141 or one having at least 60% sequence identity thereto;
   xvii) the polypeptide of SEQ ID NO: 142 or one having at least 60% sequence identity thereto;
   xviii) the polypeptide of SEQ ID NO: 144 or one having at least 60% sequence identity thereto;
   xix) the polypeptide of SEQ ID NO: 145 or one having at least 60% sequence identity thereto;
   xx) the polypeptide of SEQ ID NO: 147 or one having at least 60% sequence identity thereto;
   xxi) the polypeptide of SEQ ID NO: 148 or one having at least 60% sequence identity thereto;
   xxii) the polypeptide of SEQ ID NO: 149 or one having at least 60% sequence identity thereto;
   xxiii) the polypeptide of SEQ ID NO: 150 or one having at least 60% sequence identity thereto;
   xxiv) the polypeptide of SEQ ID NO: 151 or one having at least 60% sequence identity thereto.

* * * * *